US012649004B2

(12) United States Patent
Boye et al.

(10) Patent No.: US 12,649,004 B2
(45) Date of Patent: Jun. 9, 2026

(54) HIGHLY EFFICIENT TRANSDUCTION AND LATERAL SPREAD IN THE RETINA BY A NOVEL AAV VIRUS ENHANCED BY RATIONAL DESIGN

(71) Applicant: University of Florida Research Foundation, Incorporated, Gainesville, FL (US)

(72) Inventors: Shannon E. Boye, Gainesville, FL (US); Sanford L. Boye, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1178 days.

(21) Appl. No.: 17/425,292

(22) PCT Filed: Jan. 23, 2020

(86) PCT No.: PCT/US2020/014838
§ 371 (c)(1),
(2) Date: Jul. 22, 2021

(87) PCT Pub. No.: WO2020/154535
PCT Pub. Date: Jul. 30, 2020

(65) Prior Publication Data
US 2022/0133909 A1       May 5, 2022

Related U.S. Application Data

(60) Provisional application No. 62/795,695, filed on Jan. 23, 2019.

(51) Int. Cl.
| | |
|---|---|
| *A61K 48/00* | (2006.01) |
| *C07K 14/005* | (2006.01) |
| *C12N 15/86* | (2006.01) |

(52) U.S. Cl.
CPC ...... *A61K 48/0058* (2013.01); *A61K 48/0075* (2013.01); *C07K 14/005* (2013.01); *C12N 15/86* (2013.01); *C12N 2750/14122* (2013.01); *C12N 2750/14143* (2013.01)

(58) Field of Classification Search
CPC .......... C12N 15/86; C12N 2750/14122; C12N 2750/14143
See application file for complete search history.

(56) References Cited

U.S. PATENT DOCUMENTS

| | | | |
|---|---|---|---|
| 9,873,893 | B2 | 1/2018 | Sieving et al. |
| 9,896,665 | B2 | 2/2018 | Bennett et al. |
| 10,308,957 | B2 | 6/2019 | Boye et al. |
| 2013/0210895 | A1 | 8/2013 | Boye et al. |
| 2016/0369299 | A1 | 12/2016 | Boye et al. |
| 2017/0348387 | A1 | 12/2017 | Aguirre et al. |
| 2018/0355376 | A1* | 12/2018 | Chiorini ................... C12N 9/90 |
| 2021/0123077 | A1 | 4/2021 | Arumugham et al. |
| 2023/0265455 | A1 | 8/2023 | Boye et al. |

FOREIGN PATENT DOCUMENTS

| | | |
|---|---|---|
| CN | 106661591 A | 5/2017 |
| CN | 106906241 A | 6/2017 |
| JP | 2013-526854 A | 6/2013 |
| JP | 2016-510221 A | 4/2016 |
| JP | 2016-517278 A | 6/2016 |
| JP | 2017-510296 A | 4/2017 |
| JP | 2017-518271 A | 7/2017 |
| JP | 2018-515096 A | 6/2018 |
| WO | WO 98/48027 A2 | 10/1998 |
| WO | WO 2003/052052 A2 | 6/2003 |
| WO | WO 2005/003321 A2 | 1/2005 |
| WO | WO 2006/110689 A2 | 10/2006 |
| WO | WO 2014/127196 A1 | 8/2014 |
| WO | WO 2014/144486 A2 | 9/2014 |
| WO | WO 2015/134643 A1 | 9/2015 |
| WO | WO 2015/142941 A1 | 9/2015 |
| WO | WO 2015/152941 A1 | 10/2015 |
| WO | WO 2015/168666 A2 | 11/2015 |
| WO | WO 2016/183297 A1 | 11/2016 |
| WO | WO 2017/070491 A1 | 7/2017 |

(Continued)

OTHER PUBLICATIONS

Boye, Shannon E., et al. "The human rhodopsin kinase promoter in an AAV5 vector confers rod-and cone-specific expression in the primate retina." Human gene therapy 23.10 (2012): 1101-1115. (Year: 2012).*

Invitation to Pay Additional Fees mailed Nov. 29, 2021 for Application No. PCT/US2021/043582.

International Search Report and Written Opinion mailed Jan. 24, 2022 for Application No. PCT/US2021/043582.

Boye et al., Novel AAV44.9-Based Vectors Display Exceptional Characteristics for Retinal Gene Therapy. Mol Ther. Jun. 3, 2020;28(6):1464-1478. doi: 10.1016/j.ymthe.2020.04.002. Epub Apr. 11, 2020.

Buck et al., Recombinant Adeno-Associated Viral Vectors (rAAV)-Vector Elements in Ocular Gene Therapy Clinical Trials and Transgene Expression and Bioactivity Assays. Int J Mol Sci. Jun. 12, 2020;21(12):4197. doi: 10.3390/ijms21124197.

(Continued)

*Primary Examiner* — Jennifer Dunston
*Assistant Examiner* — Christina Tran
(74) *Attorney, Agent, or Firm* — Wolf, Greenfield & Sacks, P.C.

(57) ABSTRACT rAAV particles comprising a new capsid variant, AAV44.9 (E531D) are described herein, as well as a polynucleotide encoding same, and the use of the rAAV particles in the treatment of the eye, including treatment of retinal disorders. The disclosure also shows that the rAAV particles comprising an AAV44.9(E531D) capsid exhibit enhanced lateral spread after subretinal injection to a fovea of the subject, wherein detachment of the fovea is minimized. Methods of treatment comprising administering rAAV particles to a mammal in need thereof, and methods of transducing photoreceptor and RPE cells with rAAV particles, are also provided.

19 Claims, 31 Drawing Sheets
Specification includes a Sequence Listing.

(56) References Cited

FOREIGN PATENT DOCUMENTS

| WO | WO 2018/022608 A2 | 2/2018 |
| WO | WO 2018/156654 A1 | 8/2018 |
| WO | WO 2018/204797 A1 | 11/2018 |
| WO | WO 2019/144077 A1 | 7/2019 |
| WO | WO 2020/236352 A1 | 11/2020 |
| WO | WO 2022/011081 A1 | 1/2022 |
| WO | WO 2022/021405 A1 | 2/2022 |
| WO | WO 2023/081739 A1 | 5/2023 |
| WO | WO 2023/205626 A2 | 10/2023 |
| WO | WO 2023/207672 A1 | 11/2023 |
| WO | WO 2024/097439 A1 | 5/2024 |

OTHER PUBLICATIONS

Ong et al., Adeno-Associated Viral Gene Therapy for Inherited Retinal Disease. Pharm Res. Jan. 7, 2019;36(2):34. doi: 10.1007/s11095-018-2564-5. Author Manuscript, 23 pages.

Powell et al., Viral expression cassette elements to enhance transgene target specificity and expression in gene therapy. Discov Med. Jan. 2015;19(102):49-57. Author Manuscript, 15 pages.

Extended European Search Report mailed Oct. 4, 2022 for Application No. 20744697.2.

International Preliminary Report on Patentability mailed Feb. 9, 2023 for Application No. PCT/US2021/043582.

Andres-Mateos et al., IND-enabling Studies to Support the Clinical Development of ATSN-201, a Subretinally Delivered, Laterally Spreading Gene Replacement Therapy for X-Linked Retinoschisis (XLRS). Ninth Annual Retinal Cell & Gene Therapy Innovation Summit 2024, Abstract, 1 page.

Andres-Mateos, Designing Preclinical Programs to Assess Efficacy and Safety for Novel Viral Vectors. ASGCT 25th Annual Meeting, Viral Vector Development Workshop. May 15, 2022. PowerPoint Presentation, 22 pages.

Bennett et al., Structure/Psychophysical Relationships in X-Linked Retinoschisis. Invest Ophthalmol Vis Sci. Feb. 2016;57(2):332-7. doi: 10.1167/iovs.15-18354.

Boyd et al. Highly Efficient Foveal Cone Transduction by AAV44.9 and AAV2(4pMutΔHS) Mediated by Lateral Spread Following Extrafoveal Subretinal Injection. Invest. Ophthalmol. Vis. Sci. 2019;60(9):1330.

Boye et al., Abstract 32. Highly Efficient Transduction of the Fovea Following 'Extrafoveal' Subretinal Administration of Novel AAV Vectors. Molecular Therapy Apr. 22, 2019 (vol. 27, No. 4, pp. 19-19).

Boye et al., Exploring the Laterally Spreading AAV.SPR Capsid for Treatment of Inherited Retinal Diseases. Gene Therapy for Ophthalmic Disorders Conference, Sep. 14, 2022. PowerPoint Presentation, 34 pages.

Boye et al., Laterally spreading AAV.SPR-hRS1 vector for treatment of XLRS. ASGCT 25th Annual Meeting, 2022. Poster, 1 page.

Boye, AAV-mediated Ocular Gene Therapy: Challenges and Opportunities. SEMM Roundtables. 2021. PowerPoint Presentation, 25 pages.

Boye, IND-enabling Studies to Support the Clinical Development of ATSN-201, a Subretinally Delivered, Laterally Spreading Gene Replacement Therapy for X-Linked Retinoschisis (XLRS). Ninth Annual Retinal Cell & Gene Therapy Innovation Summit 2024. PowerPoint Presentation, 14 pages.

Bush et al., Preclinical Dose-Escalation Study of Intravitreal AAV-RS1 Gene Therapy in a Mouse Model of X-linked Retinoschisis: Dose-Dependent Expression and Improved Retinal Structure and Function. Hum Gene Ther. May 2016;27(5):376-89. doi: 10.1089/hum.2015.142.

Choudhury et al., AAV 44.9—a novel capsid that efficiently transduces photoreceptors and retinal pigment epithelium. ARVO Annual Meeting 2018. Poster, 1 page.

Choudhury et al., AAV 44.9—a novel capsid that efficiently transduces photoreceptors and retinal pigment epithelium. Investigative Ophthalmology & Visual Science. Jul. 2018;59(9):4536.

Couto et al., Laterally spreading AAV. SPR-hRS1 vector for treatment of XLRS. Investigative Ophthalmology & Visual Science. Jun. 1, 2022;63(7):2825-A0341.

Couto et al., Laterally spreading AAV.SPR-hRS1 vector for treatment of XLRS. ARVO Annual Meeting 2022, Poster, 1 page.

Crosson et al., Abstract 936. Novel AAV Capsids Display Expansive Transduction and Enhanced Potency in Subretinally Injected Mice. Molecular Therapy Apr. 22, 2019 (vol. 27, No. 4, pp. 430-431).

Crosson et al., Novel AAV Capsids Display Expansive Transduction and Enhanced Potency in Subretinally Injected Mice. ASGCT 22nd Annual Meeting, 2019. PowerPoint Presentation, 17 pages.

Cukras et al., Retinal AAV8-RS1 Gene Therapy for X-Linked Retinoschisis: Initial Findings from a Phase I/IIa Trial by Intravitreal Delivery. Mol Ther. Sep. 5, 2018;26(9):2282-2294. doi: 10.1016/j.ymthe.2018.05.025. Epub Jul. 7, 2018.

Di Pasquale et al., Abstract 468. AAV44. 9 and Clade E/F Intermediate Virus has Unique Glycan Binding and Transduction Activity. Molecular Therapy Apr. 22, 2019 (vol. 27, No. 4, pp. 222-222).

Janssen et al., Effect of late-stage therapy on disease progression in AAV-mediated rescue of photoreceptor cells in the retinoschisin-deficient mouse. Mol Ther. Jun. 2008;16(6):1010-7. doi: 10.1038/mt.2008.57. Epub Mar. 25, 2008.

Kiraly et al., Morphological and functional parameters in X-linked retinoschisis patients—A multicentre retrospective cohort study. Front Med (Lausanne). Jan. 11, 2024;10:1331889. doi: 10.3389/fmed.2023.1331889.

Ku et al., X-Linked Retinoschisis. Cold Spring Harb Perspect Med. Sep. 1, 2023;13(9):a041288. doi: 10.1101/cshperspect.a041288.

Min et al., Prolonged recovery of retinal structure/function after gene therapy in an Rs1h-deficient mouse model of x-linked juvenile retinoschisis. Mol Ther. Oct. 2005;12(4):644-51. doi: 10.1016/j.ymthe.2005.06.002.

Molday et al., X-linked juvenile retinoschisis: clinical diagnosis, genetic analysis, and molecular mechanisms. Prog Retin Eye Res. May 2012;31(3):195-212. doi: 10.1016/j.preteyeres.2011.12.002. Epub Jan. 3, 2012.

Pennesi et al., Prospective Evaluation of Patients With X-Linked Retinoschisis During 18 Months. Invest Ophthalmol Vis Sci. Dec. 3, 2018;59(15):5941-5956. doi: 10.1167/iovs.18-24565.

Roesch et al., The natural history of X-linked retinoschisis. Can J Ophthalmol. Apr. 1998;33(3):149-58.

Sikkink et al., X-linked retinoschisis: an update. J Med Genet. Apr. 2007;44(4):225-32. doi: 10.1136/jmg.2006.047340. Epub Dec. 15, 2006.

Vandenberghe et al., AAV9 targets cone photoreceptors in the nonhuman primate retina. PLoS One. 2013;8(1):e53463. doi: 10.1371/journal.pone.0053463. Epub Jan. 30, 2013. Erratum in: PLoS One. 2013;8(8). doi:10.1371/annotation/64b90996-4634-4c63-b737-634397b0b445.

Weber et al., Inactivation of the murine X-linked juvenile retinoschisis gene, Rs1h, suggests a role of retinoschisin in retinal cell layer organization and synaptic structure. Proc Natl Acad Sci USA. Apr. 30, 2002;99(9):6222-7. doi: 10.1073/pnas.092528599.

Ye et al., Safety and Biodistribution Evaluation of rAAV2tYF-CB-hRS1, a Recombinant Adeno-Associated Virus Vector Expressing Retinoschisin, in RS1-Deficient Mice. Hum Gene Ther Clin Dev. Sep. 2015;26(3):177-84. doi: 10.1089/humc.2015.077.

U.S. Appl. No. 18/017,726, filed Jan. 24, 2023, Boye.

International Search Report and Written Opinion mailed Apr. 23, 2020 for Application No. PCT/US2020/014838.

International Preliminary Report on Patentability mailed Aug. 5, 2021 for Application No. PCT/US2020/014838.

Nonnenmacher et al., Intracellular transport of recombinant adeno-associated virus vectors. Gene Ther. Jun. 2012;19(6):649-58. doi: 10.1038/gt.2012.6. Epub Feb. 23, 2012.

Boye et al., 358. Safety and Efficacy of ATSN-201 Dose Escalation in Patients with X-linked Retinoschisis (XLRS). Abstract. ASGCT May 13-17, 2025, 28th Annual Meeting New Orleans, 1 page.

Lochrie et al., Mutations on the external surfaces of adeno-associated virus type 2 capsids that affect transduction and neutralization. J Virol. Jan. 2006;80(2):821-34. doi: 10.1128/JVI.80.2.821-834.2006.

* cited by examiner

| Capsid | Mutation | Construct packaged | Titer | Volume |
|---|---|---|---|---|
| AAV5 | | sc-smCBA-mCherry | 3.82E+13 | 100ul |
| AAV8 | Y733F | sc-smCBA-mCherry | 2.59E+12 | 125ul |
| AAV44.9 | | sc-smCBA-mCherry | 1.59E+13 | 125ul |
| AAV44.9 | Y733F | sc-smCBA-mCherry | 1.90E+13 | 125ul |
| AAV44.9 | | pTR-IRBP/GNAT2-hGFP | 7.20E+12 | 120ul |
| AAV44.9 | E531D | sc-smCBA-mCherry | 1.06E+13 | 125ul | endogenous
GFP mCherry nuclear
DAPI
stain

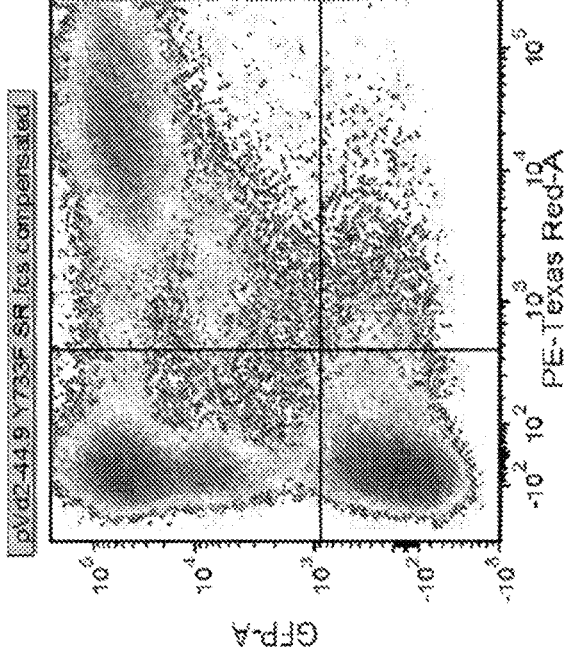
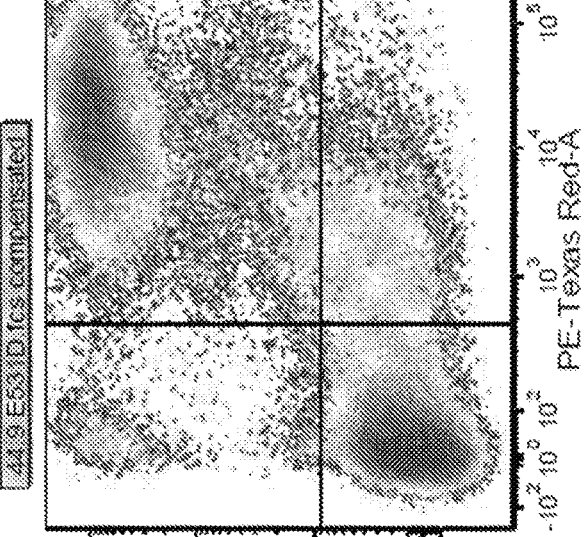
FIG. 4B

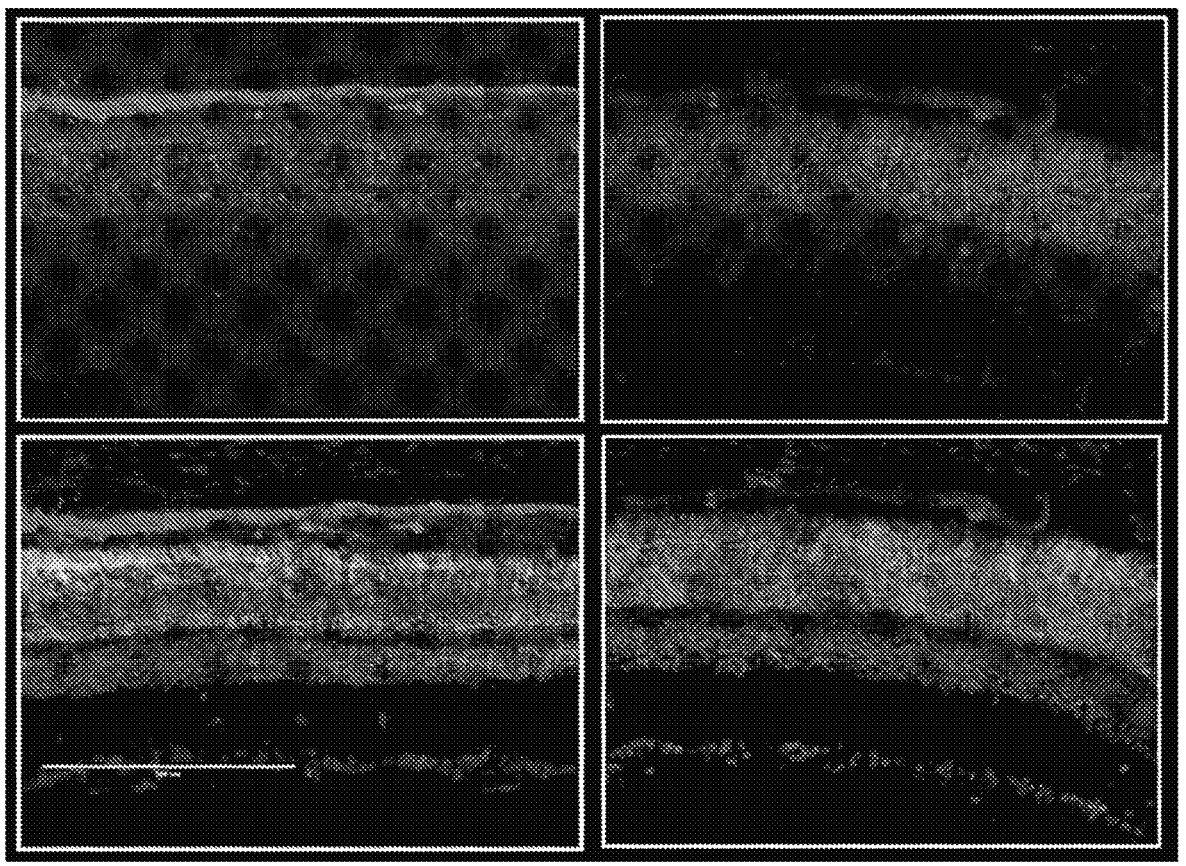
FIG. 5A                          FIG. 5B

| | Rod cells | Non-rod cells |
|---|---|---|
| AAV44.9 | 61.5 | 15.6 |
| AAV44.9- repeat | 70 | 8.6 |
| AAV44.9 E531D | 84.3 | 16.8 |
| AAV44.9 E531D-repeat | 90.6 | 12.8 |

| | Rod cells | Non-rod cells |
|---|---|---|
| AAV44.9 | 65.7 | 12.1 |
| AAV44.9 E531D | 87.4 | 14.8 |
| AAVrh8 | 85.2 | 13.5 |

Cone arrestin
GFP
DAPI

```
                          SEQUENCE LISTING

<160> NUMBER OF SEQ ID NOS: 11

<210> SEQ ID NO 1
<211> LENGTH: 736
<212> TYPE: PRT
<213> ORGANISM: Artificial sequence
<220> FEATURE:
<223> OTHER INFORMATION: Synthetic polypeptide

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
```

-continued

```
                    165                 170                 175

Gly Asp Thr Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
                325                 330                 335

Asn Leu Thr Ser Thr Val Gln Val Phe Thr Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Val Pro Gln Tyr Gly Tyr Leu Thr Leu Asn Asn
    370                 375                 380

Gly Ser Gln Ala Leu Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Val
        435                 440                 445

Arg Thr Gln Thr Thr Gly Thr Gly Gly Thr Gln Thr Leu Ala Phe Ser
    450                 455                 460

Gln Ala Gly Pro Ser Ser Met Ala Ser Gln Ala Arg Asn Trp Val Pro
465                 470                 475                 480

Gly Pro Ser Tyr Arg Gln Gln Arg Val Ser Thr Thr Thr Asn Gln Asn
                485                 490                 495

Asn Asn Ser Asn Phe Ala Trp Thr Gly Ala Ala Lys Phe Lys Leu Asn
            500                 505                 510

Gly Arg Asp Ser Leu Met Asn Pro Gly Val Ala Met Ala Ser His Lys
        515                 520                 525

Asp Asp Asp Asp Arg Phe Phe Pro Ser Ser Gly Val Leu Ile Phe Gly
    530                 535                 540

Lys Gln Gly Ala Gly Asn Asp Gly Val Asp Tyr Ser Gln Val Leu Ile
545                 550                 555                 560

Thr Asp Glu Glu Glu Ile Lys Ala Thr Asn Pro Val Ala Thr Glu Glu
                565                 570                 575

Tyr Gly Ala Val Ala Ile Asn Asn Gln Ala Ala Asn Thr Gln Ala Gln
            580                 585                 590
```

Thr Gly Leu Val His Asn Gln Gly Val Ile Pro Gly Met Val Trp Gln
    595                 600                 605

Asn Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asp Pro Pro Leu Thr Phe Asn Gln Ala Lys Leu Asn Ser Phe Ile Thr
                660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn
    690                 695                 700

Tyr Tyr Lys Ser Thr Asn Val Asp Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 2
<211> LENGTH: 599
<212> TYPE: PRT
<213> ORGANISM: Artificial sequence
<220> FEATURE:
<223> OTHER INFORMATION: Synthetic polypeptide

<400> SEQUENCE: 2

Met Ala Pro Gly Lys Lys Arg Pro Val Glu Gln Ser Pro Gln Glu Pro
1               5                   10                  15

Asp Ser Ser Ser Gly Ile Gly Lys Thr Gly Gln Gln Pro Ala Lys Lys
                20                  25                  30

Arg Leu Asn Phe Gly Gln Thr Gly Asp Thr Glu Ser Val Pro Asp Pro
        35                  40                  45

Gln Pro Leu Gly Glu Pro Pro Ala Ala Pro Ser Gly Leu Gly Pro Asn
    50                  55                  60

Thr Met Ala Ser Gly Gly Gly Ala Pro Met Ala Asp Asn Asn Glu Gly
65                  70                  75                  80

Ala Asp Gly Val Gly Asn Ser Ser Gly Asn Trp His Cys Asp Ser Thr
                85                  90                  95

Trp Leu Gly Asp Arg Val Ile Thr Thr Ser Thr Arg Thr Trp Ala Leu
                100                 105                 110

Pro Thr Tyr Asn Asn His Leu Tyr Lys Gln Ile Ser Asn Gly Thr Ser
        115                 120                 125

Gly Gly Ser Thr Asn Asp Asn Thr Tyr Phe Gly Tyr Ser Thr Pro Trp
    130                 135                 140

Gly Tyr Phe Asp Phe Asn Arg Phe His Cys His Phe Ser Pro Arg Asp
145                 150                 155                 160

Trp Gln Arg Leu Ile Asn Asn Asn Trp Gly Phe Arg Pro Lys Arg Leu
                165                 170                 175

Asn Phe Lys Leu Phe Asn Ile Gln Val Lys Glu Val Thr Thr Asn Glu
                180                 185                 190

Gly Thr Lys Thr Ile Ala Asn Asn Leu Thr Ser Thr Val Gln Val Phe
        195                 200                 205

Thr Asp Ser Glu Tyr Gln Leu Pro Tyr Val Leu Gly Ser Ala His Gln
    210                 215                 220

-continued

```
Gly Cys Leu Pro Pro Phe Pro Ala Asp Val Phe Met Val Pro Gln Tyr
225                 230                 235                 240

Gly Tyr Leu Thr Leu Asn Asn Gly Ser Gln Ala Leu Gly Arg Ser Ser
                245                 250                 255

Phe Tyr Cys Leu Glu Tyr Phe Pro Ser Gln Met Leu Arg Thr Gly Asn
            260                 265                 270

Asn Phe Gln Phe Ser Tyr Thr Phe Glu Asp Val Pro Phe His Ser Ser
            275                 280                 285

Tyr Ala His Ser Gln Ser Leu Asp Arg Leu Met Asn Pro Leu Ile Asp
        290                 295                 300

Gln Tyr Leu Tyr Tyr Leu Val Arg Thr Gln Thr Thr Gly Thr Gly Gly
305                 310                 315                 320

Thr Gln Thr Leu Ala Phe Ser Gln Ala Gly Pro Ser Ser Met Ala Ser
                325                 330                 335

Gln Ala Arg Asn Trp Val Pro Gly Pro Ser Tyr Arg Gln Gln Arg Val
            340                 345                 350

Ser Thr Thr Thr Asn Gln Asn Asn Asn Ser Asn Phe Ala Trp Thr Gly
            355                 360                 365

Ala Ala Lys Phe Lys Leu Asn Gly Arg Asp Ser Leu Met Asn Pro Gly
        370                 375                 380

Val Ala Met Ala Ser His Lys Asp Asp Asp Arg Phe Phe Pro Ser
385                 390                 395                 400

Ser Gly Val Leu Ile Phe Gly Lys Gln Gly Ala Gly Asn Asp Gly Val
                405                 410                 415

Asp Tyr Ser Gln Val Leu Ile Thr Asp Glu Glu Glu Ile Lys Ala Thr
            420                 425                 430

Asn Pro Val Ala Thr Glu Glu Tyr Gly Ala Val Ala Ile Asn Asn Gln
            435                 440                 445

Ala Ala Asn Thr Gln Ala Gln Thr Gly Leu Val His Asn Gln Gly Val
        450                 455                 460

Ile Pro Gly Met Val Trp Gln Asn Arg Asp Val Tyr Leu Gln Gly Pro
465                 470                 475                 480

Ile Trp Ala Lys Ile Pro His Thr Asp Gly Asn Phe His Pro Ser Pro
                485                 490                 495

Leu Met Gly Gly Phe Gly Leu Lys His Pro Pro Gln Ile Leu Ile
                500                 505                 510

Lys Asn Thr Pro Val Pro Ala Asp Pro Pro Leu Thr Phe Asn Gln Ala
            515                 520                 525

Lys Leu Asn Ser Phe Ile Thr Gln Tyr Ser Thr Gly Gln Val Ser Val
        530                 535                 540

Glu Ile Glu Trp Glu Leu Gln Lys Glu Asn Ser Lys Arg Trp Asn Pro
545                 550                 555                 560

Glu Ile Gln Tyr Thr Ser Asn Tyr Tyr Lys Ser Thr Asn Val Asp Phe
                565                 570                 575

Ala Val Asn Thr Glu Gly Val Tyr Ser Glu Pro Arg Pro Ile Gly Thr
            580                 585                 590

Arg Tyr Leu Thr Arg Asn Leu
        595
```

<210> SEQ ID NO 3
<211> LENGTH: 534
<212> TYPE: PRT
<213> ORGANISM: Artificial sequence
<220> FEATURE:

-continued

<223> OTHER INFORMATION: Synthetic polypeptide

<400> SEQUENCE: 3

```
Met Ala Ser Gly Gly Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Gly Thr Ser Gly
    50                  55                  60

Gly Ser Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Asn
            100                 105                 110

Phe Lys Leu Phe Asn Ile Gln Val Lys Glu Val Thr Thr Asn Glu Gly
        115                 120                 125

Thr Lys Thr Ile Ala Asn Asn Leu Thr Ser Thr Val Gln Val Phe Thr
    130                 135                 140

Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Val Pro Gln Tyr Gly
                165                 170                 175

Tyr Leu Thr Leu Asn Asn Gly Ser Gln Ala Leu Gly Arg Ser Ser Phe
            180                 185                 190

Tyr Cys Leu Glu Tyr Phe Pro Ser Gln Met Leu Arg Thr Gly Asn Asn
        195                 200                 205

Phe Gln Phe Ser Tyr Thr Phe Glu Asp Val Pro Phe His Ser Ser Tyr
    210                 215                 220

Ala His Ser Gln Ser Leu Asp Arg Leu Met Asn Pro Leu Ile Asp Gln
225                 230                 235                 240

Tyr Leu Tyr Tyr Leu Val Arg Thr Gln Thr Thr Gly Thr Gly Gly Thr
                245                 250                 255

Gln Thr Leu Ala Phe Ser Gln Ala Gly Pro Ser Ser Met Ala Ser Gln
            260                 265                 270

Ala Arg Asn Trp Val Pro Gly Pro Ser Tyr Arg Gln Gln Arg Val Ser
        275                 280                 285

Thr Thr Thr Asn Gln Asn Asn Asn Ser Asn Phe Ala Trp Thr Gly Ala
    290                 295                 300

Ala Lys Phe Lys Leu Asn Gly Arg Asp Ser Leu Met Asn Pro Gly Val
305                 310                 315                 320

Ala Met Ala Ser His Lys Asp Asp Asp Arg Phe Phe Pro Ser Ser
                325                 330                 335

Gly Val Leu Ile Phe Gly Lys Gln Gly Ala Gly Asn Asp Gly Val Asp
            340                 345                 350

Tyr Ser Gln Val Leu Ile Thr Asp Glu Glu Glu Ile Lys Ala Thr Asn
        355                 360                 365

Pro Val Ala Thr Glu Glu Tyr Gly Ala Val Ala Ile Asn Asn Gln Ala
    370                 375                 380

Ala Asn Thr Gln Ala Gln Thr Gly Leu Val His Asn Gln Gly Val Ile
385                 390                 395                 400
```

-continued

```
Pro Gly Met Val Trp Gln Asn Arg Asp Val Tyr Leu Gln Gly Pro Ile
            405                 410                 415

Trp Ala Lys Ile Pro His Thr Asp Gly Asn Phe His Pro Ser Pro Leu
            420                 425                 430

Met Gly Gly Phe Gly Leu Lys His Pro Pro Pro Gln Ile Leu Ile Lys
        435                 440                 445

Asn Thr Pro Val Pro Ala Asp Pro Pro Leu Thr Phe Asn Gln Ala Lys
    450                 455                 460

Leu Asn Ser Phe Ile Thr Gln Tyr Ser Thr Gly Gln Val Ser Val Glu
465                 470                 475                 480

Ile Glu Trp Glu Leu Gln Lys Glu Asn Ser Lys Arg Trp Asn Pro Glu
            485                 490                 495

Ile Gln Tyr Thr Ser Asn Tyr Tyr Lys Ser Thr Asn Val Asp Phe Ala
            500                 505                 510

Val Asn Thr Glu Gly Val Tyr Ser Glu Pro Arg Pro Ile Gly Thr Arg
            515                 520                 525

Tyr Leu Thr Arg Asn Leu
    530
```

<210> SEQ ID NO 4
<211> LENGTH: 2211
<212> TYPE: DNA
<213> ORGANISM: Artificial sequence
<220> FEATURE:
<223> OTHER INFORMATION: Synthetic polynucleotide

<400> SEQUENCE: 4

```
atggctgccg atggttatct tccagattgg ctcgaggaca acctctctga gggcattcgc      60
gagtggtggg acttgaaacc tggagccccg aaacccaaag ccaaccagca aaagcaggac     120
gacggccggg gtctggtgct tcctggctac aagtacctcg acccctcaa cggactcgac     180 aagggggagc ccgtcaacgc ggcggacgca gcggccctcg agcacgacaa ggcctacgac     240
cagcagctca aagcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga accggtagaa gcagtcaccc caagaaccag actcctcatc gggcatcggc     480
aagacaggcc agcagcccgc taaaaagaga ctcaattttg gtcagactgg cgacacagag     540
tcagtccccg acccacaacc tctcggagaa cctccagcag cccctcagg tctgggacct     600 aatacaatgg cttcaggcgg tggcgctcca atggcagaca taacgaagg cgccgacgga     660 gtgggtaatt cctcgggaaa ttggcattgc gattccacat ggctggggga cagagtcatc     720
accaccagca cccgaacctg ggccctgccc acctacaaca accacctcta caagcaaatc     780
tccaacggca cctcgggagg aagcaccaac gacaacacct actttggcta cagcacccc     840 tggggggtatt ttgacttcaa cagattccac tgccactttt caccacgtga ctggcagcga     900
ctcatcaaca caaattgggg attccggccc aagagactca acttcaagct cttcaacatc     960
caggtcaagg aagtcacgac gaacgaaggc accaagacca tcgccaataa tctcaccagc    1020
accgtgcagg tctttacgga ctcggagtac cagctaccgt acgtgctagg atcagctcac    1080
cagggatgtc tgcctccgtt cccggcggac gtcttcatgg ttcctcagta cggttatcta    1140
actctgaaca atggcagcca ggccctggga cgttcctcct tctactgcct ggagtatttc    1200
ccatcgcaga tgctgagaac cggcaacaac tttcagttca gctacacctt cgaggacgtg    1260
```

-continued

```
cctttccaca gcagctacgc gcacagccaa agcctggaca ggctgatgaa tcccctcatc   1320
gaccagtacc tgtattacct ggtcagaacg cagacaaccg ggactggagg gacgcagact   1380
ctggcattca gccaagcagg ccctagctca atggccagcc aggctagaaa ctgggtgccc   1440
ggaccgagct accggcagca gcgcgtctcc acgacaacca accagaacaa caacagcaac   1500
tttgcctgga cgggagctgc caaatttaaa ctgaacggcc gagactctct aatgaacccc   1560
ggcgtggcca tggcttcaca caaggatgac gatgaccggt tcttcccttc tagcggggtc   1620
ctgattttcg gcaagcaagg agccgggaat gatggagtgg attacagcca agtgctgatt   1680
acagatgagg aagaaatcaa ggctaccaac cccgtggcaa cagaggaata tggagcagtg   1740
gccatcaaca accaggccgc taatacgcag gcgcagaccg gactcgtgca caaccagggg   1800
gtgattcccg gcatggtgtg gcagaacaga gacgtgtacc tgcagggtcc catctgggcc   1860
aaaattcctc acacggacgg caactttcac ccgtctcccc tgatgggcgg ctttggactg   1920
aagcacccgc ctcctcaaat tctcatcaag aacacaccgg ttccagcgga cccgccgctt   1980
accttcaacc aggccaagct gaactctttc atcacgcagt acagcaccgg acaggtcagc   2040
gtggaaatcg agtgggagct gcagaaagaa aacagcaaac gctggaatcc agagattcag   2100
tacacttcca actactacaa atctacaaat gtggactttg ctgtcaacac ggaaggagtg   2160
tatagcgagc ctcgccccat tggcacgcgc tacctcaccc gtaatctgta a          2211
```

<210> SEQ ID NO 5
<211> LENGTH: 1800
<212> TYPE: DNA
<213> ORGANISM: Artificial sequence
<220> FEATURE:
<223> OTHER INFORMATION: Synthetic polynucleotide

<400> SEQUENCE: 5

```
acggctcctg gaaagaagag accggtagag cagtcacccc aagaaccaga ctcctcatcg    60
ggcatcggca agacaggcca gcagcccgct aaaaagagac tcaattttgg tcagactggc   120
gacacagagt cagtccccga cccacaacct ctcggagaac ctccagcagc cccctcaggt   180 ctggaccta atacaatggc ttcaggcggt ggcgctccaa tggcagacaa taacgaaggc   240
gccgacggag tgggtaattc ctcgggaaat tggcattgcg attccacatg gctggggac   300 agagtcatca ccaccagcac ccgaacctgg gccctgccca cctacaacaa ccacctctac   360
aagcaaatct ccaacggcac ctcgggagga agcaccaacg acaacaccta ctttggctac   420
agcaccccct gggggtattt tgacttcaac agattccact gccactttc accacgtgac   480 tggcagcgac tcatcaacaa caattgggga ttccggccca agagactcaa cttcaagctc   540
ttcaacatcc aggtcaagga agtcacgacg aacgaaggca ccaagaccat cgccaataat   600
ctcaccagca ccgtgcaggt ctttacggac tcggagtacc agctaccgta cgtgctagga   660
tcagctcacc agggatgtct gcctccgttc ccggcggacg tcttcatggt tcctcagtac   720
ggttatctaa ctctgaacaa tggcagccag gccctgggac gttcctcctt ctactgcctg   780
gagtatttcc catcgcagat gctgagaacc ggcaacaact tcagttcag ctacaccttc   840 gaggacgtgc ctttccacag cagctacgcg cacagccaaa gcctggacag gctgatgaat   900
cccctcatcg accagtacct gtattacctg gtcagaacgc agacaaccgg gactggaggg   960
acgcagactc tggcattcag ccaagcaggc cctagctcaa tggccagcca ggctagaaac  1020
tgggtgccgg accgagcta ccggcagcag cgcgtctcca cgacaaccaa ccagaacaac  1080
aacagcaact ttgcctggac gggagctgcc aaatttaaac tgaacggccg agactctcta  1140
```

-continued

```
atgaacccg gcgtggccat ggcttcacac aaggatgacg atgaccggtt cttcccttct    1200 agcgggtcc tgattttcgg caagcaagga gccgggaatg atggagtgga ttacagccaa    1260
gtgctgatta cagatgagga agaaatcaag gctaccaacc ccgtggcaac agaggaatat    1320
ggagcagtgg ccatcaacaa ccaggccgct aatacgcagg cgcagaccgg actcgtgcac    1380 aaccagggggg tgattcccgg catggtgtgg cagaacagag acgtgtacct gcagggtccc    1440
atctgggcca aaattcctca cacggacggc aactttcacc cgtctcccct gatgggcggc    1500
tttggactga agcacccgcc tcctcaaatt ctcatcaaga acacaccggt tccagcggac    1560
ccgccgctta ccttcaacca ggccaagctg aactctttca tcacgcagta cagcaccgga    1620
caggtcagcg tggaaatcga gtgggagctg cagaaagaaa acagcaaacg ctggaatcca    1680
gagattcagt acacttccaa ctactacaaa tctacaaatg tggactttgc tgtcaacacg    1740
gaaggagtgt atagcgagcc tcgccccatt ggcacgcgct acctcacccg taatctgtaa    1800
```

<210> SEQ ID NO 6
<211> LENGTH: 1605
<212> TYPE: DNA
<213> ORGANISM: Artificial sequence
<220> FEATURE:
<223> OTHER INFORMATION: Synthetic polynucleotide

<400> SEQUENCE: 6

```
atggcttcag gcggtggcgc tccaatggca gacaataacg aaggcgccga cggagtgggt      60
aattcctcgg gaaattggca ttgcgattcc acatggctgg gggacagagt catcaccacc     120
agcacccgaa cctgggccct gcccacctac aacaaccacc tctacaagca aatctccaac     180
ggcacctcgg gaggaagcac caacgacaac acctactttg ctacagcac ccccctgggggg     240 tattttgact tcaacagatt ccactgccac ttttcaccac gtgactggca gcgactcatc     300
aacaacaatt gggggattccg gcccaagaga ctcaacttca gctcttcaa catccaggtc     360 aaggaagtca cgacgaacga aggcaccaag accatcgcca ataatctcac cagcaccgtg     420 caggtctttta cggactcgga gtaccagcta ccgtacgtgc taggatcagc tcaccaggga     480
tgtctgcctc cgttcccggc ggacgtcttc atggttcctc agtacggtta tctaactctg     540
aacaatggca gccaggccct gggacgttcc tccttctact gcctggagta tttcccatcg     600
cagatgctga gaaccggcaa caactttcag ttcagctaca ccttcgagga cgtgcctttc     660
cacagcagct acgcgcacag ccaaagcctg gacaggctga tgaatcccct catcgaccag     720
tacctgtatt acctggtcag aacgcagaca accgggactg gagggacgca gactctggca     780
ttcagccaag caggccctag ctcaatggcc agccaggcta gaaactgggt gcccggaccg     840
agctaccggc agcagcgcgt ctccacgaca accaaccaga caacaacag caactttgcc     900 tggacgggag ctgccaaatt aaactgaac ggccgagact ctctaatgaa ccccggcgtg     960
gccatggctt cacacaagga tgacgatgac cggttcttcc cttctagcgg ggtcctgatt    1020
ttcggcaagc aaggagccgg gaatgatgga gtggattaca gccaagtgct gattacagat    1080
gaggaagaaa tcaaggctac caaccccgtg gcaacagagg aatatggagc agtggccatc    1140
aacaaccagg ccgctaatac gcaggcgcag accggactcg tgcacaacca gggggtgatt    1200
cccggcatgg tgtggcagaa cagagacgtg tacctgcagg gtcccatctg ggccaaaatt    1260
cctcacacgg acggcaactt tcacccgtct cccctgatgg gcggctttgg actgaagcac    1320
ccgcctcctc aaattctcat caagaacaca ccggttccag cggacccgcc gcttaccttc    1380
```

-continued

```
aaccaggcca agctgaactc tttcatcacg cagtacagca ccggacaggt cagcgtggaa      1440
atcgagtggg agctgcagaa agaaaacagc aaacgctgga atccagagat tcagtacact      1500
tccaactact acaaatctac aaatgtggac tttgctgtca acacggaagg agtgtatagc      1560
gagcctcgcc ccattggcac gcgctacctc acccgtaatc tgtaa                      1605
```

```
<210> SEQ ID NO 7
<211> LENGTH: 736
<212> TYPE: PRT
<213> ORGANISM: Unknown
<220> FEATURE:
<223> OTHER INFORMATION: AAV44.9 VP1

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Thr Glu Ser Val Pro Asp Pro Gln Pro Leu Gly Glu Pro Pro
            180                 185                 190

Ala Ala Pro Ser Gly Leu Gly Pro Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Gly Thr Ser Gly Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Glu Gly Thr Lys Thr Ile Ala Asn
```

-continued

```
                    325                 330                 335
Asn Leu Thr Ser Thr Val Gln Val Phe Thr Asp Ser Glu Tyr Gln Leu
            340                 345                 350
Pro Tyr Val Leu Gly Ser Ala His Gln Gly Cys Leu Pro Pro Phe Pro
            355                 360                 365
Ala Asp Val Phe Met Val Pro Gln Tyr Gly Tyr Leu Thr Leu Asn Asn
    370                 375                 380
Gly Ser Gln Ala Leu Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Thr
                405                 410                 415
Phe Glu Asp Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Val
            435                 440                 445
Arg Thr Gln Thr Thr Gly Thr Gly Gly Thr Gln Thr Leu Ala Phe Ser
    450                 455                 460
Gln Ala Gly Pro Ser Ser Met Ala Ser Gln Ala Arg Asn Trp Val Pro
465                 470                 475                 480
Gly Pro Ser Tyr Arg Gln Gln Arg Val Ser Thr Thr Thr Asn Gln Asn
                485                 490                 495
Asn Asn Ser Asn Phe Ala Trp Thr Gly Ala Ala Lys Phe Lys Leu Asn
            500                 505                 510
Gly Arg Asp Ser Leu Met Asn Pro Gly Val Ala Met Ala Ser His Lys
            515                 520                 525
Asp Asp Glu Asp Arg Phe Phe Pro Ser Ser Gly Val Leu Ile Phe Gly
    530                 535                 540
Lys Gln Gly Ala Gly Asn Asp Gly Val Asp Tyr Ser Gln Val Leu Ile
545                 550                 555                 560
Thr Asp Glu Glu Glu Ile Lys Ala Thr Asn Pro Val Ala Thr Glu Glu
                565                 570                 575
Tyr Gly Ala Val Ala Ile Asn Asn Gln Ala Ala Asn Thr Gln Ala Gln
            580                 585                 590
Thr Gly Leu Val His Asn Gln Gly Val Ile Pro Gly Met Val Trp Gln
            595                 600                 605
Asn Arg Asp Val Tyr Leu Gln Gly Pro Ile Trp Ala Lys Ile Pro His
    610                 615                 620
Thr Asp Gly Asn Phe His Pro Ser Pro Leu Met Gly Gly Phe Gly Leu
625                 630                 635                 640
Lys His Pro Pro Pro Gln Ile Leu Ile Lys Asn Thr Pro Val Pro Ala
                645                 650                 655
Asp Pro Pro Leu Thr Phe Asn Gln Ala Lys Leu Asn Ser Phe Ile Thr
            660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
    690                 695                 700
Tyr Tyr Lys Ser Thr Asn Val Asp Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735
```

<210> SEQ ID NO 8

-continued

<211> LENGTH: 2211
<212> TYPE: DNA
<213> ORGANISM: Unknown
<220> FEATURE:
<223> OTHER INFORMATION: AAV44.9 VP1

<400> SEQUENCE: 8

```
atggctgccg atggttatct tccagattgg ctcgaggaca acctctctga gggcattcgc        60
gagtggtggg acttgaaacc tggagccccg aaacccaaag ccaaccagca aaagcaggac       120
gacggccggg gtctggtgct tcctggctac aagtacctcg acccttcaa cggactcgac        180 aaggggagc ccgtcaacgc ggcggacgca gcggccctcg agcacgacaa ggcctacgac        240
cagcagctca aagcgggtga caatccgtac ctgcggtata accacgccga cgccgagttt       300
caggagcgtc tgcaagaaga tacgtctttt gggggcaacc tcgggcgagc agtcttccag       360
gccaagaagc gggttctcga acctctcggt ctggttgagg aaggcgctaa gacggctcct       420
ggaaagaaga gaccggtaga gcagtcaccc caagaaccag actcctcatc gggcatcggc       480
aagacaggcc agcagcccgc taaaaagaga ctcaattttg gtcagactgg cgacacagag       540
tcagtccccg acccacaacc tctcggagaa cctccagcag cccctcagg tctgggacct        600 aatacaatgg cttcaggcgg tggcgctcca atggcagaca taacgaagg cgccgacgga        660 gtgggtaatt cctcgggaaa ttggcattgc gattccacat ggctggggga cagagtcatc       720
accaccagca cccgaacctg ggccctgccc acctacaaca accacctcta caagcaaatc       780
tccaacggca cctcgggagg aagcaccaac gacaacacct actttggcta cagcaccccc       840
tgggggtatt ttgacttcaa cagattccac tgccactttt caccacgtga ctggcagcga       900
ctcatcaaca caattgggg attccggccc aagagactca acttcaagct cttcaacatc        960
caggtcaagg aagtcacgac gaacgaaggc accaagacca tcgccaataa tctcaccagc       1020
accgtgcagg tctttacgga ctcggagtac cagctaccgt acgtgctagg atcagctcac       1080
cagggatgtc tgcctccgtt cccggcggac gtcttcatgg ttcctcagta cggttatcta       1140
actctgaaca atggcagcca ggccctggga cgttcctcct ctactgcct ggagtatttc        1200 ccatcgcaga tgctgagaac cggcaacaac tttcagttca gctacacctt cgaggacgtg       1260
cctttccaca gcagctacgc gcacagccaa gcctggaca ggctgatgaa tcccctcatc        1320
gaccagtacc tgtattacct ggtcagaacg cagacaaccg gactggagg acgcagact        1380 ctggcattca gccaagcagg ccctagctca atggccagcc aggctagaaa ctgggtgccc       1440
ggaccgagct accggcagca gcgcgtctcc acgacaacca accagaacaa caacagcaac       1500
tttgcctgga cgggagctgc caaatttaaa ctgaacggcc gagactctct aatgaacccc       1560
ggcgtggcca tggcttcaca caaggatgac gaggaccgct tcttcccttc tagcgggggtc       1620 ctgattttcg gcaagcaagg agccgggaat gatggagtgg attacagcca agtgctgatt       1680
acagatgagg aagaaatcaa ggctaccaac cccgtggcaa cagaggaata tggagcagtg       1740
gccatcaaca accaggccgc taatacgcag gcgcagaccg actcgtgca caaccagggg        1800 gtgattcccg gcatggtgtg gcagaacaga gacgtgtacc tgcagggtcc catctgggcc       1860
aaaattcctc acacggacgg caactttcac cgtctccccc tgatgggcgg ctttggactg       1920
aagcacccgc tcctcaaat tctcatcaag aacacaccgg ttccagcgga cccgccgctt       1980
accttcaacc aggccaagct gaactctttc atcacgcagt acagcaccgg acaggtcagc       2040
gtggaaatcg agtgggagct gcagaaagaa aacagcaaac gctggaatcc agagattcag       2100
tacacttcca actactacaa atctacaaat gtggactttg ctgtcaacac ggaaggagtg       2160
```

-continued tatagcgagc ctcgccccat tggcacgcgc tacctcaccc gtaatctgta a          2211

<210> SEQ ID NO 9
<211> LENGTH: 3312
<212> TYPE: DNA
<213> ORGANISM: Homo sapiens

<400> SEQUENCE: 9
atgaccgcct gcgcccgccg agcgggtggg cttccggacc ccgggctctg cggtcccgcg      60
tggtgggctc cgtccctgcc ccgcctcccc cgggccctgc cccggctccc gctcctgctg     120
ctcctgcttc tgctgcagcc ccccgccctc tccgccgtgt tcacggtggg ggtcctgggc     180
ccctgggctt gcgaccccat cttctctcgg gctcgcccgg acctggccgc ccgcctggcc     240 gccgcccgc tgaaccgcga ccccggcctg gcaggcggtc cccgcttcga ggtagcgctg     300
ctgcccgagc cttgccggac gccgggctcg ctgggggccg tgtcctccgc gctggcccgc     360
gtgtcgggcc tcgtgggtcc ggtgaaccct gcggcctgcc ggccagccga gctgctcgcc     420
gaagaagccg ggatcgcgct ggtgccctgg ggctgcccct ggacgcaggc ggagggcacc     480
acggcccctg ccgtgacccc cgccgcggat gccctctacg ccctgcttcg cgcattcggc     540
tgggcgcgcg tggccctggt caccgccccc caggacctgt gggtggaggc gggacgctca     600
ctgtccacgg cactcagggc ccggggcctg cctgtcgcct ccgtgacttc catggagccc     660
ttggacctgt ctggagcccg ggaggccctg aggaaggttc gggacgggcc cagggtcaca     720
gcagtgatca tggtgatgca ctcggtgctg ctgggtggcg aggagcagcg ctacctcctg     780
gaggccgcag aggagctggg cctgaccgat ggctccctgg tcttcctgcc cttcgacacg     840
atccactacg ccttgtcccc aggcccggag gccttggccg cactcgccaa cagctcccag     900
cttcgcaggg cccacgatgc cgtgctcacc ctcacgcgcc actgtccctc tgaaggcagc     960
gtgctggaca gcctgcgcag ggctcaagag cgccgcgagc tgccctctga cctcaatctg    1020
cagcaggtct ccccactctt tggcaccatc tatgacgcgg tcttcttgct ggcaaggggc    1080
gtggcagaag cgcgggctgc cgcaggtggc agatgggtgt ccggagcagc tgtggcccgc    1140
cacatccggg atgcgcaggt ccctggcttc tgcgggacc taggaggaga cgaggagccc    1200
ccattcgtgc tgctagacac ggacgcggcg ggagaccggc tttttgccac atacatgctg    1260
gatcctgccc ggggctcctt cctctccgcc ggtacccgga tgcacttccc gcgtggggga    1320
tcagcacccg gacctgaccc ctcgtgctgg ttcgatccaa acaacatctg cggtggagga    1380
ctggagccgg gctcgtctt tcttggcttc ctcctggtgg ttgggatggg gctggctggg    1440
gccttcctgg cccattatgt gaggcaccgg ctacttcaca tgcaaatggt ctccggcccc    1500
aacaagatca tcctgaccgt ggacgacatc acctttctcc acccacatgg gggcacctct    1560
cgaaaggtgg cccaggggag tcgatcaagt ctgggtgccc gcagcatgtc agacattcgc    1620
agcggcccca gccaacactt ggacagcccc aacattggtg tctatgaggg agacagggtt    1680
tggctgaaga aattcccagg ggatcagcac atagctatcc gcccagcaac caagacggcc    1740
ttctccaagc tccaggagct ccggcatgag aacgtggccc tctacctggg gcttttcctg    1800
gctcggggag cagaaggccc tgcggccctc tgggagggca acctggctgt ggtctcagag    1860
cactgcacgc ggggctctct tcaggacctc ctcgctcaga gagaaataaa gctggactgg    1920
atgttcaagt cctccctcct gctggacctt atcaagggaa taaggtatct gcaccatcga    1980
ggcgtggctc atgggcggct gaagtcacgg aactgcatag tggatggcag attcgtactc    2040

-continued

```
aagatcactg accacggcca cgggagactg ctggaagcac agaaggtgct accggagcct      2100
cccagagcgg aggaccagct gtggacagcc ccggagctgc ttagggaccc agccctggag      2160 cgccgggaa cgctggccgg cgacgtcttt agcttggcca tcatcatgca agaagtagtg      2220
tgccgcagtg cccccttatgc catgctggag ctcactcccg aggaagtggt gcagagggtg      2280
cggagccccc ctccactgtg tcggccccttg gtgtccatgg accaggcacc tgtcgagtgt      2340
atcctcctga tgaagcagtg ctgggcagag cagccggaac ttcggccctc catggaccac      2400
accttcgacc tgttcaagaa catcaacaag ggccggaaga cgaacatcat tgactcgatg      2460
cttcggatgc tggagcagta ctctagtaac ctggaggatc tgatccggga gcgcacggag      2520
gagctggagc tggaaaagca gaagacagac cggctgctta cacagatgct gcctccgtct      2580
gtggctgagg ccttgaagac ggggacacca gtggagcccg agtactttga gcaagtgaca      2640
ctgtacttta gtgacattgt gggcttcacc accatctctg ccatgagtga gcccattgag      2700
gttgtggacc tgctcaacga tctctacaca ctctttgatg ccatcattgg ttcccacgat      2760
gtctacaagg tggagacaat aggggacgcc tatatggtgg cctcggggct gccccagcgg      2820
aatgggcagc gacacgcggc agagatcgcc aacatgtcac tggacatcct cagtgccgtg      2880
ggcactttcc gcatgcgcca tatgcctgag gttcccgtgc gcatccgcat aggcctgcac      2940
tcgggtccat gcgtggcagg cgtggtgggc ctcaccatgc cgcggtactg cctgtttggg      3000
gacacggtca acaccgcctc gcgcatggag tccaccgggc tgccttaccg catccacgtg      3060
aacttgagca ctgtggggat tctccgtgct ctggactcgg gctaccaggt ggagctgcga      3120
ggccgcacgg agctgaaggg caagggcgcc gaggacactt tctggctagt gggcagacgc      3180
ggcttcaaca gcccatccc caaaccgcct gacctgcaac cggggtccag caaccacggc      3240
atcagcctgc aggagatccc acccgagcgg cgacggaagc tggagaaggc gcggccgggc      3300
cagttctctt ga                                                          3312
```

```
<210> SEQ ID NO 10
<211> LENGTH: 3327
<212> TYPE: DNA
<213> ORGANISM: Homo sapiens

<400> SEQUENCE: 10
```

```
atgagcgctt ggctcctgcc agccggaggg cttcccggcg ccgggttctg tgtccctgcg       60
cggcagtctc cgtccagttt ctcgcgggtc ctgcgctggc caaggcctgg gctaccggga      120
ctcctgctac tgctactgct cccatctcct tctgccctct ctgctgtgtt caaagtgggg      180
gtgctgggcc cctgggcttg cgaccccatc tttgcacggg cccgaccaga cctggctgcg      240
cgtctggccg ccaaccgcct gaatcgtgac tttgctttag acggcggccc ccggttcgag      300
gttgcgctgc tcccagagcc ctgcctgact ccgggctcac tagggctgt gtcctctgcg      360 ctgtctcgag tctctggcct ggtgggtccg gtgaacccccg cagcctgtcg gccagccgaa      420
ctgttggctc aagaagctgg agtagcgctg gtgccctggg gctgccctgg cacgcgggcg      480
gcgggtacta cagccccggc ggtgaccccc gctgcagatg ctctctacgt cctccttaga      540
gcattccgct gggcgcgcgt ggccctgatc actgcacccc aagacctgtg ggtggaggcg      600
ggacgcgctc tgtccacagc actcagggcc cggggtttgc cagttgccct agtgacttcc      660
atggagactt cagaccggtc tggagcccgg gaggccctcg gaggatccg agatgggcct      720 agagttagag tagtgatcat ggtgatgcac tcggtgctgc tgggcggcga ggagcagcgc      780
tacctactgg aagctgcaga agaactggct ctgactgatg gctccctggt tttcctgccc      840
```

```
ttcgacacgc ttcactacgc tttgtctcca ggcccggagg ctctggctgc atttgtcaac      900
agctcccagc tccgcagggc tcacgatgcg gtgctcacac tcacgcgccg ctgtcctcct      960
ggaggcagcg tgcaagacag cctgcgcagg gctcaagaac accaggaact gccccttgac     1020
ctcaacctga agcaggtctc tccgctgttt ggcaccatct atgatgctgt cttcctgttg     1080
gctgggggcg tgaagagagc aagaacagcg gtgggtggtg gctgggtgtc aggtgcatct     1140
gtagcccgcc aagtacggga agcacaagtc tctggctttt gtggggtcct gggaagaacc     1200
gaggagccct cctttgtgct gctggacaca gatgcatccg gagaacagtt gttcgcaaca     1260
cacctgctag atcctgtctt aggctccctg cgttctgcag ggaccccat gcacttccct       1320 agaggtggac ctgccccggg accagaccct tcctgctggt tcgatccaga tgtgatctgc      1380 aacgagggg tggagccagg cctggtcttt gttggcttcc tcctggtgat agggatggga      1440
ctgactggag ccttcttggc tcattacttg aggcacaggc tgctacacat gcagatggct      1500
tccggcccca acaagatcat cttgacgttg gaagatgtta ctttcctcca cccaccggga     1560
ggcagctctc gaaaggtggt ccagggaagt agatccagtc tggctacccg gagcgcatca     1620
gacattcgca gtgtccccag ccagccccaa gagagcacca cgttggcct ctatgagggg       1680 gactgggttt ggctgaagaa gttcccaggg aacatcata tggctatcag gccagcaaca       1740
aagacagcct ctccaagct tcgagagctc cggcatgaga atgtggctct ctacttggga       1800
ctcttcctgg cgggtacagc agacagccct gccacccctg gggagggcat cttggctgtg      1860
gtctcagagc actgtgctcg gggttccctc catgacctcc tggcccagag agaaataaag      1920
ctggactgga tgttcaagtc ttccctcctg ctggacctca tcaagggaat gagatatctg      1980
caccatcgcg gtgtggccca cgggaggctc aagtcacgga attgcgtggt ggacgggagg     2040
ttcgtgctca aggtgacaga tcatggccat gggcgactgc tggaagcgca aagggtgtta     2100
ccggaacctc ccagtgcaga ggatcagcta tggacagccc cagagcttct tcgggacccc     2160
tccctggagc gccgggggaac tctagctggt gatgtcttta gtctggccat catcatgcag     2220
gaggtcgtgt gccgcagcac cccttatgcc atgctggaac taacgcccga ggaagtaata     2280
cagagggtgc ggagccctcc tccactgtgt cggcccttgg tgtccatgga ccaggcaccc     2340
atggagtgca tccagctgat gacacaatgc tgggcagagc atccagaact tcggccttcc     2400
atggacctca cctttgacct gttcaagagc atcaacaagg gccggaagac caacatcatc     2460
gactccatgc ttcggatgct ggagcagtac tctagtaacc tggaggatct gatccgagaa     2520
cgcacagagg agttagagca ggagaagcag aagacagaca ggctgctcac acagatgctg     2580
cctccatctg tggctgaggc cctgaagatg gggacatctg tggagcctga gtactttgaa     2640 gaggtgcacac tctacttcag tgacatcgtg ggctttacca ccatttcagc catgagcgag     2700
cctattgagg tggtagacct gcttaatgac ctctatactc tcttcgatgc catcatcggt     2760
gcccatgatg tctataaggt ggaaacaatt ggagatgcat atatggtggc ctccgggctg     2820
ccgcagagga acgggcagcg gcacgctgca gagattgcca acatgtcact ggacatcctc     2880
agtgcagtcg gctccttccg catgcgccat atgcccgagg taccggtgcg catccgcatt     2940
ggtttgcact caggccgtg cgtggcgggt gtggtgggcc tcaccatgcc tcggtactgc     3000
ctgttcgggg acacggtcaa cactgcctcg agaatggagt ccactggact gccttaccgc     3060
atccacgtta acatgagcac tgttcggatt cttcgcgctc tggaccaagg cttccagatg     3120
gagtgtcgag gccgcacgga gctgaagggc aagggtattg aggacacgta ctggcttgtg     3180
```

-continued

```
ggcagacttg gcttcaacaa gcccattccc aaaccacctg atctgcagcc aggggccagc     3240
aaccatggta tcagcctgca ggagattccc ccagagagac gcaagaagct ggagaaagcc     3300
aggccaggcc agtttactgg gaagtga                                         3327

<210> SEQ ID NO 11
<211> LENGTH: 292
<212> TYPE: DNA
<213> ORGANISM: Homo sapiens

<400> SEQUENCE: 11
gggccccaga agcctggtgg ttgtttgtcc ttctcagggg aaaagtgagg cggcccttg       60 gaggaagggg ccgggcagaa tgatctaatc ggattccaag cagctcaggg gattgtcttt     120
ttctagcacc ttcttgccac tcctaagcgt cctccgtgac cccggctggg atttagcctg     180
gtgctgtgtc agccccggtc tcccaggggc ttcccagtgg tccccaggaa ccctcgacag     240
ggcccggtct ctctcgtcca gcaagggcag ggacgggcca caggccaagg gc             292
```

HIGHLY EFFICIENT TRANSDUCTION AND LATERAL SPREAD IN THE RETINA BY A NOVEL AAV VIRUS ENHANCED BY RATIONAL DESIGN

RELATED APPLICATIONS

This application is a national stage filing under 35 U.S.C. 371 of International Patent Application Serial No. PCT/US2020/014838, filed Jan. 23, 2020, entitled "HIGHLY EFFICIENT TRANSDUCTION AND LATERAL SPREAD IN THE RETINA BY A NOVEL AAV VIRUS ENHANCED BY RATIONAL DESIGN", which claims the benefit of the filing date of U.S. Provisional Application No. 62/795,695 filed Jan. 23, 2019, entitled "HIGHLY EFFICIENT TRANSDUCTION AND LATERAL SPREAD IN THE RETINA BY A NOVEL AAV VIRUS ENHANCED BY RATIONAL DESIGN", the entire contents of which are incorporated herein by reference in their entireties.

FEDERALLY SPONSORED RESEARCH

This invention was made with government support under grant number R01 EY024280 awarded by the National Institutes of Health. The government has certain rights in the invention.

FIELD OF THE INVENTION

The present invention relates generally to the fields of molecular biology and virology, and in particular, to the development of gene therapy vectors and methods for treatment of retinal diseases.

BACKGROUND OF THE INVENTION

Major advances in the field of gene therapy have been achieved by using viruses to deliver therapeutic genetic material. The adeno-associated virus has attracted considerable attention as a highly effective viral vector for gene therapy due to its low immunogenicity and ability to effectively transduce non-dividing cells. AAV has been shown to infect a variety of cell and tissue types, and significant progress has been made over the last decade to adapt this viral system for use in human gene therapy.

In its normal "wild type" form, AAV DNA is packaged into the viral capsid as a single-stranded molecule about 4600 nucleotides (nt) in length. Following infection of the cell by the virus, the molecular machinery of the cell converts the single-stranded DNA into a double-stranded form. Only this double-stranded DNA form may be transcribed by cellular enzymes into RNA, which is then translated into polypeptides by additional cellular pathways.

Recombinant adeno-associated virus (AAV) vectors have been used successfully for in vivo gene transfer in numerous pre-clinical animal models of human disease, and have been used successfully for long-term expression of a wide variety of therapeutic genes (Daya and Berns, 2008; Niemeyer et al., 2009; Owen et al., 2002; Keen-Rhinehart et al., 2005; Scallan et al., 2003; Song et al., 2004). AAV vectors have also generated long-term clinical benefit in humans when targeted to immune-privileged sites, e.g., ocular delivery for Leber's congenital amaurosis (Bainbridge et al., 2008; Maguire et al., 2008; Cideciyan et al., 2008). A major advantage of this vector is its comparatively low immune profile, eliciting only limited inflammatory responses and, in some cases, even directing immune tolerance to transgene products (LoDuca et al., 2009). Nonetheless, the therapeutic efficiency, when targeted to non-immune privileged organs, has been limited in humans due to antibody and CD8+ T cell responses against the viral capsid, while in animal models, adaptive responses to the transgene product have also been reported (Manno et al., 2006; Mingozzi et al., 2007; Muruve et al., 2008; Vandenberghe and Wilson, 2007; Mingozzi and High, 2007).

Subretinal injection of AAV is commonly used when transgene expression is required in the retinal pigment epithelium (RPE) or the photoreceptors (PR). The subretinal injection creates a temporary bullous detachment, separating the photoreceptor outer segments from the RPE layer. Typically the subretinal injection bleb resolves over the following few days in subjects. Subretinal injection likely has some deleterious effects on the photoreceptors, with such effects conceivably being more severe in a retina already compromised by disease. In particular, it has been suggested that detaching the fovea in RPE65-LCA patients undergoing retinal gene therapy treatment may be detrimental (see Jacobson et al., Gene therapy for leber congenital amaurosis caused by RPE65 mutations: safety and efficacy in 15 children and adults followed up to 3 years, *Arch Ophthalmol.* 2012; 130(1):9-24).

There is still a need for AAV capsids to increase retinal transduction efficiency and minimize detachment of the fovea during subretinal injection.

SUMMARY OF THE INVENTION

AAV has become the vector of choice for targeting therapeutic genes to the retina. Both naturally occurring and synthetic AAVs have been identified that display retinal tropism. Recently, a novel AAV capsid serotype, 44.9, was isolated from a laboratory stock of simian adenovirus SV15 taken from normal rhesus monkey kidney cell culture. Reference is made to WO 2016/183297, published Nov. 17, 2016; U.S. Patent Publication No. 2018/0355376, published Dec. 13, 2018; and *Novel Adeno-Associated Virus for Gene Therapy*, Fed. Reg. 80, 149 (Aug. 4, 2015), the entire contents of each of which are incorporated herein in their entireties. AAV44.9 efficiently transduces a number of cell types including salivary gland cells, liver cells, and different types of neurons (e.g., cells of the cortex, olfactory bulb, brain stem, and Purkinje cells of the cerebellum).

AAV44.9 exhibits comparable in vivo biodistribution to AAV9. Intracerebroventricular injections of this capsid have shown transduction levels in the cortex, olfactory bulb, cerebellum, choroid plexus and brain stem similar to those observed with AAV9. In addition, antibody neutralization studies suggest a lower frequency of neutralizing antibodies to AAV44.9 compared with AAV2. And glycan array studies of AAV44.9 have suggested binding of the capsid to terminal glucose-containing molecules.

The amino acid sequence of capsid protein VP1 of AAV44.9 differs from the amino acid sequence of capsid protein VP1 of the most closely reported isolate AAVrh.8R (see Vandenberghe L H et al., Naturally occurring singleton residues in AAV capsid impact vector performance and illustrate structural constraints, *Gene Ther.* 16:1416-1418 (2009); Vandenberghe L H, et al., AAV9 targets cone photoreceptors in the nonhuman primate retina, *PLoS One* 8(1):e53463 (2013)) at several locations, two of which are serine residues in variable domain 3. In particular, the amino acid sequence of capsid protein VP1 of AAV44.9 differs at positions 179, 473 and 483 relative to the amino acid sequence of capsid protein VP1 of AAVrh.8R.

The amino acid sequence of capsid protein VP1 of AAV44.9 differs from the amino acid sequence of capsid protein VP1 of closely reported isolate AAVrh.8 (see Gao et al., *J. Virol.* 78(12): 6381-6388 (2004)) at several locations, two of which are serine residues in variable domain 3. In particular, the amino acid sequence of capsid protein VP1 of AAV44.9 differs at positions 179, 473, 483 and 531 relative to the amino acid sequence of capsid protein VP1 of AAVrh.8.

Rational mutagenesis studies of amino acids in capsid proteins have suggested that some mutations have an inhibitory effect of the gene transfer activity of the vector, specifically the presence of serine and threonine residues in variable regions. Reports indicate that these amino acids increase the surface charge of the particles and target them for degradation in the lysosome, and that substitution with other non-charged amino acids can improve the transduction activity. In addition, mutations of residues implicated in receptor interactions also have a large effect on retinal transduction and tropism. In the context of the retina it has been shown that AAV2 and AAV8 capsids containing surface-exposed tyrosine-to-phenylalanine (Y-F) mutations display increased retinal transduction relative to the unmodified capsid.

AAV44.9 has high gene transfer activity in a number of cell types given the inclusion of additional serine residues in variable domain 3 of capsid protein VP1 of AAV44.9 relative to capsid protein VP1 of AAVrh.8. A capsid protein VP1 of AAV44.9 with a substitution of the serine at position 470 with an asparagine is disclosed in WO 2016/183297. When the analogous serine residue was altered in the AAV2 capsid, it led to a substantial increase in titer of manufactured vector, though it did not alter transduction efficiency (see Aslanidi et al., High-efficiency Transduction of Human Monocyte-derived Dendritic Cells by Capsid-modified Recombinant AAV2 Vectors, *Vaccine,* 30(26): 3908-3917 (2012). Still, it is believed that an S470R substitution in AAV44.9 alters the transduction and binding affinity of the AAV44.9 capsid.

The inventors of the present disclosure used a rational design approach to engineer a new variant by mutagenizing the glutamic acid at residue 531 to aspartic acid. This new serotype variant, AAV44.9(E531D), was evaluated in subretinally injected mice and macaque. Amino acid substitutions at positions corresponding to the E530 position in the AAV2 capsid, such as position 531 in AAVrh.8 and AAV44.9, have been hypothesized to alter transduction efficiency. See International Patent Publication No. WO 2018/156654, published on Aug. 30, 2018, the contents of which are incorporated by reference herein.

As described herein, rAAV particles incorporating the AAV44.9(E531D) capsid variant were surprisingly found to be capable of highly efficient transduction of rods, cones, and retinal pigment epithelium ("RPE") following subretinal injection. In addition, AAV44.9(E531D) exhibits increased lateral spread, transducing photoreceptors and retinal pigment epithelium outside the subretinal injection bleb. The increased potency and lateral spread of AAV44.9(E531D) make this variant a promising vector for gene therapies targeted to the retina.

Subretinal injection under the cone-rich fovea has been shown to promote loss of central retinal thickness as well as loss of visual acuity in some treated patients (Phase I/II trials for RPE65-LCA2). See Jacobson et al., *Arch Ophthalmol.* 2012; 130(1):9-24. However, subretinal injections in extrafoveal retina were well tolerated. It may be advantageous, therefore, to use a vector that effectively targeted foveal cones following extrafoveal subretinal injection, i.e., fovea not detached during surgery. Vectors being used currently in clinical trials for Achromatopsia and other inherited retinal diseases do not meet this criteria. Transduction of retina to the site of injection is a desirable feature of newer generation AAV vectors, as transgene expression beyond the initial boundary of the subretinal bleb might avoid some of the deleterious effects of retinal detachment while maximizing the beneficial gene therapy effects. For example, in human subjects, the lateral spread of transduction could allow subretinal injection in the parafoveal region to produce transduction of the foveal cells while circumventing the deleterious effects of inducing a foveal detachment. Recently, EGFP-expressing AAV vectors exhibited lateral spread of transgene expression beyond the subretinal injection site following subretinally-delivered AAV vectors in normal dogs. See Breuwer et al., Evaluation of Lateral Spread of Transgene Expression following Subretinal AAV-Mediated Gene Delivery in Dogs, *PLoS One,* 2013; 8(4): e60218.

The parafoveal region is the zone of the eye that circumscribes the fovea, approximately 4 degrees eccentricity from the central fixation point. The parafovea has the highest density of rods, while still also containing a large number of cones. It is a transitional zone between cone- and rod-dominant retina and is important in the context of diseases where degeneration proceeds from the outer to inner retina, such as retinitis pigmentosa (RP). The perifoveal region is the zone that circumscribes the parafovea, and represents the outermost band of the macula. Like the parafovea, the periovea has an important role in progression of diseases like RP, where retinal degeration starts in the periphery and progresses to the central retina. The perifovea is the first zone of the macula to undergo degeneration in RP.

Aspects of this disclosure relate to rAAV particles and vectors comprising a modified AAV44.9 capsid for treatment of the eye. In particular, this disclosure provides, in some embodiments, particles comprising an AAV44.9 capsid having an E531D mutation for treatment of retinal disorders. In some embodiments, the disclosure provides particles comprising an AAV44.9(E531D) capsid that exhibits enhanced lateral spread after subretinal injection to the fovea, wherein detachment of the fovea is minimized. In some embodiments, the disclosure provides a capsid protein, e.g., a VP1, VP2 or VP3 capsid protein, comprising the amino acid sequence of any one of SEQ ID NO: 1, 2 or 3, respectively.

In some embodiments, the disclosure provides rAAV particles comprising a capsid comprising a VP1, VP2, and/or VP3 protein, wherein the rAAV particle further comprises a polynucleotide comprising a heterologous nucleic acid sequence.

In some embodiments, the heterologous nucleic acid sequence in the rAAV particle encodes a diagnostic or therapeutic agent, e.g., a polypeptide, a peptide, a ribozyme, a peptide nucleic acid, an siRNA, an RNAi, a guide RNA, an antisense oligonucleotide, an antisense polynucleotide, an antibody, an antigen binding fragment, or any combination thereof.

In particular embodiments, the therapeutic agent a) preserves one or more photoreceptor (PR) cells or one or more retinal pigment epithelium ("RPE") cells, b) restores one or more rod- and/or cone-mediated functions, c) restores completely or partially visual behavior in one or both eyes, or d) any combination thereof. In some embodiments, production of the therapeutic agent persists in the one or more photoreceptor cells or the one or more RPE cells substantially for a period of at least three months following an initial administration of the rAAV particle into the one or both eyes of the mammal.

In some embodiments, the heterologous nucleic acid sequence comprises a sequence (e.g., a sequence having at least 80% identity to a target coding sequence) associated with a disease, disorder, or condition, such as dominant cone dystrophy, dominant cone-rod dystrophy, Leber's congenital amaurosis, recessive cone dystrophy, recessive cone-rod dystrophy, macular dystrophy, pattern dystrophy, vitelliform dystrophy, central choroidal dystrophy, Stargardt disease, austomal dominant, autosomal recessive and X-linked retinitis pigmentosa, retinitis pigmentosa associated with Bardet-Biedl syndrome, X-linked juvenile retinoschisis, achromatopsia, blue cone monochromacy, and Usher syndrome types I, II and III. In some embodiments, the heterologous nucleic acid sequence (e.g., a sequence having at least 80% identity to a target coding sequence) comprises a sequence associated with a disease, disorder, or condition, such as Duchenne Muscular Dystrophy, Limb Girdle Muscular Dystrophy, Spinal Muscular Atrophy, Pompe Disease, Friedrich's Ataxia, Mucopolysaccharidosis (MPS) (all forms), Lysosomal Storage Diseases (LSD) (all forms), Amyotrophic lateral sclerosis (ALS), Parkinson's disease, and Alzheimer's disease.

In some embodiments, the heterologous nucleic acid sequence has at least 80% identity to a target coding sequence. In some embodiments, the heterologous nucleic acid sequence has at least 95% identity to a target coding sequence. In some embodiments, the heterologous nucleic acid sequence has at least 98% or at least 99% identity to a target coding sequence. In some embodiments, the heterologous nucleic acid sequence has 100% identity to a target coding sequence. In some embodiments, the heterologous nucleic acid sequence comprises a GUCY2D sequence.

In some embodiments, the heterologous nucleic acid sequence is a replacement coding sequence. In particular embodiments, a replacement coding sequence is administered to the subject to provide a functional protein, e.g., GUCY2D, to restore, e.g., completely or partially, photoreceptor function to a subject (e.g., a human). In some embodiments, one or both alleles of a target coding sequence of the subject are silenced by administering an rAAV particle comprising a heterologous nucleic acid sequence disclosed herein to the subject (e.g., to a human having dominant cone-rod dystrophy).

Exemplary target coding sequences include GUCY2D and Gucy2e, which are associated with dominant cone dystrophy, dominant cone-rod dystrophy and Leber's congenital amaurosis; SPATA7, which is associated with Leber's congenital amaurosis; PRPH2, which is associated with Leber's congenital amaurosis and autosomal dominant retinal diseases (e.g., retinitis pigmentosa, pattern dystrophy, vitelliform dystrophy, central choroidal dystrophy, and macular dystrophy). GUCY2D encodes the retinal guanylyl cyclase 1 (retGC1) enzyme, also known as guanylate cyclase 2D. Mutations in this gene result in Leber's congenital amaurosis and cone-rod dystrophy-6 disorders. Gucy2e encodes guanylate cyclase 2E, the murine homologue of GUCY2D.

Additional target coding sequences may comprise AIPL1, LCA5, RPGRIP1, CRX, CRB1, NMNAT1, CEP290, IMPDH1, RD3, RDH12, TULP1, KCNJ13, GDF6, and IQCB1 (all associated with Leber's congenital amaurosis); BBS1, BBS2, ARL6/BBS3, BBS4, BBS5, BBS7, TTC8/BBS8, BBS10, TRIM32/BBS11, BBS12, CCDCC28B, CEP290, TMEM67, MKS1 and MKKS (all associated with Bardet-Biedl syndrome (BBS)); RHO, PRPF31, RP1, NRL and NR2E3 (all associated with autosomal dominant retinitis pigmentosa); RPGR and RP2 (both associated with X-linked retinitis pigmentosa); PDE6A, PDE6B, PDE6G, RP25, CNGA1, CNGB1 and MAK (all associated with autosomal recessive retinitis pigmentosa); RS1 (associated with X-linked juvenile retinoschisis (XLRS)); CNGB3, CNGA3 and GNAT2 (all associated with achromatopsia); OPN1LW and OPN1MW (both associated with blue cone monochromacy (BCM); CRX, GUCA1A (GCAP1) and GUCA1B (GCAP2) (all associated with dominant cone dystrophy and dominant cone-rod dystrophy); ABCA4 (associated with recessive cone dystrophy, recessive cone-rod dystrophy, macular dystrophy and Stargardt disease); PROM1 and ELOVL4 (both associated with Stargardt disease); MYO7A, USH1C, CDH23, PCDH15 and USH1G (all associated with Usher syndrome type I); USH2A and DFNB31 (both associated with Usher syndrome type II); and CLRN1 (associated with Usher syndrome type III).

In some embodiments, the heterologous nucleic acid sequence comprises a target genomic regulatory sequence (e.g., a locus control region) associated with a disease, disorder, or condition, such as blue cone monochromacy. An exemplary target regulatory sequence is the locus control region of L/M opsin, which is associated with blue cone monochromacy.

In some aspects, the disclosure provides a composition comprising a rAAV particle and a pharmaceutically acceptable carrier, excipient, diluent and/or buffer.

In some aspects, the disclosure provides a method of transducing RPE and photoreceptor cells to modulate expression of a heterologous nucleic acid sequence (or transgene) in a subject, the method comprising administering to the subject, such as a human subject, a composition comprising an rAAV particle as described herein and a pharmaceutically acceptable carrier, excipient, diluent and/or buffer. In some aspects, the disclosure provides a method of treating retinal disease in a subject, the method comprising administering a composition to the eye of a subject.

In some aspects, the disclosure provides a composition for use in treating retinal disease and a composition for use in the manufacture of a medicament to treat retinal disease. In some aspects, the disclosure provides a composition comprising an rAAV particle as described herein for use in treatment by subretinally or intravitreally administering to one or both eyes of the mammal.

In some aspects, the disclosure provides a method for expressing a nucleic acid segment in one or more photoreceptor cells or RPE cells of a mammal, the method comprising: subretinally or intravitreally administering to one or both eyes of the mammal an rAAV particle as described herein, wherein the rAAV particle comprises a polynucleotide comprising at least a first polynucleotide that comprises a PR- or an RPE-cell-specific promoter operably linked to at least a first heterologous nucleic acid sequence that encodes a therapeutic agent, for a time effective to produce the therapeutic agent in the one or more PR cells or RPE cells of the mammal.

The rAAV particle may comprise multiple (two, three, four, five, six, seven, eight, nine, or ten) heterologous nucleic acid sequences. In certain embodiments, the multiple heterologous nucleic acid sequences are comprised on a single polynucleotide molecule. Multiple heterologous nucleic acid sequences may be used, for example, to correct or ameliorate a gene defect caused by a multi-subunit protein. In various embodiments, a different heterologous nucleic acid sequence may be used to encode each subunit of a protein, or to encode different peptides or proteins. This is desirable when the size of the nucleic acid encoding the protein subunit is large, e.g., for an immunoglobulin, the platelet-derived growth factor, or a dystrophin protein. In order for the cell to produce the multi-subunit protein, a cell is infected with the rAAV particle containing each of the different subunits. Alternatively, different subunits of a protein may be encoded by the same nucleic acid sequence. In various embodiments, a single heterologous nucleic acid sequence includes the nucleic acid encoding each of the subunits, with the nucleic acid for each subunit separated by an internal ribozyme entry site (IRES). This is desirable when the size of the nucleic acid encoding each of the subunits is small, e.g., the total size of the nucleic acid encoding the subunits and the IRES is less than five kilobases.

As an alternative to an IRES, the nucleic acid may be separated by sequences encoding a 2A peptide, which self-cleaves in a post-translational event. This 2A peptide is significantly smaller than an IRES, making it well suited for use when space is a limiting factor. More often, when the heterologous nucleic acid sequence is large, consists of multi-subunits, or two heterologous nucleic acid sequences are co-delivered, or rAAV particle carrying the desired heterologous nucleic acid sequence(s) or subunits are co-administered to allow them to concatamerize in vivo to form a single vector genome. In such an embodiment, a first rAAV particle may carry an expression cassette which expresses a single heterologous nucleic acid sequence and a second rAAV particle may carry an expression cassette which expresses a different heterologous nucleic acid sequence for co-expression in the host cell. However, the selected heterologous nucleic acid sequence may encode any biologically active product or other product, e.g., a product desirable for study.

In some embodiments, the polynucleotide within the rAAV particle comprises regulatory sequences, such as transcription and translation initiation and termination codons, which are specific to the type of host (e.g., bacterium, fungus, plant, or animal) into which the rAAV particle is to be introduced. Preferably, the nucleic acid molecule within the rAAV particle comprises regulatory sequences that are specific to the genus of the host. Most preferably, the molecule comprises regulatory sequences that are specific to the species of the host.

The polynucleotide within the rAAV particle preferably comprises expression control sequences, such as promoters, enhancers, polyadenylation signals, transcription terminators, internal ribosome entry sites (IRES), and the like, that provide for the expression of the heterologous nucleic acid sequence(s) in a host cell. Exemplary expression control sequences are known in the art and described in, for example, Goeddel, *Gene Expression Technology: Methods in Enzymology*, Vol. 185, Academic Press, San Diego, CA. (1990).

BRIEF DESCRIPTION OF THE DRAWINGS

The following drawings form part of the present specification and are included to demonstrate certain aspects of the present invention. The invention may be better understood by reference to the following description taken in conjunction with the accompanying drawings, in which like reference numerals identify like elements, and in which:

FIG. 2A shows fundus images at exposure long 25. FIGS. 2B-2D shows flow-cytometry scatter plots and FIG. 2E shows quantitative analysis showing that AAV44.9 transduced rod more efficiently than AAV5 and AAV8 (Y733F) following subretinal injection with $2 \times 10^9$ vector genomes (vg).

FIGS. 4A, 4B, and 4C show qualitative and quantitative analysis of the AAV44.9(Y733F) and AAV44.9(E531D). FIG. 4A shows fundus images at exposure long 25, FIG. 4B shows flow-cytometry scatter plots, and FIG. 4C shows quantitative analysis by showing that AAV44.9(E531D) transduced rod cells more efficiently than AAV44.9 and AAV44.9(Y733F) following subretinal injection with $2 \times 10^9$ vg.

FIGS. 5A and 5B show representative retinal cross section images showing mCherry expression primarily in photoreceptors and RPE in Nrl-GFP mouse retina injected with AAV44.9(Y733F) (upper panel, FIG. 5A) and AAV44.9 (E531D) (upper panel, FIG. 5B) at 4 weeks after subretinal injection. The lower panels of FIGS. 5A and 5B show overlapped images of nuclear DAPI stain (blue), endogenous GFP (green) expression in rod cells and mCherry expression (red) in photoreceptor cells.

FIG. 7A shows fundus images of AAV2, AAV5, AAV8 (Y733F), AAV44.9, AAV44.9(Y733F) and AAV44.9(E531D) (at long 25 integration), (FIG. 7B shows fundus images (at long 100 integration) variants at 4 weeks of intravitreal injection with $2 \times 10^9$ vg.

FIG. 8A shows GFP expression in cone cells at 4 weeks after SR injection. FIGS. 8B and 8C show co-staining with cone-arrestin antibody colocalizes with GFP fluorescence.

GUCY2e or AAV8 (Y733F)-hGRK1-GUCY2e. FIG. 18A shows the average maximum a- and b-wave amplitudes under both scotopic (left) and photopic (right) settings. FIG. 18B shows the representative ERG traces of cones from eyes treated with vector, or contralateral untreated ("no Tx") eye.

DETAILED DESCRIPTION

Figure 1:
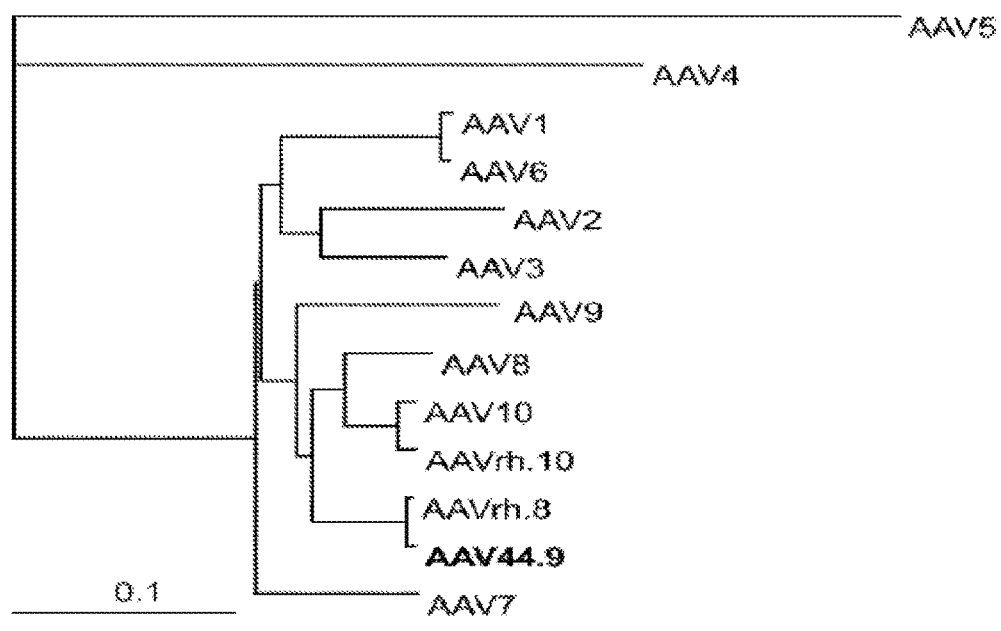
FIG. 1 shows AAV phylogeny based on VP1 (AAV44.9 shown in bold) and a table with details of the AAV constructs for vector production.

The present disclosure provides AAV44.9(E531D), a novel variant of the capsid serotype AAV44.9, and the evaluation of the performance of vectors and particles incorporating this plasmid in subretinally injected mice and macaques relative to benchmark vectors, the closely related AAVrh.8, and unmodified AAV44.9. As described herein, it was found that AAV44.9(E531D) mediates higher retinal transduction relative to unmodified AAV44.9 and AAVrh.8, and significantly higher transduction than benchmark capsids (e.g., AAV5- and AAV8-based vectors) in both species.

Accordingly, the disclosure provides rAAV particles comprising capsid proteins of AAV44.9(E531D) and related compositions and methods. In some embodiments, the rAAV particle comprises a heterologous nucleic acid sequence, e.g., encoding a therapeutic or diagnostic agent. The heterologous nucleic acid sequence may be in the form of a single-stranded (ss) or self-complementary (sc) AAV nucleic acid vector, such as single-stranded or self-complementary recombinant viral genome.

The disclosure further provides rAAV particles comprising capsid proteins of AAV44.9(Y733F) and related compositions and methods. This AAV44.9 capsid variant has a Y-F mutation at residue 733. In some embodiments, the rAAV particle comprises a heterologous nucleic acid sequence, e.g., encoding a therapeutic or diagnostic agent. The heterologous nucleic acid sequence may be in the form of a single-stranded (ss) or self-complementary (sc) AAV nucleic acid vector, such as single-stranded or self-complementary recombinant viral genome.

Aspects of this disclosure relate to vectors comprising an AAV44.9(E531D) capsid that exhibits enhanced lateral spread after subretinal injection to the fovea, wherein detachment of the fovea (e.g., a temporary bullous detachment) is minimized. In some embodiments, the disclosure provides a capsid protein, e.g., a VP1, VP2 or VP3 capsid protein, comprising the amino acid sequence of SEQ ID NO: 1, 2 or 3.

In some embodiments, the disclosure provides an rAAV particle comprising a capsid comprising a VP1, VP2, and/or VP3 protein, wherein the rAAV particle further comprises a polynucleotide comprising a heterologous nucleic acid sequence. In some embodiments, the rAAV particle comprises a capsid comprising a VP1, VP2, and/or VP3 protein, wherein the VP1 protein comprises the amino acid sequence of SEQ ID NO: 1, the VP2 protein comprises the amino acid sequence of SEQ ID NO: 2, and/or the VP3 protein comprises the amino acid sequence of SEQ ID NO: 3, and wherein the AAV further comprises a polynucleotide comprising a heterologous nucleic acid sequence. The heterologous nucleic acid sequence may be flanked by one or more inverted terminal repeat (ITR) sequences.

In some embodiments, the disclosure provides a capsid protein comprising the amino acid sequence of SEQ ID NO: 1, 2, and/or 3.

In some embodiments, the disclosure provides a nucleic acid, e.g., a plasmid or viral vector, comprising the nucleic acid sequence of SEQ ID NO: 4 (which encodes AAV44.9 (E531D) VP1). In some embodiments, the disclosure provides a nucleic acid, e.g., a plasmid or viral vector, comprising the nucleic acid sequence of SEQ ID NO: 5 (which encodes AAV44.9(E531D) VP2). In some embodiments, the disclosure provides a nucleic acid, e.g., a plasmid or viral vector, comprising the nucleic acid sequence of SEQ ID NO: 6 (which encodes AAV44.9(E531D) VP3). In some embodiments, the viral vector is a recombinant adeno-associated viral (rAAV) vector. In some embodiments, the rAAV vector is self-complementary. In some embodiments, the nucleic acid is comprised within a cell, e.g., a mammalian or insect cell.

The sequences of SEQ ID NOs: 1-8 are provided below.

```
AAV44.9(E531D) VP1 amino acid sequence
                                   SEQ ID NO: 1
MAADGYLPDWLEDNLSEGIREWWDLKPGAPKPKANQQKQDDGRGLVLPGY

KYLGPFNGLDKGEPVNAADAAALEHDKAYDQQLKAGDNPYLRYNHADAEF

QERLQEDTSFGGNLGRAVFQAKKRVLEPLGLVEEGAKTAPGKKRPVEQSP

QEPDSSSGIGKTGQQPAKKRLNFGQTGDTESVPDPQPLGEPPAAPSGLGP

NTMASGGGAPMADNNEGADGVGNSSGNWHCDSTWLGDRVITTSTRTWALP

TYNNHLYKQISNGTSGGSTNDNTYFGYSTPWGYFDFNRFHCHFSPRDWQR

LINNNWGFRPKRLNFKLFNIQVKEVTTNEGTKTIANNLTSTVQVFTDSEY

QLPYVLGSAHQGCLPPFPADVFMVPQYGYLTLNNGSQALGRSSFYCLEYF

PSQMLRTGNNFQFSYTFEDVPFHSSYAHSQSLDRLMNPLIDQYLYYLVRT

QTTGTGGTQTLAFSQAGPSSMASQARNWVPGPSYRQQRVSTTTNQNNNSN

FAWTGAAKFKLNGRDSLMNPGVAMASHKDDDDRFFPSSGVLIFGKQGAGN

DGVDYSQVLITDEEEIKATNPVATEEYGAVAINNQAANTQAQTGLVHNQG

VIPGMVWQNRDVYLQGPIWAKIPHTDGNFHPSPLMGGFGLKHPPPQILIK

NTPVPADPPLTFNQAKLNSFITQYSTGQVSVEIEWELQKENSKRWNPEIQ

YTSNYYKSTNVDFAVNTEGVYSEPRPIGTRYLTRNL

AAV44.9(E531D) VP2 amino acid sequence
                                   SEQ ID NO: 2
MAPGKKRPVEQSPQEPDSSSGIGKTGQQPAKKRLNFGQTGDTESVPDPQP

LGEPPAAPSGLGPNTMASGGGAPMADNNEGADGVGNSSGNWHCDSTWLGD

RVITTSTRTWALPTYNNHLYKQISNGTSGGSTNDNTYFGYSTPWGYFDFN

RFHCHFSPRDWQRLINNNWGFRPKRLNFKLFNIQVKEVTTNEGTKTIANN

LTSTVQVFTDSEYQLPYVLGSAHQGCLPPFPADVFMVPQYGYLTLNNGSQ

ALGRSSFYCLEYFPSQMLRTGNNFQFSYTFEDVPFHSSYAHSQSLDRLMN
```

```
                   -continued
PLIDQYLYYLVRTQTTGTGGTQTLAFSQAGPSSMASQARNWVPGPSYRQQ

RVSTTTNQNNNSNFAWTGAAKFKLNGRDSLMNPGVAMASHKDDDDRFFPS

SGVLIFGKQGAGNDGVDYSQVLITDEEEIKATNPVATEEYGAVAININQA

ANTQAQTGLVHNQGVIPGMVWQNRDVYLQGPIWAKIPHTDGNFHPSPLMG

GFGLKHPPPQILIKNTPVPADPPLTFNQAKLNSFITQYSTGQVSVEIEWE

LQKENSKRWNPEIQYTSNYYKSTNVDFAVNTEGVYSEPRPIGTRYLTRNL

AAV44.9(E531D) VP3 amino acid sequence
                                   SEQ ID NO: 3
MASGGGAPMADNNEGADGVGNSSGNWHCDSTWLGDRVITTSTRTWALPTY

NNHLYKQISNGTSGGSTNDNTYFGYSTPWGYFDFNRFHCHFSPRDWQRLI

NNNWGFRPKRLNFKLFNIQVKEVTTNEGTKTIANNLTSTVQVFTDSEYQL

PYVLGSAHQGCLPPFPADVFMVPQYGYLTLNNGSQALGRSSFYCLEYFPS

QMLRTGNNFQFSYTFEDVPFHSSYAHSQSLDRLMNPLIDQYLYYLVRTQT

TGTGGTQTLAFSQAGPSSMASQARNWVPGPSYRQQRVSTTTNQNNNSNFA

WTGAAKFKLNGRDSLMNPGVAMASHKDDDDRFFPSSGVLIFGKQGAGNDG

VDYSQVLITDEEEIKATNPVATEEYGAVAINNQAANTQAQTGLVHNQGVI

PGMVWQNRDVYLQGPIWAKIPHTDGNFHPSPLMGGFGLKHPPPQILIKNT

PVPADPPLTFNQAKLNSFITQYSTGQVSVEIEWELQKENSKRWNPEIQYT

SNYYKSTNVDFAVNTEGVYSEPRPIGTRYLTRNL

AAV44.9(E531D) VP1 nucleic acid sequence
                                   SEQ ID NO: 4
ATGGCTGCCGATGGTTATCTTCCAGATTGGCTCGAGGACAACCTCTCTGA

GGGCATTCGCGAGTGGTGGGACTTGAAACCTGGAGCCCCGAAACCCAAAG

CCAACCAGCAAAAGCAGGACGACGGCCGGGGTCTGGTGCTTCCTGGCTAC

AAGTACCTCGGACCCTTCAACGGGACTCGACAAGGGGGAGCCCGTCAACGC

GGCGGACGCAGCGGCCCTCGAGCACGACAAGGCCTACGACCAGCAGCTCA

AAGCGGGTGACAATCCGTACCTGCGGTATAACCACGCCGACGCCGAGTTT

CAGGAGCGTCTGCAAGAAGATACGTCTTTTGGGGGCAACCTCGGGCGAGC

AGTCTTCCAGGCCAAGAAGCGGGTTCTCGAACCTCTCGGTCTGGTTGAGG

AAGGCGCTAAGACGGCTCCTGGAAAGAAGAGACCGGTAGAGCAGTCACCC

CAAGAACCAGACTCCTCATCGGGCATCGGCAAGACAGGCCAGCAGCCCGC

TAAAAAGAGACTCAATTTTGGTCAGACTGGCGACACAGAGTCAGTCCCCG

ACCCACAACCTCTCGGAGAACCTCCAGCAGCCCCCTCAGGTCTGGGACCT

AATACAATGGCTTCAGGCGGTGGCGCTCCAATGCAGACAATAACGAAGG

CGCCGACGGAGTGGGTAATTCCTCGGGAAATTGGCATTGCGATTCCACAT

GGCTGGGGGACAGAGTCATCACCACCAGCACCCGAACCTGGGCCCTGCCC

ACCTACAACAACCACCTCTACAAGCAAATCTCCAACGGCACCTCGGGAGG

AAGCACCAACGACAACACCTACTTTGGCTACAGCACCCCCTGGGGGTATT

TTGACTTCAACAGATTCCACTGCCACTTTTCACCACGTGACTGGCAGCGA

CTCATCAACAACAATTGGGGATTCCGGCCCAAGAGACTCAACTTCAAGCT

CTTCAACATCCAGGTCAAGGAAGTCACGACGAACGAAGGCACCAAGACCA

TCGCCAATAATCTCACCAGCACCGTGCAGGTCTTTACGGACTCGGAGTAC

CAGCTACCGTACGTGCTAGGATCAGCTCACCAGGGATGTCTGCCTCCGTT
```

CCCGGCGGACGTCTTCATGGTTCCTCAGTACGGTTATCTAACTCTGAACA

ATGGCAGCCAGGCCCTGGGACGTTCCTCCTTCTACTGCCTGGAGTATTTC

CCATCGCAGATGCTGAGAACCGGCAACAACTTTCAGTTCAGCTACACCTT

CGAGGACGTGCCTTTCCACAGCAGCTACGCGCACAGCCAAAGCCTGGACA

GGCTGATGAATCCCCTCATCGACCAGTACCTGTATTACCTGGTCAGAACG

CAGACAACCGGGACTGGAGGGACGCAGACTCTGGCATTCAGCCAAGCAGG

CCCTAGCTCAATGGCCAGCCAGGCTAGAAACTGGGTGCCCGGACCGAGCT

ACCGGCAGCAGCGCGTCTCCACGACAACCAACCAGAACAACAACAGCAAC

TTTGCCTGGACGGGAGCTGCCAAATTTAAACTGAACGGCCGAGACTCTCT

AATGAACCCCGGCGTGGCCATGGCTTCACACAAGGATGACGATGACCGGT

TCTTCCCTTCTAGCGGGGTCCTGATTTTCGGCAAGCAAGGAGCCGGGAAT

GATGGAGTGGATTACAGCCAAGTGCTGATTACAGATGAGGAAGAAATCAA

GGCTACCAACCCCGTGGCAACAGAGGAATATGGAGCAGTGGCCATCAACA

ACCAGGCCGCTAATACGCAGGCGCAGACCGGACTCGTGCACAACCAGGGG

GTGATTCCCGGCATGGTGTGGCAGAACAGAGACGTGTACCTGCAGGGTCC

CATCTGGGCCAAAATTCCTCACACGGACGGCAACTTTCACCCGTCTCCCC

TGATGGGCGGCTTTGGACTGAAGCACCCGCCTCCTCAAATTCTCATCAAG

AACACACCGGTTCCAGCGGACCCGCCGCTTACCTTCAACCAGGCCAAGCT

GAACTCTTTCATCACGCAGTACAGCACCGGACAGGTCAGCGTGGAAATCG

AGTGGGAGCTGCAGAAAGAAAACAGCAAACGCTGGAATCCAGAGATTCAG

TACACTTCCAACTACTACAAATCTACAAATGTGGACTTTGCTGTCAACAC

GGAAGGAGTGTATAGCGAGCCTCGCCCCATTGGCACGCGCTACCTCACCC

GTAATCTGTAA

AAV44.9(E531D) VP2 nucleic acid sequence

SEQ ID NO: 5

ACGGCTCCTGGAAAGAAGAGACCGGTAGAGCAGTCACCCCAAGAACCAGA

CTCCTCATCGGGCATCGGCAAGACAGGCCAGCAGCCCGCTAAAAAGAGAC

TCAATTTTGGTCAGACTGGCGACACAGAGTCAGTCCCCGACCCACAACCT

CTCGGAGAACCTCCAGCAGCCCCTCAGGTCTGGGACCTAATACAATGGC

TTCAGGCGGTGGCGCTCCAATGGCAGACAATAACGAAGGCGCCGACGGAG

TGGGTAATTCCTCGGGAAATTGGCATTGCGATTCCACATGGCTGGGGGAC

AGAGTCATCACCACCAGCACCCGAACCTGGGCCCTGCCCACCTACAACAA

CCACCTCTACAAGCAAATCTCCAACGGCACCTCGGGAGGAAGCACCAACG

ACAACACCTACTTTGGCTACAGCACCCCCTGGGGGTATTTTGACTTCAAC

AGATTCCACTGCCACTTTTCACCACGTGACTGGCAGCGACTCATCAACAA

CAATTGGGGATTCCGGCCCAAGAGACTCAACTTCAAGCTCTTCAACATCC

AGGTCAAGGAAGTCACGACGAACGAAGGCACCAAGACCATCGCCAATAAT

CTCACCAGCACCGTGCAGGTCTTTACGGACTCGGAGTACCAGCTACCGTA

CGTGCTAGGATCAGCTCACCAGGGATGTCTGCCTCCGTTCCCGGCGGACG

TCTTCATGGTTCCTCAGTACGGTTATCTAACTCTGAACAATGGCAGCCAG

GCCCTGGGACGTTCCTCCTTCTACTGCCTGGAGTATTTCCCATCGCAGAT

GCTGAGAACCGGCAACAACTTTCAGTTCAGCTACACCTTCGAGGACGTGC

CTTTCCACAGCAGCTACGCGCACAGCCAAAGCCTGGACAGGCTGATGAAT

CCCCTCATCGACCAGTACCTGTATTACCTGGTCAGAACGCAGACAACCGG

GACTGGAGGGACGCAGACTCTGGCATTCAGCCAAGCAGGCCCTAGCTCAA

TGGCCAGCCAGGCTAGAAACTGGGTGCCCGGACCGAGCTACCGGCAGCAG

CGCGTCTCCACGACAACCAACCAGAACAACAACAGCAACTTTGCCTGGAC

GGGAGCTGCCAAATTTAAACTGAACGGCCGAGACTCTCTAATGAACCCCG

GCGTGGCCATGGCTTCACACAAGGATGACGATGACCGGTTCTTCCCTTCT

AGCGGGGTCCTGATTTTCGGCAAGCAAGGAGCCGGGAATGATGGAGTGGA

TTACAGCCAAGTGCTGATTACAGATGAGGAAGAAATCAAGGCTACCAACC

CCGTGGCAACAGAGGAATATGGAGCAGTGGCCATCAACAACCAGGCCGCT

AATACGCAGGCGCAGACCGGACTCGTGCACAACCAGGGGGTGATTCCCGG

CATGGTGTGGCAGAACAGAGACGTGTACCTGCAGGGTCCCATCTGGGCCA

AAATTCCTCACACGGACGGCAACTTTCACCCGTCTCCCCTGATGGGCGGC

TTTGGACTGAAGCACCCGCCTCCTCAAATTCTCATCAAGAACACACCGGT

TCCAGCGGACCCGCCGCTTACCTTCAACCAGGCCAAGCTGAACTCTTTCA

TCACGCAGTACAGCACCGGACAGGTCAGCGTGGAAATCGAGTGGGAGCTG

CAGAAAGAAAACAGCAAACGCTGGAATCCAGAGATTCAGTACACTTCCAA

CTACTACAAATCTACAAATGTGGACTTTGCTGTCAACACGGAAGGAGTGT

ATAGCGAGCCTCGCCCCATTGGCACGCGCTACCTCACCCGTAATCTGTAA

AAV44.9(E531D) VP3 nucleic acid sequence

SEQ ID NO: 6

ATGGCTTCAGGCGGTGGCGCTCCAATGGCAGACAATAACGAAGGCGCCGA

CGGAGTGGGTAATTCCTCGGGAAATTGGCATTGCGATTCCACATGGCTGG

GGGACAGAGTCATCACCACCAGCACCCGAACCTGGGCCCTGCCCACCTAC

AACAACCACCTCTACAAGCAAATCTCCAACGGCACCTCGGGAGGAAGCAC

CAACGACAACACCTACTTTGGCTACAGCACCCCCTGGGGGTATTTTGACT

TCAACAGATTCCACTGCCACTTTTCACCACGTGACTGGCAGCGACTCATC

AACAACAATTGGGGATTCCGGCCCAAGAGACTCAACTTCAAGCTCTTCAA

CATCCAGGTCAAGGAAGTCACGACGAACGAAGGCACCAAGACCATCGCCA

ATAATCTCACCAGCACCGTGCAGGTCTTTACGGACTCGGAGTACCAGCTA

CCGTACGTGCTAGGATCAGCTCACCAGGGATGTCTGCCTCCGTTCCCGGC

GGACGTCTTCATGGTTCCTCAGTACGGTTATCTAACTCTGAACAATGGCA

GCCAGGCCCTGGGACGTTCCTCCTTCTACTGCCTGGAGTATTTCCCATCG

CAGATGCTGAGAACCGGCAACAACTTTCAGTTCAGCTACACCTTCGAGGA

CGTGCCTTTCCACAGCAGCTACGCGCACAGCCAAAGCCTGGACAGGCTGA

TGAATCCCCTCATCGACCAGTACCTGTATTACCTGGTCAGAACGCAGACA

ACCGGGACTGGAGGGACGCAGACTCTGGCATTCAGCCAAGCAGGCCCTAG

CTCAATGGCCAGCCAGGCTAGAAACTGGGTGCCCGGACCGAGCTACCGGC

AGCAGCGCGTCTCCACGACAACCAACCAGAACAACAACAGCAACTTTGCC

TGGACGGGAGCTGCCAAATTTAAACTGAACGGCCGAGACTCTCTAATGAA

CCCCGGCGTGGCCATGGCTTCACACAAGGATGACGATGACCGGTTCTTCC

-continued

CTTCTAGCGGGGTCCTGATTTTCGGCAAGCAAGGAGCCGGGAATGATGGA

GTGGATTACAGCCAAGTGCTGATTACAGATGAGGAAGAAATCAAGGCTAC

CAACCCCGTGGCAACAGAGGAATATGGAGCAGTGGCCATCAACAACCAGG

CCGCTAATACGCAGGCGCAGACCGGACTCGTGCACAACCAGGGGGTGATT

CCCGGCATGGTGTGGCAGAACAGAGACGTGTACCTGCAGGGTCCCATCTG

GGCCAAAATTCCTCACACGGACGGCAACTTTCACCCGTCTCCCCTGATGG

GCGGCTTTGGACTGAAGCACCCGCCTCCTCAAATTCTCATCAAGAACACA

CCGGTTCCAGCGGACCCGCCGCTTACCTTCAACCAGGCCAAGCTGAACTC

TTTCATCACGCAGTACAGCACCGGACAGGTCAGCGTGGAAATCGAGTGGG

AGCTGCAGAAAGAAACAGCAAACGCTGGAATCCAGAGATTCAGTACACT

TCCAACTACTACAAATCTACAAATGTGGACTTTGCTGTCAACACGGAAGG

AGTGTATAGCGAGCCTCGCCCCATTGGCACGCGCTACCTCACCCGTAATC

TGTAA

AAV44.9 wildtype VP1 amino acid sequence

SEQ ID NO: 7

MAADGYLPDWLEDNLSEGIREWWDLKPGAPKPKANQQKQDDGRGLVLPGY

KYLGPFNGLDKGEPVNAADAAALEHDKAYDQQLKAGDNPYLRYNHADAEF

QERLQEDTSFGGNLGRAVFQAKKRVLEPLGLVEEGAKTAPGKKRPVEQSP

QEPDSSSGIGKTGQQPAKKRLNFGQTGDTESVPDPQPLGEPPAAPSGLGP

NTMASGGGAPMADNNEGADGVGNSSGNWHCDSTWLGDRVITTSTRTWALP

TYNNHLYKQISNGTSGGSTNDNTYFGYSTPWGYFDFNRFHCHFSPRDWQR

LINNNWGFRPKRLNFKLFNIQVKEVTTNEGTKTIANNLTSTVQVFTDSEY

QLPYVLGSAHQGCLPPFPADVFMVPQYGYLTLNNGSQALGRSSFYCLEYF

PSQMLRTGNNFQFSYTFEDVPFHSSYAHSQSLDRLMNPLIDQYLYYLVRT

QTTGTGGTQTLAFSQAGPSSMASQARNWVPGPSYRQQRVSTTTNQNNNSN

FAWTGAAKFKLNGRDSLMNPGVAMASHKDDEDRFFPSSGVLIFGKQGAGN

DGVDYSQVLITDEEEIKATNPVATEEYGAVAINNQAANTQAQTGLVHNQG

VIPGMVWQNRDVYLQGPIWAKIPHTDGNFHPSPLMGGFGLKHPPPQILIK

NTPVPADPPLTFNQAKLNSFITQYSTGQVSVEIEWELQKENSKRWNPEIQ

YTSNYYKSTNVDFAVNTEGVYSEPRPIGTRYLTRNL

AAV44.9 wildtype VP1 nucleic acid sequence

SEQ ID NO: 8

ATGGCTGCCGATGGTTATCTTCCAGATTGGCTCGAGGACAACCTCTCTGA

GGGCATTCGCGAGTGGTGGGACTTGAAACCTGGAGCCCCGAAACCCAAAG

CCAACCAGCAAAAGCAGGACGACGGCCGGGGTCTGGTGCTTCCTGGCTAC

AAGTACCTCGGACCCTTCAACGGACTCGACAAGGGGGAGCCCGTCAACGC

GGCGGACGCAGCGGCCCTCGAGCACGACAAGGCCTACGACCAGCAGCTCA

AAGCGGGTGACAATCCGTACCTGCGGTATAACCACGCCGACGCCGAGTTT

CAGGAGCGTCTGCAAGAAGATACGTCTTTTGGGGGCAACCTCGGGCGAGC

AGTCTTCCAGGCCAAGAAGCGGGTTCTCGAACCTCTCGGTCTGGTTGAGG

AAGGCGCTAAGACGGCTCCTGGAAAGAAGAGACCGGTAGAGCAGTCACCC

CAAGAACCAGACTCCTCATCGGGCATCGGCAAGACAGGCCAGCAGCCCGC

-continued

TAAAAAGAGACTCAATTTTGGTCAGACTGGCGACACAGAGTCAGTCCCCG

ACCCACAACCTCTCGGAGAACCTCCAGCAGCCCCCTCAGGTCTGGGACCT

AATACAATGGCTTCAGGCGGTGGCGCTCCAATGGCAGACAATAACGAAGG

CGCCGACGGAGTGGGTAATTCCTCGGGAAATTGGCATTGCGATTCCACAT

GGCTGGGGGACAGAGTCATCACCACCAGCACCCGAACCTGGGCCCTGCCC

ACCTACAACAACCACCTCTACAAGCAAATCTCCAACGGCACCTCGGGAGG

AAGCACCAACGACAACACCTACTTTGGCTACAGCACCCCCTGGGGGTATT

TTGACTTCAACAGATTCCACTGCCACTTTTCACCACGTGACTGGCAGCGA

CTCATCAACAACAATTGGGGATTCCGGCCCAAGAGACTCAACTTCAAGCT

CTTCAACATCCAGGTCAAGGAAGTCACGACGAACGAAGGCACCAAGACCA

TCGCCAATAATCTCACCAGCACCGTGCAGGTCTTTACGGACTCGGAGTAC

CAGCTACCGTACGTGCTAGGATCAGCTCACCAGGGATGTCTGCCTCCGTT

CCCGGCGGACGTCTTCATGGTTCCTCAGTACGGTTATCTAACTCTGAACA

ATGGCAGCCAGGCCCTGGGACGTTCCTCCTTCTACTGCCTGGAGTATTTC

CCATCGCAGATGCTGAGAACCGGCAACAACTTTCAGTTCAGCTACACCTT

CGAGGACGTGCCTTTCCACAGCAGCTACGCGCACAGCCAAAGCCTGGACA

GGCTGATGAATCCCCTCATCGACCAGTACCTGTATTACCTGGTCAGAACG

CAGACAACCGGGACTGGAGGGACGCAGACTCTGGCATTCAGCCAAGCAGG

CCCTAGCTCAATGGCCAGCCAGGCTAGAAACTGGGTGCCCGGACCGAGCT

ACCGGCAGCAGCGCGTCTCCACGACAACCAACCAGAACAACAACAGCAAC

TTTGCCTGGACGGGAGCTGCCAAATTTAAACTGAACGGCCGAGACTCTCT

AATGAACCCCGGCGTGGCCATGGCTTCACACAAGGATGACGAGGACCGCT

TCTTCCCTTCTAGCGGGGTCCTGATTTTCGGCAAGCAAGGAGCCGGGAAT

GATGGAGTGGATTACAGCCAAGTGCTGATTACAGATGAGGAAGAAATCAA

GGCTACCAACCCCGTGGCAACAGAGGAATATGGAGCAGTGGCCATCAACA

ACCAGGCCGCTAATACGCAGGCGCAGACCGGACTCGTGCACAACCAGGGG

GTGATTCCCGGCATGGTGTGGCAGAACAGAGACGTGTACCTGCAGGGTCC

CATCTGGGCCAAAATTCCTCACACGGACGGCAACTTTCACCCGTCTCCCC

TGATGGGCGGCTTTGGACTGAAGCACCCGCCTCCTCAAATTCTCATCAAG

AACACACCGGTTCCAGCGGACCCGCCGCTTACCTTCAACCAGGCCAAGCT

GAACTCTTTCATCACGCAGTACAGCACCGGACAGGTCAGCGTGGAAATCG

AGTGGGAGCTGCAGAAAGAAACAGCAAACGCTGGAATCCAGAGATTCAG

TACACTTCCAACTACTACAAATCTACAAATGTGGACTTTGCTGTCAACAC

GGAAGGAGTGTATAGCGAGCCTCGCCCCATTGGCACGCGCTACCTCACCC

GTAATCTGTAA

Methods for producing and using pseudotyped rAAV particles are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001). Methods of producing rAAV particles and heterologous nucleic acids are also known in the art and commercially available (see, e.g., Zolotukhin et al. Production and purification of serotype 1, 2, and 5 recombinant adeno-associated viral vectors. Methods 28 (2002) 158-167; and U.S.

Patent Publication Numbers US 2007/0015238 and US 2012/0322861, which are incorporated herein by reference in their entireties; and plasmids and kits available from ATCC and Cell Biolabs, Inc.). For example, a plasmid containing the heterologous nucleic acid sequence may be combined with one or more helper plasmids, e.g., that contain a rep gene (e.g., encoding Rep78, Rep68, Rep52 and Rep40) and a cap gene (encoding VP1, VP2, and VP3, including a modified VP3 region as described herein), and transfected or permanently integrated into a producer cell line such that the rAAV particle may be packaged and subsequently purified.

In some embodiments, the one or more helper plasmids include a first helper plasmid comprising a rep gene and a cap gene (e.g., encoding a rAAV capsid protein as described herein) and a second helper plasmid comprising a E1a gene, a E1b gene, a E4 gene, a E2a gene, and a VA gene. In some embodiments, the rep gene is a rep gene derived from AAV2 and the cap gene is derived from AAV44.9 and may include modifications to the gene in order to produce the modified capsid protein described herein. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG (R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, rAAV particle production method is described next. One or more helper plasmids are produced or obtained, which comprise rep and cap ORFs for the desired AAV serotype and the adenoviral VA, E2A (DBP), and E4 genes under the transcriptional control of their native promoters. The cap ORF may also comprise one or more modifications to produce a modified capsid protein as described herein. HEK293 cells (available from ATCC®) are transfected via CaPO4-mediated transfection, lipids or polymeric molecules such as Polyethylenimine (PEI) with the helper plasmid(s) and a plasmid containing a nucleic acid vector described herein. The HEK293 cells are then incubated for at least 60 hours to allow for rAAV particle production. Alternatively, in another example Sf9-based producer stable cell lines are infected with a single recombinant baculovirus containing the heterologous nucleic acid sequence. As a further alternative, in another example HEK293 or BHK cell lines are infected with a HSV containing the heterologous nucleic acid sequence and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for rAAV particle production. The rAAV particles can then be purified using any method known the art or described herein, e.g., by iodixanol step gradient, CsCl gradient, chromatography, or polyethylene glycol (PEG) precipitation.

The disclosure also contemplates host cells that comprise a particle that incorporates an AAV44.9(E531D) capsid, a nucleic acid encoding a AAV44.9(E531D) capsid or an rAAV particle as described herein. Such host cells include mammalian host cells, with human host cells being preferred, and may be isolated, e.g., in cell or tissue culture. In some embodiments, the host cell is a cell of the eye.

In some embodiments, a composition is provided which comprises an rAAV particle as described herein (e.g., comprising a AAV44.9(E531D) capsid) and optionally a pharmaceutically acceptable carrier, excipient, diluent and/or buffer. In some embodiments, the compositions described herein can be administered to a mammal (or subject) in need of treatment. In some embodiments, the subject has or is suspected of having one or more of a retinal disorder, retinal disease, or retinal dystrophy. In some embodiments, the subject has or is suspected of having one or more of the retinal conditions, diseases, and disorders disclosed herein (e.g., cone-rod dystrophy). In some embodiments, the subject has one or more endogenous mutant alleles (e.g., associated with or that cause a disease, disorder or condition of the eye or retina, such as cone-rod dystrophy).

In some embodiments, methods are provided for transducing a mammalian photoreceptor cell or retinal pigment epithelium cell, the method comprising administering to one or both eyes of a mammal the rAAV particles described herein. In particular embodiments, methods are provided for expressing a polynucleotide in one or more photoreceptor cells or RPE cells of a mammal, the method comprising subretinally or intravitreally administering to one or both eyes of the mammal the rAAV particles described herein, or compositions thereof, wherein the rAAV particle comprises a polynucleotide comprising at least a first polynucleotide that comprises a PR- or an RPE-cell-specific promoter operably linked to at least a first heterologous nucleic acid sequence that encodes a therapeutic agent, for a time effective to produce the therapeutic agent in the one or more PR cells or RPE cells of the mammal.

In particular embodiments, the disclosure provides a PR- or RPE-cell-specific promoter operably linked to at least a first heterologous nucleic acid sequence that encodes a therapeutic agent. Exemplary PR- or RPE-cell-specific promoters may comprise a) photoreceptor-specific promoters (active in rod and cone cells), e.g., IRBP promoter (hIRPB, IRBP, IRBP241), rhodopsin kinase promoter (hGRK1, GRK1, GRK, RK), and/or chimeric human Retinoschisin-IRBP enhancer (RS/IRPB); cone-specific promoters, e.g., red/green cone opsin promoter (which may comprise the 2.1 kb (PR2.1) version or 1.7 kb (PR1.7) version, see U.S. Patent Publication No. 2018/0112231, herein incorporated by reference), Cone Arrestin promoter (hCAR, CAR), chimeric IRBP enhancer-cone transducin promoter (IRBP/GNAT2, IRBPe-GNAT2); rod-specific promoters, e.g., human rhodopsin promoter (RHO, RHOP, etc.), human NRL promoter (NRL); or RPE-specific promoters such as RPE65 or Bestrophin/VMD2 (BEST1, BEST, VMD2).

In some embodiments, the promoter of any of the disclosed rAAV vectors comprises a nucleotide sequence that is at least 95%, at least 98%, at least 99%, or 100% identical the sequence of the hGRK1 promoter as set forth in SEQ ID NO: 11:

```
                                        (SEQ ID NO: 11)
GGGCCCCAGAAGCCTGGTGGTTGTTTGTCCTTCTCAGGGGAAAAGTGAGG

CGGCCCCTTGGAGGAAGGGGCCGGGCAGAATGATCTAATCGGATTCCAAG

CAGCTCAGGGGATTGTCTTTTTCTAGCACCTTCTTGCCACTCCTAAGCGT

CCTCCGTGACCCCGGCTGGGATTTAGCCTGGTGCTGTGTCAGCCCCGGTC

TCCCAGGGGCTTCCCAGTGGTCCCCAGGAACCCTCGACAGGGCCCGGTCT

CTCTCGTCCAGCAAGGGCAGGGACGGGCCACAGGCCAAGGGC
```

Accordingly, exemplary rAAV vectors described in the disclosure comprise AAV44.9(E531D)-hGRK1-GFP, AAV44.9(Y733F)-hGRK1-GFP, AAV44.9(E531D)-IRBP/GNAT2-hGFP, AAV44.9(Y733F)-IRBP/GNAT2-hGFP, AAV44.9(E531D)-hGRK1-GUCY2E, and AAV44.9(Y733F)-hGRK1-GUCY2E.

In particular embodiments, the disclosure provides constitutive promoters operably linked to at least a first polynucleotide that may comprise CMV, CBA, CB, smCBA, CBh, or EF1-alpha.

In some embodiments, methods are provided involving providing a mammal in need thereof with a therapeutically effective amount of a selected therapeutic agent, the method comprising administering to one or both eyes of the mammal, an amount of the rAAV particles described herein; and for a time effective to provide the mammal with a therapeutically-effective amount of the selected therapeutic agent.

In certain embodiments, the mammal is suspected of having, is at risk for developing, or has been diagnosed with a disease, disorder, or condition, such as, but not limited to, a disease, disorder, or condition such as dominant cone dystrophy, dominant cone-rod dystrophy, Leber's congenital amaurosis, recessive cone dystrophy, recessive cone-rod dystrophy, macular dystrophy, pattern dystrophy, vitelliform dystrophy, central choroidal dystrophy, Stargardt disease, austomal dominant, autosomal recessive and X-linked retinitis pigmentosa, retinitis pigmentosa associated with Bardet-Biedl syndrome, X-linked juvenile retinoschisis, achromatopsia, blue cone monochromacy, Usher syndrome types I, II and III, Duchenne Muscular Dystrophy, Limb Girdle Muscular Dystrophy, Spinal Muscular Atrophy, Pompe Disease, Friedrich's Ataxia, Mucopolysaccharidosis (MPS) (all forms), Lysosomal Storage Diseases (LSD) (all forms), Amyotrophic lateral sclerosis (ALS), Parkinson's disease, and Alzheimer's disease. In some embodiments, the subject has one or more endogenous mutant alleles associated with, or that cause, a disease, disorder or condition of the eye or retina, such as mutant alleles in the genes GUCY2D, GUCY2E, SPATA7, PRPH2, ABCA4, AIPL1, LCA5, RPGRIP1, CRX, CRB1, NMNAT1, CEP290, IMPDH1, RD3, RDH12, TULP1, KCNJ13, GDF6, IQCB1, BBS1, BBS2, ARL6/BBS3, BBS4, BBS5, BBS7, TTC8/BBS8, BBS10, TRIM32/BBS11, BBS12, CCDCC28B, CEP290, TMEM67, MKS1 MKKS, RHO, PRPF31, RP1, NRL, NR2E3, RPGR, RP2, PDE6A, PDE6B, PDE6G, RP25, CNGA1, CNGB1, MAK, RS1, CNGB3, CNGA3, GNAT2, OPN1LW, OPN1MW, CRX, GUCA1A (GCAP1), GUCA1B (GCAP2), ABCA4, PROM1 and ELOVL4, MYO7A, USH1C, CDH23, PCDH15, USH1G, USH2A, DFNB31 or CLRN1.

In particular embodiments, a replacement coding sequence is administered to the subject to provide a functional protein, e.g., GUCY2D or Gucy2e, to restore, e.g., completely or partially, photoreceptor function to a subject (e.g., a human). In some embodiments, one or both alleles of a target coding sequence of the subject are silenced by administering an rAAV particle comprising a heterologous nucleic acid sequence disclosed herein to the subject (e.g., to a human having dominant cone-rod dystrophy). In particular embodiments, the endogenous mutant alleles of one or more target coding sequences are silenced or suppressed by administering an rAAV particle disclosed herein.

In some embodiments, the heterologous nucleic acid sequence of any of the rAAV nucleic acid vectors of the disclosure has a sequence that has at least 95% identity, at least 98%, at least 99% identity, or 100% identity to a nucleotide sequence selected from SEQ ID NO: 9 or 10. The nucleotide sequences encoding the human GUCY2D gene (SEQ ID NO: 9) and mouse Gucy2e gene (SEQ ID NO: 10) are shown below.

GUCY2D:
```
                                         (SEQ ID NO: 9)
ATGACCGCCTGCGCCCGCCGAGCGGGTGGGCTTCCGGACCCCGGGCTCTG

CGGTCCCGCGTGGTGGGCTCCGTCCCTGCCCCGCCTCCCCCGGGCCCTGC

CCCGGCTCCCGCTCCTGCTGCTCCTGCTTCTGCTGCAGCCCCCCGCCCTC

TCCGCCGTGTTCACGGTGGGGGTCCTGGGCCCCTGGGCTTGCGACCCCAT

CTTCTCTCGGGCTCGCCCGGACCTGGCCGCCCGCCTGGCCGCCGCCCGCC

TGAACCGCGACCCCGGCCTGGCAGGCGGTCCCCGCTTCGAGGTAGCGCTG

CTGCCCGAGCCTTGCCGGACGCCGGGCTCGCTGGGGGCCGTGTCCTCCGC

GCTGGCCCGCGTGTCGGGCCTCGTGGGTCCGGTGAACCCTGCGGCCTGCC

GGCCAGCCGAGCTGCTCGCCGAAGAAGCCGGGATCGCGCTGGTGCCCTGG

GGCTGCCCCTGGACGCAGGCGGAGGGCACCACGGCCCCTGCCGTGACCCC

CGCCGCGGATGCCCTCTACGCCCTGCTTCGCGCATTCGGCTGGGCGCGCG

TGGCCCTGGTCACCGCCCCCCAGGACCTGTGGGTGGAGGCGGGACGCTCA

CTGTCCACGGCACTCAGGGCCCGGGGCCTGCCTGTCGCCTCCGTGACTTC

CATGGAGCCCTTGGACCTGTCTGGAGCCCGGGAGGCCCTGAGGAAGGTTC

GGGACGGGCCCAGGGTCACAGCAGTGATCATGGTGATGCACTCGGTGCTG

CTGGGTGGCGAGGAGCAGCGCTACCTCCTGGAGGCCGCAGAGGAGCTGGG

CCTGACCGATGGCTCCCTGGTCTTCCTGCCCCTTCGACACGATCCACTACG

CCTTGTCCCCAGGCCCGGAGGCCTTGGCCGCACTCGCCAACAGCTCCCAG

CTTCGCAGGGCCCACGATGCCGTGCTCACCCTCACGCGCCACTGTCCCTC

TGAAGGCAGCGTGCTGGACAGCCTGCGCAGGGCTCAAGAGCGCCGCGAGC

TGCCCTCTGACCTCAATCTGCAGCAGGTCTCCCCACTCTTTGGCACCATC

TATGACGCGGTCTTCTTGCTGGCAAGGGGCGTGGCAGAAGCGCGGGCTGC

CGCAGGTGGCAGATGGGTGTCCGGAGCAGCTGTGGCCCGCCACATCCGGG

ATGCGCAGGTCCCTGGCTTCTGCGGGGACCTAGGAGGAGACGAGGAGCCC

CCATTCGTGCTGCTAGACACGGACGCGGCGGGAGACCGGCTTTTTGCCAC

ATACATGCTGGATCCTGCCCGGGGGCTCCTTCCTCTCCGCCGGTACCCGGA

TGCACTTCCCGCGTGGGGGATCAGCACCCGGACCTGACCCCTCGTGCTGG

TTCGATCCAAACAACATCTGCGGTGGAGGACTGGAGCCGGGCCTCGTCTT

TCTTGGCTTCCTCCTGGTGGTTGGGATGGGGCTGGCTGGGGCCTTCCTGG

CCCATTATGTGAGGCACCGGCTACTTCACATGCAAATGGTCTCCGGCCCC
```

-continued

AACAAGATCATCCTGACCGTGGACGACATCACCTTTCTCCACCCACATGG

GGGCACCTCTCGAAAGGTGGCCCAGGGGAGTCGATCAAGTCTGGGTGCCC

GCAGCATGTCAGACATTCGCAGCGGCCCCAGCCAACACTTGGACAGCCCC

AACATTGGTGTCTATGAGGGAGACAGGGTTTGGCTGAAGAAATTCCCAGG

GGATCAGCACATAGCTATCCGCCCAGCAACCAAGACGGCCTTCTCCAAGC

TCCAGGAGCTCCGGCATGAGAACGTGGCCCTCTACCTGGGGCTTTTCCTG

GCTCGGGGAGCAGAAGGCCCTGCGGCCCTCTGGGAGGGCAACCTGGCTGT

GGTCTCAGAGCACTGCACGCGGGGCTCTCTTCAGGACCTCCTCGCTCAGA

GAGAAATAAAGCTGGACTGGATGTTCAAGTCCTCCCTCCTGCTGGACCTT

ATCAAGGGAATAAGGTATCTGCACCATCGAGGCGTGGCTCATGGGCGGCT

GAAGTCACGGAACTGCATAGTGGATGGCAGATTCGTACTCAAGATCACTG

ACCACGGCCACGGGAGACTGCTGGAAGCACAGAAGGTGCTACCGGAGCCT

CCCAGAGCGGAGGACCAGCTGTGGACAGCCCCGGAGCTGCTTAGGGACCC

AGCCCTGGAGCGCCGGGGAACGCTGGCCGGCGACGTCTTTAGCTTGGCCA

TCATCATGCAAGAAGTAGTGTGCCGCAGTGCCCCTTATGCCATGCTGGAG

CTCACTCCCGAGGAAGTGGTGCAGAGGGTGCGGAGCCCCCCTCCACTGTG

TCGGCCCTTGGTGTCCATGGACCAGGCACCTGTCGAGTGTATCCTCCTGA

TGAAGCAGTGCTGGGCAGAGCAGCCGGAACTTCGGCCCTCCATGGACCAC

ACCTTCGACCTGTTCAAGAACATCAACAAGGGCCGGAAGACGAACATCAT

TGACTCGATGCTTCGGATGCTGGAGCAGTACTCTAGTAACCTGGAGGATC

TGATCCGGGAGCGCACGGAGGAGCTGGAGCTGGAAAAAGCAGAAGACAGAC

CGGCTGCTTACACAGATGCTGCCTCCGTCTGTGGCTGAGGCCTTGAAGAC

GGGGACACCAGTGGAGCCCGAGTACTTTGAGCAAGTGACACTGTACTTTA

GTGACATTGTGGGCTTCACCACCATCTCTGCCATGAGTGAGCCCATTGAG

GTTGTGGACCTGCTCAACGATCTCTACACACTCTTTGATGCCATCATTGG

TTCCCACGATGTCTACAAGGTGGAGACAATAGGGGACGCCTATATGGTGG

CCTCGGGGCTGCCCCAGCGGAATGGGCAGCGACACGCGGCAGAGATCGCC

AACATGTCACTGGACATCCTCAGTGCCGTGGGCACTTTCCGCATGCGCCA

TATGCCTGAGGTTCCCGTGCGCATCCGCATAGGCCTGCACTCGGGTCCAT

GCGTGGCAGGCGTGGTGGGCCTCACCATGCCGCGGTACTGCCTGTTTGGG

GACACGGTCAACACCGCCTCGCGCATGGAGTCCACCGGGCTGCCTTACCG

CATCCACGTGAACTTGAGCACTGTGGGGATTCTCCGTGCTCTGGACTCGG

GCTACCAGGTGGAGCTGCGAGGCCGCACGGAGCTGAAGGGCAAGGGCGCC

GAGGACACTTTCTGGCTAGTGGGCAGACGCGGCTTCAACAAGCCCATCCC

CAAACCGCCTGACCTGCAACCGGGGTCCAGCAACCACGGCATCAGCCTGC

AGGAGATCCCACCCGAGCGGCGACGGAAGCTGGAGAAGGCGCGGCCGGGC

CAGTTCTCTTGA

Gucy2e:

(SEQ ID NO: 10)

ATGAGCGCTTGGCTCCTGCCAGCCGGAGGGCTTCCCGGCGCCGGGTTCTG

TGTCCCTGCGCGGCAGTCTCCGTCCAGTTTCTCGCGGGTCCTGCGCTGGC

-continued

CAAGGCCTGGGCTACCGGGACTCCTGCTACTGCTACTGCTCCCATCTCCT

TCTGCCCTCTCTGCTGTGTTCAAAGTGGGGGTGCTGGGCCCCTGGGCTTG

CGACCCCATCTTTGCACGGGCCCGACCAGACCTGGCTGCGCGTCTGGCCG

CCAACCGCCTGAATCGTGACTTTGCTTTAGACGGCGGCCCCCGGTTCGAG

GTTGCGCTGCTCCCAGAGCCCTGCCTGACTCCGGGCTCACTAGGGGCTGT

GTCCTCTGCGCTGTCTCGAGTCTCTGGCCTGGTGGGGTCCGGTGAACCCCG

CAGCCTGTCGGCCAGCCGAACTGTTGGCTCAAGAAGCTGGAGTAGCGCTG

GTGCCCTGGGGCTGCCCTGGCACGCGGGCGGCGGGTACTACAGCCCCGGC

GGTGACCCCCGCTGCAGATGCTCTCTACGTCCTCCTTAGAGCATTCCGCT

GGGCGCGCGTGGCCCTGATCACTGCACCCCAAGACCTGTGGGTGGAGGCG

GGACGCGCTCTGTCCACAGCACTCAGGGCCCGGGGTTTGCCAGTTGCCCT

AGTGACTTCCATGGAGACTTCAGACCGGTCTGGAGCCCGGGGAGGCCCTCG

GGAGGATCCGAGATGGGCCTAGAGTTAGAGTAGTGATCATGGTGATGCAC

TCGGTGCTGCTGGGCGGCGAGGAGCAGCGCTACCTACTGGAAGCTGCAGA

AGAACTGGCTCTGACTGATGGCTCCCTGGTTTTCCTGCCCTTCGACACGC

TTCACTACGCTTTGTCTCCAGGCCCGGAGGCTCTGGCTGCATTTGTCAAC

AGCTCCCAGCTCCGCAGGGCTCACGATGCGGTGCTCACACTCACGCGCCG

CTGTCCTCCTGGAGGCAGCGTGCAAGACAGCCTGCGCAGGGCTCAAGAAC

ACCAGGAACTGCCCCTTGACCTCAACCTGAAGCAGGTCTCTCCGCTGTTT

GGCACCATCTATGATGCTGTCTTCCTGTTGGCTGGGGGCGTGAAGAGAGC

AAGAACAGCGGTGGGTGGTGGCTGGGTGTCAGGTGCATCGTAGCCCGCC

AAGTACGGGAAGCACAAGTCTCTGGCTTTTGTGGGGTCCTGGGAAGAACC

GAGGAGCCCTCCTTTGTGCTGCTGGACACAGATGCATCCGGAGAACAGTT

GTTCGCAACACACCTGCTAGATCCTGTCTTAGGCTCCCTGCGTTCTGCAG

GGACCCCCATGCACTTCCCTAGAGGTGGACCTGCCCCGGGACCAGACCCT

TCCTGCTGGTTCGATCCAGATGTGATCTGCAACGGAGGGGTGGAGCCAGG

CCTGGTCTTTGTTGGCTTCCTCCTGGTGATAGGGATGGGACTGACTGGAG

CCTTCTTGGCTCATTACTTGAGGCACAGGCTGCTACACATGCAGATGGCT

TCCGGCCCCAACAAGATCATCTTGACGTTGGAAGATGTTACTTTCCTCCA

CCCACCGGGAGGCAGCTCTCGAAAGGTGGTCCAGGGAAGTAGATCCAGTC

TGGCTACCCGGAGCGCATCAGACATTCGCAGTGTCCCCAGCCAGCCCCAA

GAGAGCACCAACGTTGGCCTCTATGAGGGGGGACTGGGTTTGGCTGAAGAA

GTTCCCAGGGGAACATCATATGGCTATCAGGCCAGCAACAAAGACAGCCT

TCTCCAAGCTTCGAGAGCTCCGGCATGAGAATGTGGCTCTCTACTTGGGA

CTCTTCCTGGCGGGTACAGCAGACAGCCCTGCCACCCCTGGGGAGGGCAT

CTTGGCTGTGGTCTCAGAGCACTGTGCTCGGGGTTCCCTCCATGACCTCC

TGGCCCAGAGAGAAATAAAGCTGGACTGGATGTTCAAGTCTTCCCTCCTG

CTGGACCTCATCAAGGGAATGAGATATCTGCACCATCGCGGTGTGGCCCA

CGGGAGGCTCAAGTCACGGAATTGCGTGGTGGACGGGAGGTTCGTGCTCA

AGGTGACAGATCATGGCCATGGGCGACTGCTGGAAGCGCAAAGGGTGTTA

CCGGAACCTCCCAGTGCAGAGGATCAGCTATGGACAGCCCCAGAGCTTCT

-continued

```
TCGGGACCCCTCCCTGGAGCGCCGGGGAACTCTAGCTGGTGATGTCTTTA

GTCTGGCCATCATCATGCAGGAGGTCGTGTGCCGCAGCACCCCTTATGCC

ATGCTGGAACTAACGCCCGAGGAAGTAATACAGAGGGTGCGGAGCCCTCC

TCCACTGTGTCGGCCCTTGGTGTCCATGGACCAGGCACCCATGGAGTGCA

TCCAGCTGATGACACAATGCTGGGCAGAGCATCCAGAACTTCGGCCTTCC

ATGGACCTCACCTTTGACCTGTTCAAGAGCATCAACAAGGGCCGGAAGAC

CAACATCATCGACTCCATGCTTCGGATGCTGGAGCAGTACTCTAGTAACC

TGGAGGATCTGATCCGAGAACGCACAGAGGAGTTAGAGCAGGAGAAGCAG

AAGACAGACAGGCTGCTCACACAGATGCTGCCTCCATCTGTGGCTGAGGC

CCTGAAGATGGGGACATCTGTGGAGCCTGAGTACTTTGAAGAGGTGACAC

TCTACTTCAGTGACATCGTGGGCTTTACCACCATTTCAGCCATGAGCGAG

CCTATTGAGGTGGTAGACCTGCTTAATGACCTCTATACTCTCTTCGATGC

CATCATCGGTGCCCATGATGTCTATAAGGTGGAAACAATTGGAGATGCAT

ATATGGTGGCCTCCGGGCTGCCGCAGAGGAACGGGCAGCGGCACGCTGCA

GAGATTGCCAACATGTCACTGGACATCCTCAGTGCAGTCGGCTCCTTCCG

CATGCGCCATATGCCCGAGGTACCGGTGCGCATCCGCATTGGTTTGCACT

CAGGCCCGTGCGTGGCGGGTGTGGTGGGCCTCACCATGCCTCGGTACTGC

CTGTTCGGGGACACGGTCAACACTGCCTCGAGAATGGAGTCCACTGGACT

GCCTTACCGCATCCACGTTAACATGAGCACTGTTCGGATTCTTCGCGCTC

TGGACCAAGGCTTCCAGATGGAGTGTCGAGGCCGCACGGAGCTGAAGGGC

AAGGGTATTGAGGACACGTACTGGCTTGTGGGCAGACTTGGCTTCAACAA

GCCCATTCCCAAACCACCTGATCTGCAGCCAGGGGCCAGCAACCATGGTA

TCAGCCTGCAGGAGATTCCCCCAGAGAGACGCAAGAAGCTGGAGAAAGCC

AGGCCAGGCCAGTTTACTGGGAAGTGA
```

In some embodiments, the mammal is a human subject. In some embodiments, the mammal is a non-human primate subject. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. Other exemplary subjects include domesticated animals such as dogs and cats; livestock such as horses, cattle, pigs, sheep, goats, and chickens; and other animals such as mice, rats, guinea pigs, and hamsters.

In certain embodiments, methods are provided for subretinally administering to a fovea (e.g., foveal cone cells) of the mammal the rAAV particles described herein or compositions thereof. In particular embodiments, detachment of the fovea is minimized during and/or after subretinal administration. In particular embodiments, subretinal administration of the rAAV particle is performed in the absence of any detachment of the fovea.

In some embodiments, the dose of rAAV particles administered to a cell or a subject may be on the order ranging from $10^6$ to $10^{14}$ particles/mL or $10^3$ to $10^{15}$ particles/mL, or any values therebetween for either range, such as for example, about $10^6$, $10^7$, $10^8$, $10^9$, $10^{10}$, $10^{11}$, $10^{12}$, $10^{13}$, or $10^{14}$ particles/mL. In one embodiment, rAAV particles of higher than $10^{13}$ particles/mL are be administered. In some embodiments, the dose of rAAV particles administered to a subject may be on the order ranging from $10^6$ to $10^{14}$ vector genomes(vgs)/mL or $10^3$ to $10^{15}$ vgs/mL, or any values therebetween for either range, such as for example, about $10^6$, $10^7$, $10^8$, $10^9$, $10^{10}$, $10^{11}$, $10^{12}$, $10^{13}$, or $10^{14}$ vgs/mL. In one embodiment, rAAV particles of higher than $10^{13}$ vgs/mL are be administered. The rAAV particles can be administered as a single dose, or divided into two or more administrations as may be required to achieve therapy of the particular disease, disorder or condition being treated. In some embodiments, 0.0001 mL to 10 mLs (e.g., 0.0001 mL, 0.001 mL, 0.01 mL, 0.1 mL, 1 mL, 10 mLs) are delivered to a subject in a dose.

In some embodiments, rAAV particle titers range from $1 \times 10^{10}$-$5 \times 10^{13}$ vg/ml. In some embodiments, rAAV particle titers can be $1 \times 10^{10}$, $2.5 \times 10^{10}$, $5 \times 10^{10}$, $1 \times 10^{11}$, $2.5 \times 10^{11}$, $5 \times 10^{11}$, $1 \times 10^{12}$, $2.5 \times 10^{12}$, $5 \times 10^{12}$, $1 \times 10^{13}$, $2.5 \times 10^{13}$, or $5 \times 10^{13}$ vg/mL. In some embodiments, particle titers are less than $1 \times 10^{10}$ vg/mL. In some embodiments, rAAV particle titers are greater than $1 \times 10^{15}$ vg/mL. In one embodiment, rAAV particle titers are greater than $5 \times 10^{13}$ vgs/mL. In some embodiments, rAAV particles are administered via methods described herein (e.g., subretinally or intravitreally).

The rAAV particles can be administered as a single dose, or divided into two or more administrations as may be required to achieve therapy of the particular disease, disorder or condition being treated. In some embodiments, from 1 to 500 microliters of a composition (e.g., comprising an rAAV particle) described in this application is administered to one or both eyes of a subject. For example, in some embodiments, about 1, about 10, about 50, about 100, about 200, about 300, about 400, or about 500 microliters can be administered to each eye. However, it should be appreciated that smaller or larger volumes could be administered in some embodiments.

In some embodiments, the disclosure provides formulations of one or more rAAV-based compositions disclosed herein in pharmaceutically acceptable solutions for administration to a cell or an animal, either alone or in combination with one or more other modalities of therapy, and in particular, for therapy of human cells, tissues, and diseases affecting man.

If desired, the rAAV particles described herein may be administered in combination with other agents as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The rAAV particles may thus be delivered along with various other agents as required in the particular instance. Such compositions may be purified from host cells or other biological sources, or alternatively may be chemically synthesized as described herein.

Formulation of pharmaceutically-acceptable excipients and carrier solutions is well-known to those of skill in the art, as is the development of suitable dosing and treatment regimens for using the particular compositions described herein in a variety of treatment regimens, including e.g., subretinal, intravitreal, parenteral, intravenous, intranasal, intra-articular, and intramuscular administration and formulation.

Typically, these formulations may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In certain circumstances it will be desirable to deliver an rAAV particle as described herein (e.g., comprising a AAV44.9(E531D) capsid) in suitably formulated pharmaceutical compositions disclosed herein either subretinally, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs by direct injection.

The pharmaceutical forms of compositions (e.g., comprising an rAAV particle as described herein) suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

The term "carrier" refers to a diluent, adjuvant, excipient, or vehicle with which the rAAV particle as described herein is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers.

The compositions of the present disclosure can be delivered to the eye through a variety of routes. They may be delivered intraocularly, by topical application to the eye or by intraocular injection into, for example the vitreous (intravitreal injection) or subretinal (subretinal injection) interphotoreceptor space. In some embodiments, they are delivered to rod photoreceptor cells. Alternatively, they may be delivered locally by insertion or injection into the tissue surrounding the eye. They may be delivered systemically through an oral route or by subcutaneous, intravenous or intramuscular injection. Alternatively, they may be delivered by means of a catheter or by means of an implant, wherein such an implant is made of a porous, non-porous or gelatinous material, including membranes such as silastic membranes or fibers, biodegradable polymers, or proteinaceous material. They can be administered prior to the onset of the condition, to prevent its occurrence, for example, during surgery on the eye, or immediately after the onset of the pathological condition or during the occurrence of an acute or protracted condition.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions may be prepared by incorporating an rAAV particle as described herein in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The amount of composition (e.g., comprising an rAAV particle as described herein) and time of administration of such composition will be within the purview of the skilled artisan having benefit of the present teachings. It is likely, however, that the administration of therapeutically-effective amounts of the disclosed compositions may be achieved by a single administration, such as for example, a single injection of sufficient numbers of rAAV particles to provide therapeutic benefit to the patient undergoing such treatment. Alternatively, in some circumstances, it may be desirable to provide multiple, or successive administrations of the composition, either over a relatively short, or a relatively prolonged period of time, as may be determined by the medical practitioner overseeing the administration of such compositions.

In some embodiments, visual acuity can be maintained or restored (e.g., partially or completely) after administering one or more compositions described in this application. In some embodiments, one or more photoreceptor cells or one or more RPE cells may be preserved, partially or completely, and/or one or more rod- and/or cone-mediated functions may be restored, partially or completely, after administering one or more compositions described in this application.

To "treat" a disease as the term is used herein, means to reduce the frequency or severity of at least one sign or symptom of a disease, disorder or condition experienced by a subject (e.g., cone-rod dystrophy). The compositions described above are typically administered to a subject in an effective amount, that is, an amount capable of producing a desirable result. The desirable result will depend upon the active agent being administered. For example, an effective amount of a rAAV particle may be an amount of the particle that is capable of transferring a heterologous nucleic acid to a host organ, tissue, or cell.

Toxicity and efficacy of the compositions utilized in methods of the disclosure can be determined by standard pharmaceutical procedures, using either cells in culture or experimental animals to determine the LD50 (the dose lethal to 50% of the population). The dose ratio between toxicity and efficacy the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

EXAMPLES

The following examples are included to demonstrate preferred embodiments of the invention. It should be appreciated by those of skill in the art that the techniques disclosed in the examples that follow represent techniques discovered by the inventor to function well in the practice of the invention, and thus may be considered to constitute preferred modes for its practice. However, those of skill in the art should, in light of the present disclosure, appreciate that many changes may be made in the specific embodiments which are disclosed and still obtain a like or similar result without departing from the spirit and scope of the invention.

Example 1-Therapeutic Molecules for AAV-Based Retinal Gene Therapies

Retinal transduction and tropism of AAV44.9 were evaluated following intravitreal (Ivt) or subretinal (SR) injection. By utilizing a mouse model with constitutive expression of GFP in all rod photoreceptors (Nrl-GFP Smouse) photoreceptor transduction efficiency was quantified for AAV44.9 and benchmark capsids AAV5 and AAV8 (Y733F).

It was sought to determine whether transduction of AAV44.9 could be improved by the addition of a Y-F mutation at residue 733 (Y733F) and separately a substitution of glutamic acid-to-aspartic acid at position 531 (E531D). As cone photoreceptors are the target of many retinal gene therapies (e.g., Achromatopsia and Cone-rod dystrophies) the ability of AAV44.9 to express transgenes in cone photoreceptors was assessed.

Experimental Methods

An AAV capsid phylogenetic tree is shown in FIG. 1. VP1 amino acid sequences for AAVs were aligned using ClustalW (AlignX-Vector NTI). The alignment was then used to generate a phylogenetic tree via the Neighbor-joining methods using EMBL-EBI Simple Phylogeny program (ebi-.ac.uk/Tools/phylogeny/simple_phylogeny/). The resulting tree was visualized using TreeView program and AAV5 designated as the outgroup.

Vector Production

A self-complementary AAV construct containing the truncated chimeric CMV-Chicken Beta Actin (smCBA) promoter driving mCherry (sc-smCBA-mCherry) was packaged into AAV44.9. AAV5 and AAV8 (Y733F) using a triple transfection-plasmid based system in adherent HEK293T seeded in double-stack cell factories (1,272 cm$^2$ cell growth area). Cells were harvested and lysed by successive freeze thaw cycles. Virus within the lysate was purified by iodixanol density gradient and was buffer exchanged into ALCON® BSS® balanced salt solution supplemented with TWEEN® 20 (polysorbate 20) (0.014%). Virus was titered by qPCR relative to a standard and stored at −80 C. Addition of Y733F and E531D substitutions were accomplished by site-directed mutagenesis of the AAV2rep-44.9cap plasmid and confirmed by Sanger sequencing. An additional construct containing the cone-specific, IRBPe-GNAT2 chimeric promoter driving green fluorescent protein (GFP) was packaged in AAV44.9.

In-Vitro Transduction Assay

ARPE-19 (human retinal pigment epithelial cell line) and 661W (mouse cone cell line) cells were seeded in 96 well plates at a concentration of $1.0 \times 10^4$ cells/well. The following day, cells were infected at 10,000 p/cell. Three days post-infection, fluorescent microscopy at a fixed exposure was performed, cells were detached and flow-cytometry was used to quantify reporter protein expression (mCherry) via fluorescence. mCherry expression was calculated by multiplying the mean mCherry fluorescence times the number of positive cells. Graphs represent expression levels minus the level of cells only.

Injection $2 \times 10^9$ vg in 1 ul of vector containing solution was delivered either intravitreally or subretinally to 4-5 weeks old Nrl-GFP and C57BL/6J mice. A minimum of 6 eyes receiving successful injections were analyzed in each experiment.

Fundoscopy

At 4 weeks post-injection, fundoscopy was performed using a Micron III camera (Phoenix Research Laboratories, Pleasanton, CA). Bright field and red fluorescent images were taken to visualize retinal health and mCherry expression, respectively. Exposure settings were constant between experiments and are indicated in the figure legends.

Measurement of Retinal Transduction Via Flow-Cytometry

Neural retinas (with RPE manually stripped from retina) from between 4 to 6 Nrl-GFP eyes per cohort were harvested and dissociated with papain. Flow-cytometry was performed on treated, dissociated retinas and untreated controls to quantify the percentage of cells that were positive for GFP (rod photoreceptors), mCherry (non-rod retinal neurons transduced by rAAV), or both (rod photoreceptors transduced by rAAV). The percentage of rods and non-rod neural retinal cells transduced by each vector were separately averaged.

Tissue Preparation and Immunostaining

Four weeks post-injection, the eyes were enucleated, fixed overnight at 4° C. in freshly prepared 4% paraformaldehyde (PFA) in phosphate-buffered saline (PBS). Cornea and lens were removed, and the eye cup was incubated in 30% sucrose solution overnight at 4° C. Eyes were embedded in cryostat compound and frozen at −80° C. Sections (12 μm thick) were cut using a cryostat (Leica Microsystem, Buffalo Grove, IL) and transferred to glass slides. Retinal cryosections were rinsed with 1× phosphate-buffered saline (PBS), blocked with 0.5% Triton-X100 and 1% bovine serum albumin (BSA) for 1 hour each and then incubated overnight at 4° C. with mouse monoclonal anti cone arrestin antibody (1:1000, generously provided by Dr Clay Smith). The following day slides were rinsed with 1×PBS and then incubated at room temperature for 1 hour with Alexa Fluor donkey-anti-mouse secondary antibody (1:500) in 1×PBS and counter-stained with DAPI. Images were acquired using confocal laser scanning microscope (Leica TCS SP8) and Fluorescence microscope (EVOS).

Results

Transduction of Rods by AAV44.9 Greater than that of Benchmark Vectors AAV5 and AAV8 (Y733F)

Figure 2A:
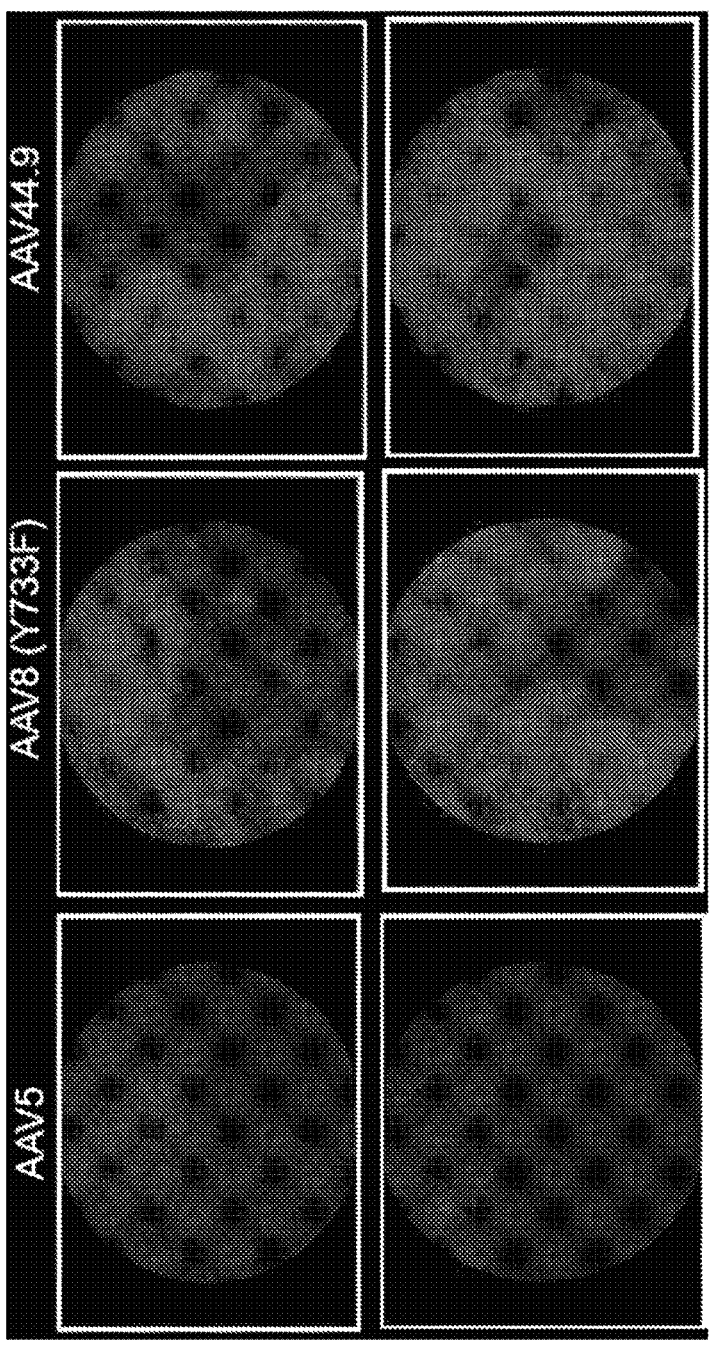
FIGS. 2A, 2B, 2C, 2D, and 2E show qualitative and quantitative analysis of AAV44.9, AAV5 and AAV8 (Y733F) at 4 weeks of subretinal injection.
Figures 2B, 2C:
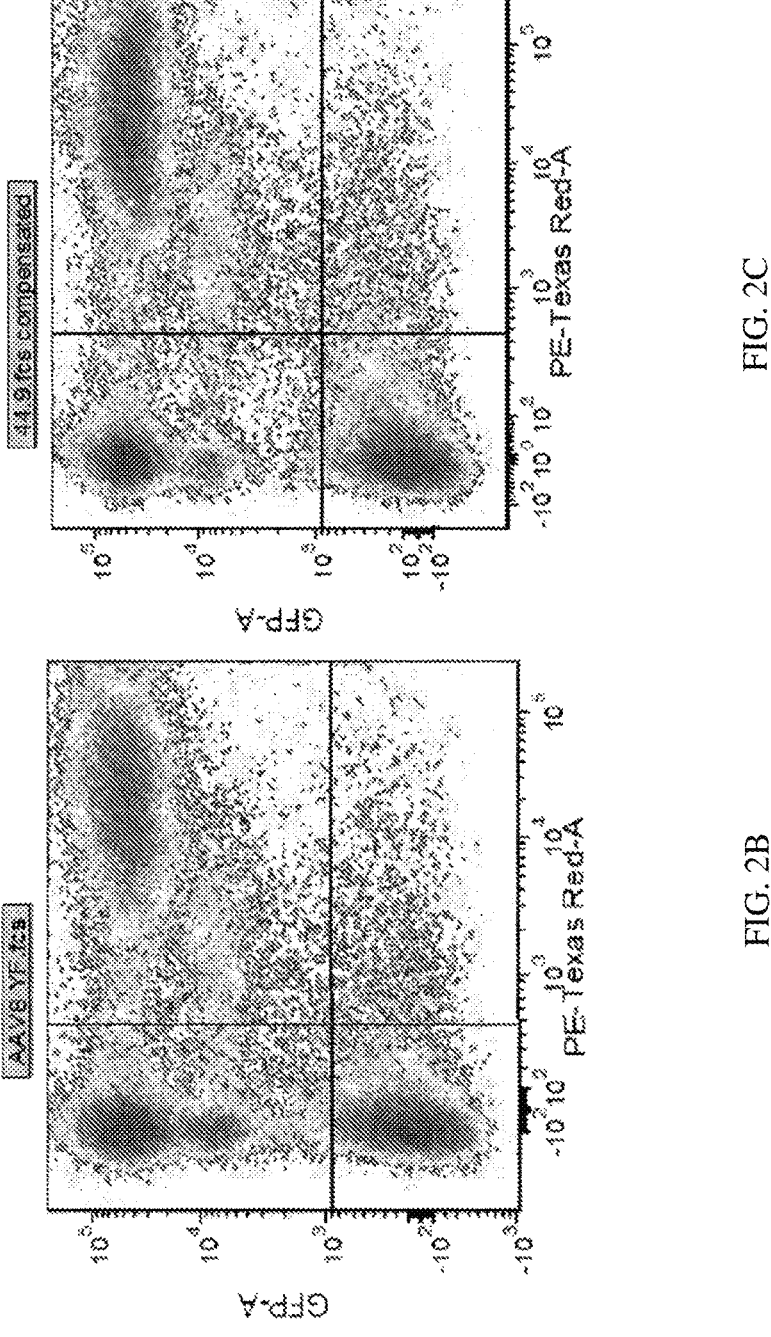
Figure 2D:
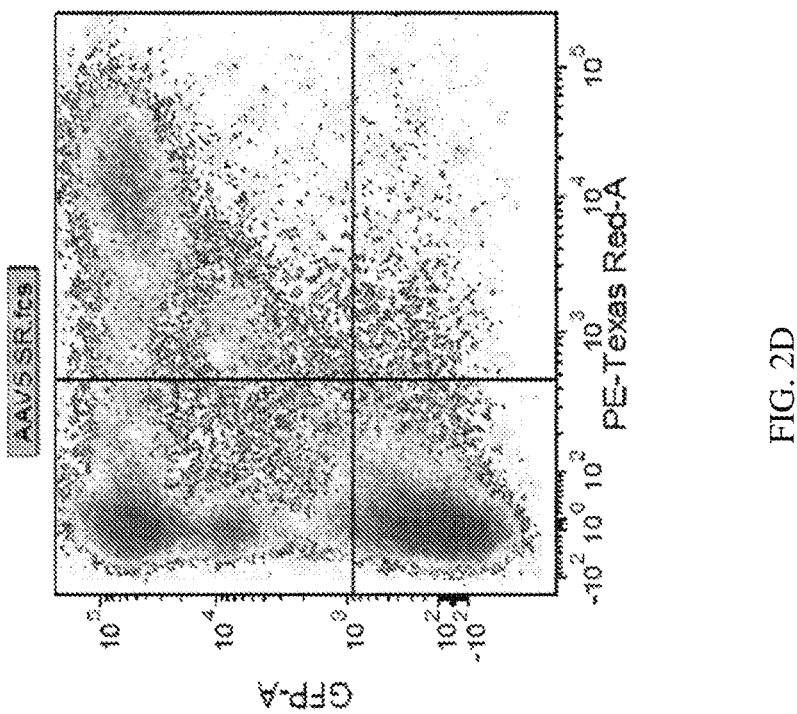
Figure 2E:
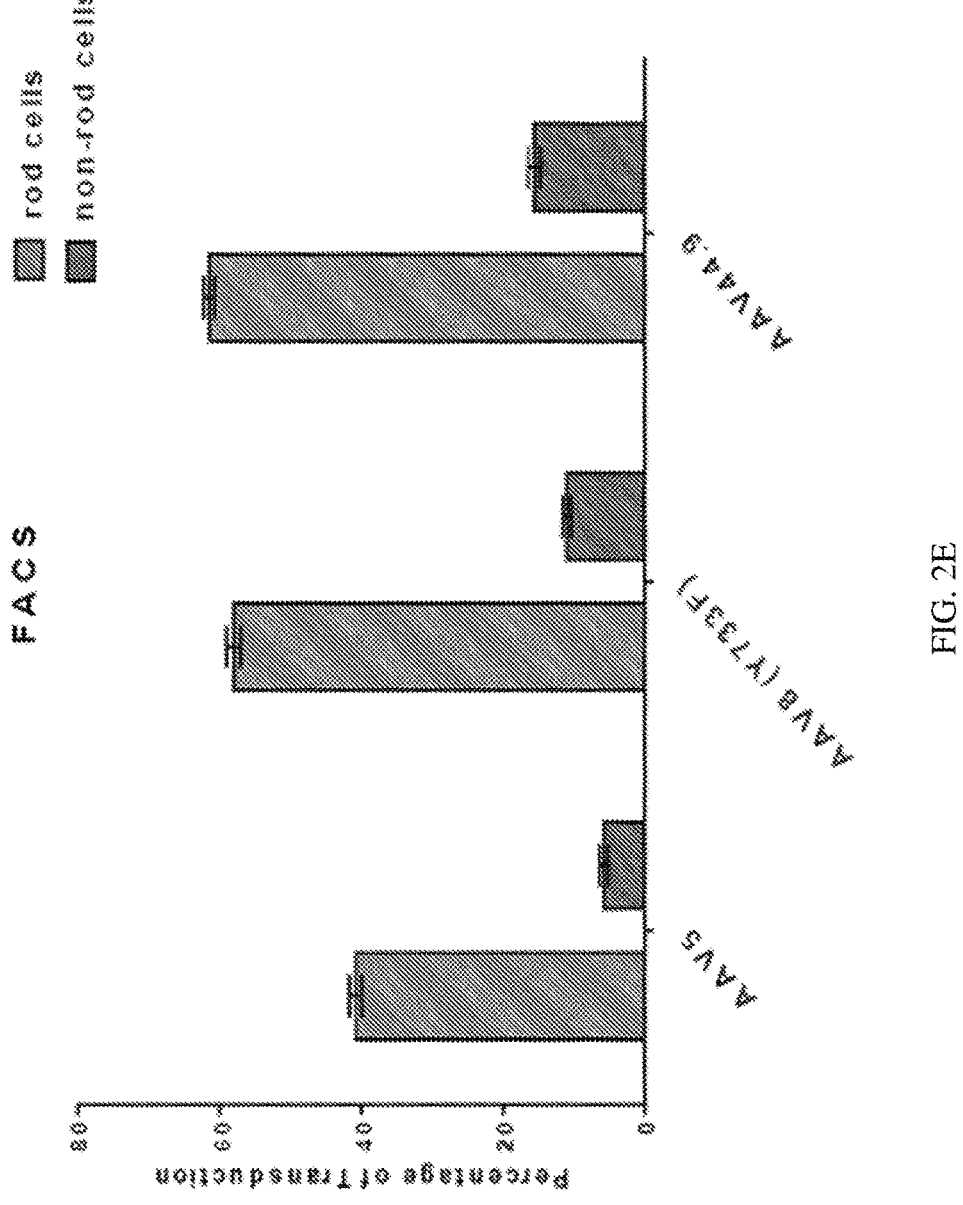
Figures 3A, 3B, 3C:
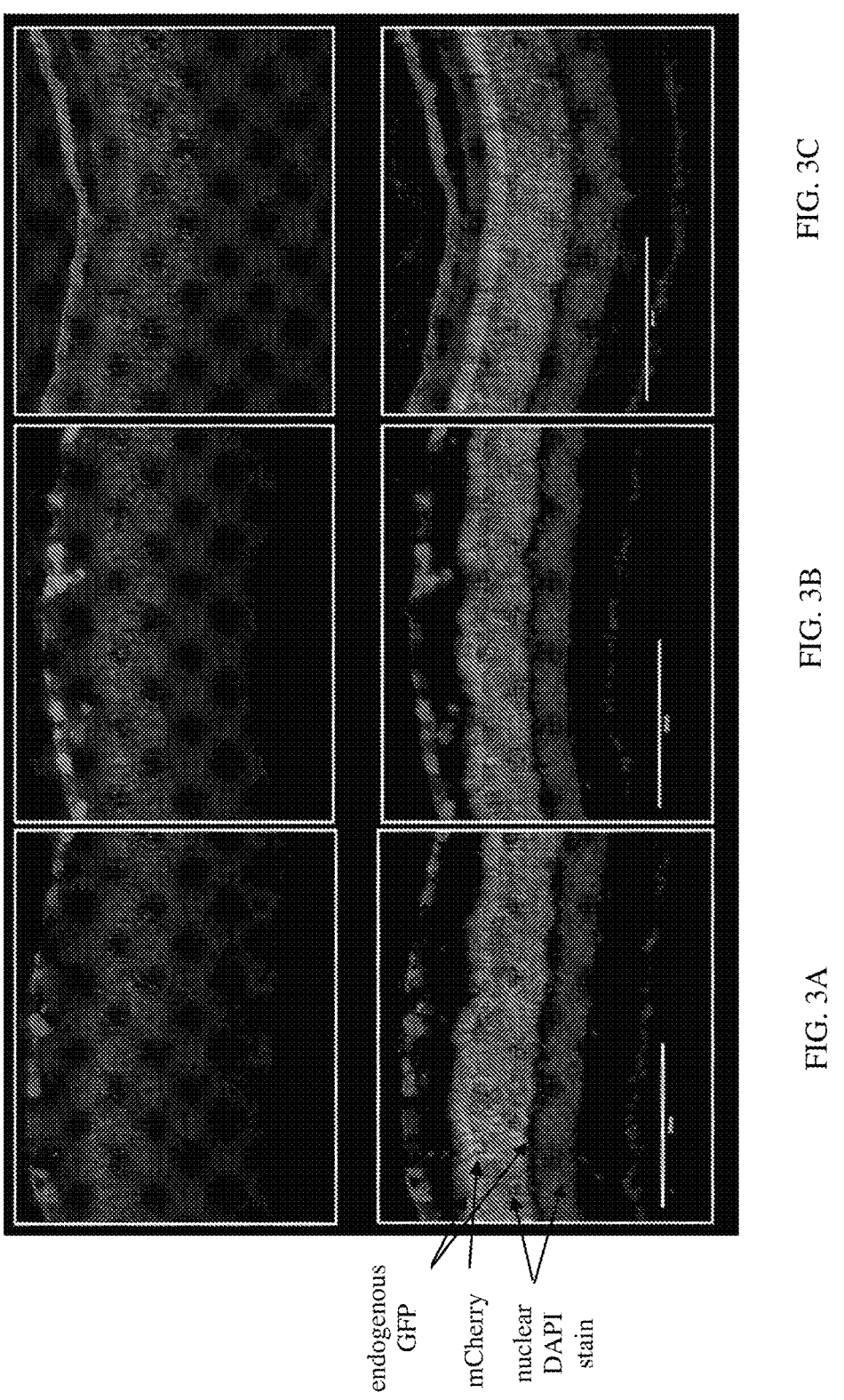
FIGS. 3A, 3B, and 3C show representative retinal cross section images showing mCherry expression in photoreceptors and retinal pigment epithelial ("RPE") in Nrl-GFP transgenic mouse retina injected with AAV5 (upper panel, FIG. 3A), AAV8(Y733F) (upper panel, FIG. 3B) AAV44.9 (upper panel, FIG. 3C) at 4 weeks after subretinal injection. The lower panels of FIGS. 3A, 3B, and 3C show overlapped images of nuclear DAPI stain, endogenous GFP expression in rod cells and mCherry expression in photoreceptor cells, as indicated by arrows.

Qualitative and quantitative analysis of AAV44.9, AAV5 and AAV8 (Y733F) at 4 weeks of subretinal injection is shown in FIGS. 2A-2E. The FACS data depicted in FIG. 2E show that AAV44.9 transduced rod more efficiently than AAV5 and AAV8 (Y733F) following subretinal injection with $2\times10^9$ vg. Representative retinal cross section images showing mCherry expression in photoreceptors and RPE in Nrl-GFP mouse retina injected with AAV5, AAV8 (Y733F), and AAV44.9 are shown in FIGS. 3A-3C at 4 weeks after subretinal injection.

Figure 4A:
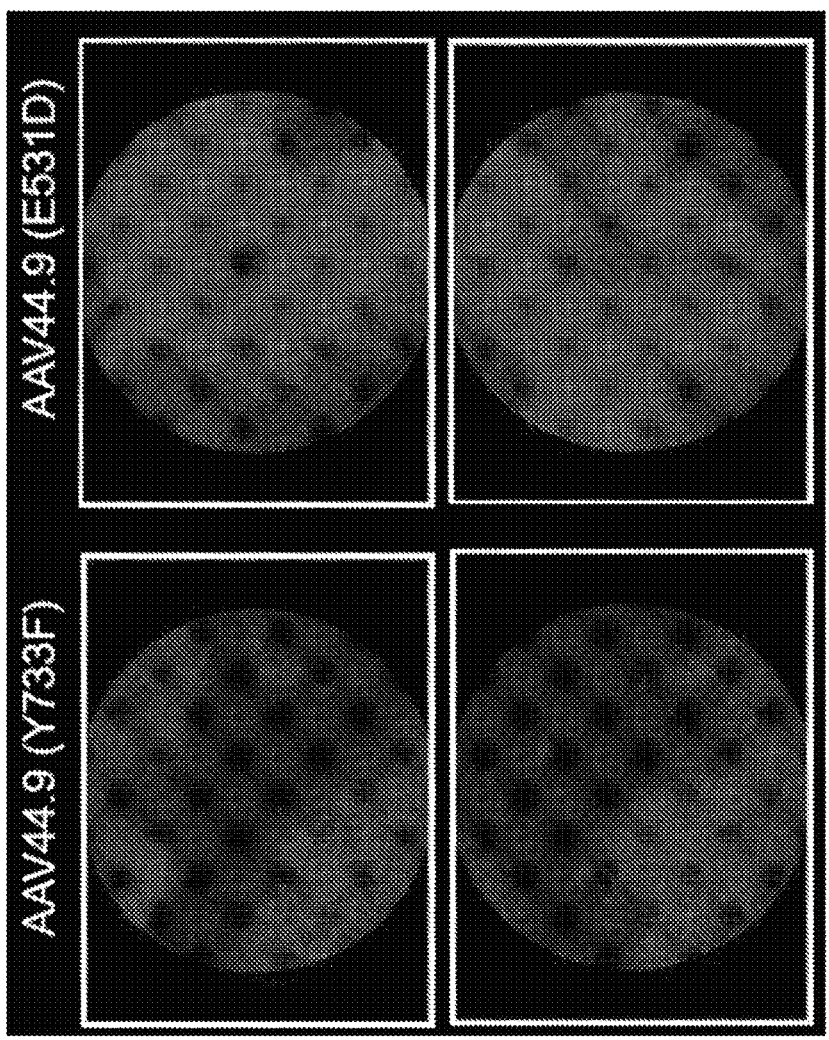
Figure 4C:
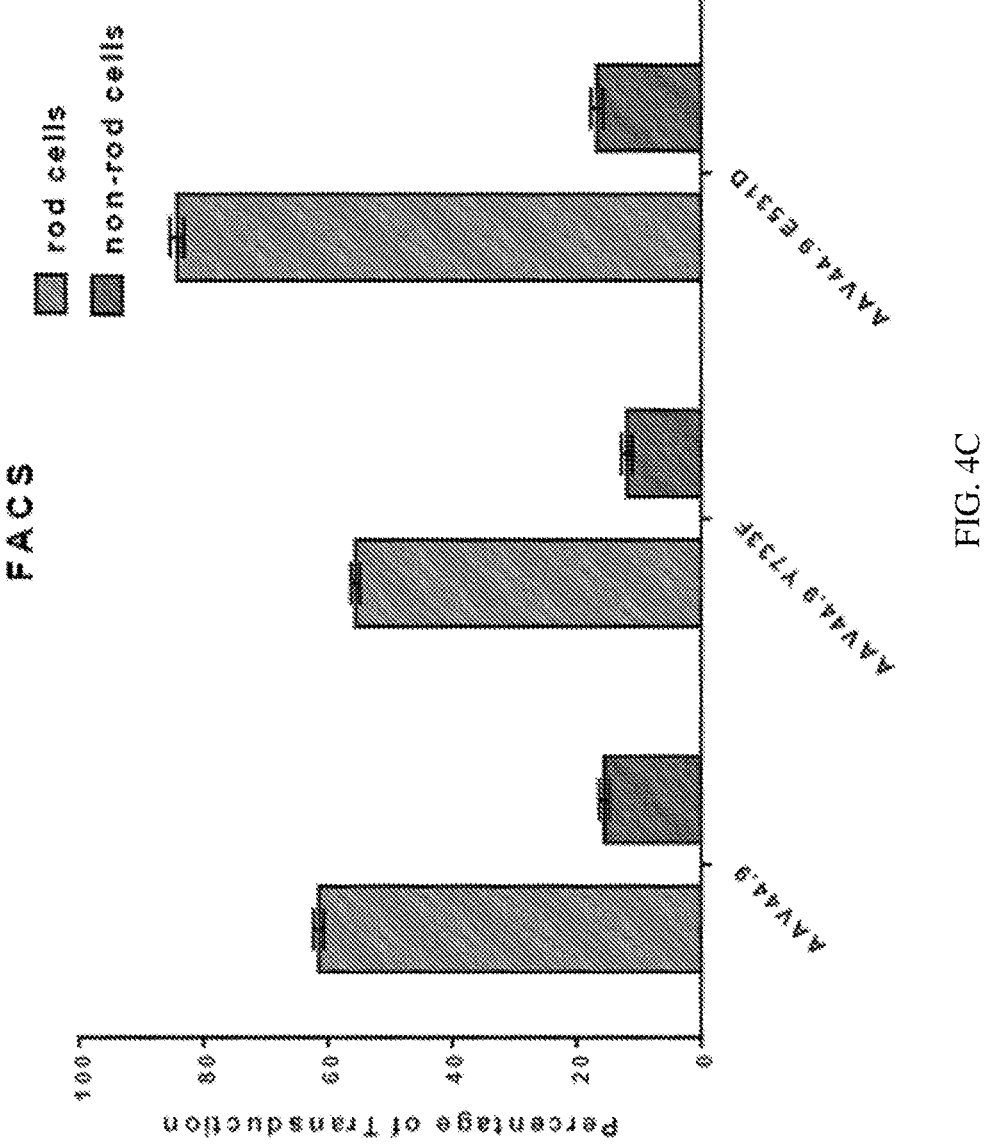

Qualitative and quantitative analysis of the AAV44.9 (Y733F) and AAV44.9(E531D) are shown in FIGS. 4A-4C. The FACS data depicted in FIG. 4C show that AAV44.9 (E531D) transduced rod cells more efficiently than AAV44.9 and AAV44.9(Y733F) following subretinal injection with $2\times10^9$ vg. Representative retinal cross section images showing mCherry expression primarily in photoreceptors and RPE in Nrl-GFP mouse retina injected with AAV44.9 (Y733F) and AAV44.9(E531D) are shown in FIG. 5A and FIG. 5B at 4 weeks after subretinal injection.

Figure 6A:
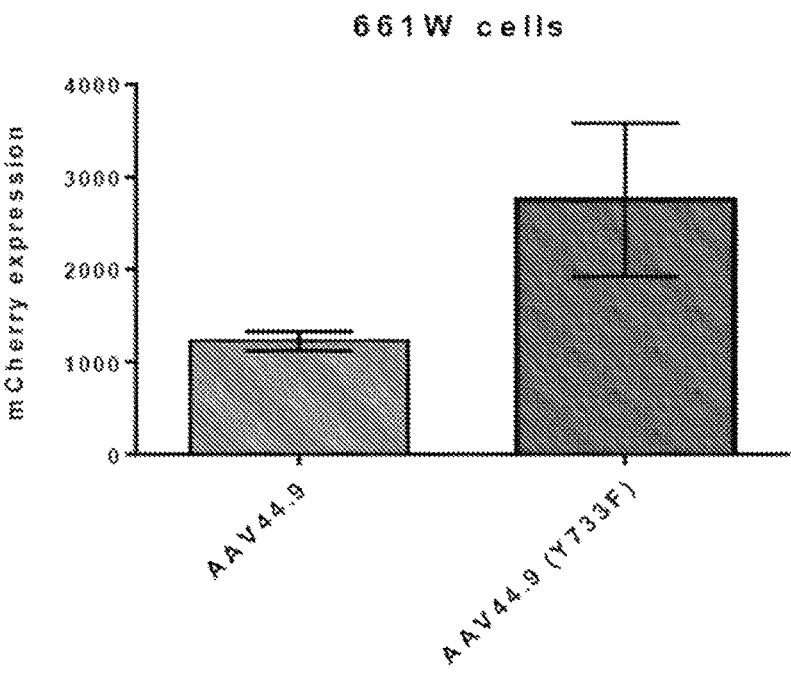
FIGS. 6A and 6B show transduction efficiency of AAV44.9 and AAV44.9(Y733F) in ocular cell lines. AAV44.9(Y733F) displayed increased transduction relative to AAV44.9 in mouse cone photoreceptor cell line (FIG. 6A). However, AAV44.9 was more efficient than AAV44.9 (Y733F) in human RPE cell line (FIG. 6B).
Figure 6B:
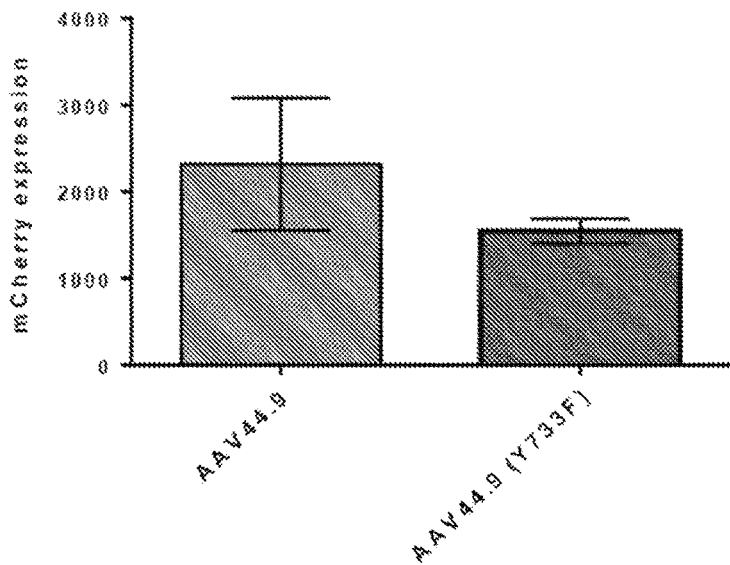

Transduction efficiency of unmodified AAV44.9 and AAV44.9(Y733F) in ocular cell lines is indicated in FIGS. 6A and 6B. AAV44.9(Y733F) displayed increase transduction relative to AAV44.9 in mouse cone photoreceptor cell line (FIG. 6A), whereas AAV44.9 was more efficient than AAV9 (Y733F) in human RPE cell line (FIG. 6B).

Figure 7A:
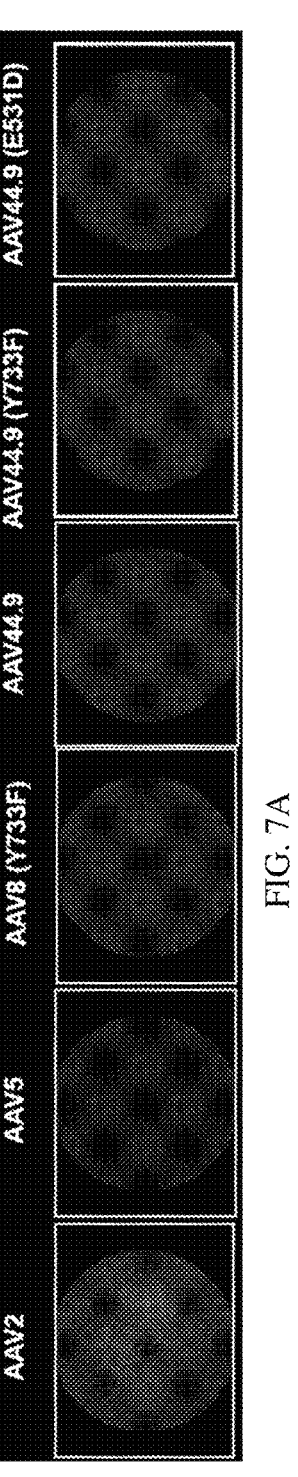
FIGS. 7A and 7B show qualitative analysis of AAVs following intravitreal injection.
Figure 7B:
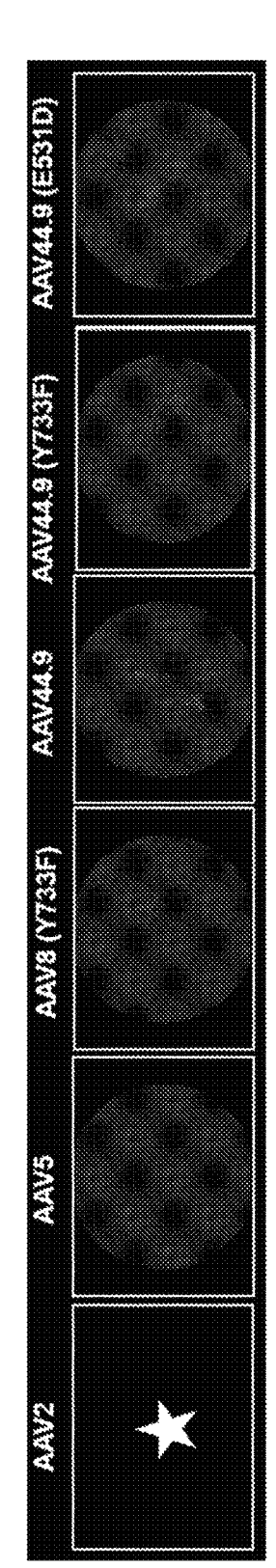

Qualitative analysis of AAV capsids following intravitreal injection is shown in FIGS. 7A and 7B. Similar to AAV5 and AAV8 (Y733F), AAV44.9 and its derivatives do not lead to efficient retinal transduction following Ivt injection.

Figure 8A:
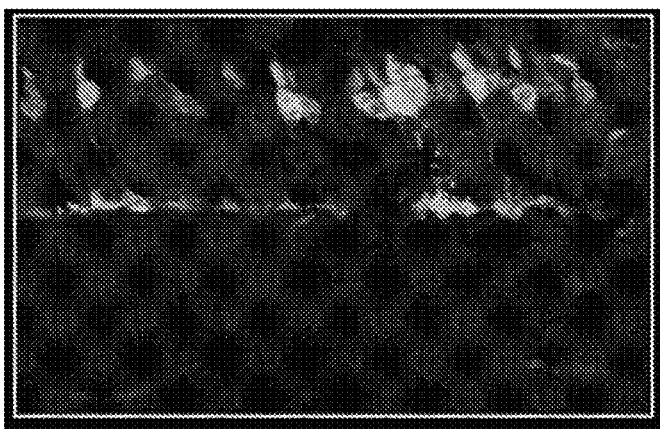
FIGS. 8A, 8B, and 8C show AAV44.9 containing the cone preferential chimeric IRBP enhancer-cone transducin promoter (IRBP/GNAT2) promoter and a GFP reporter showing
Figure 8B:
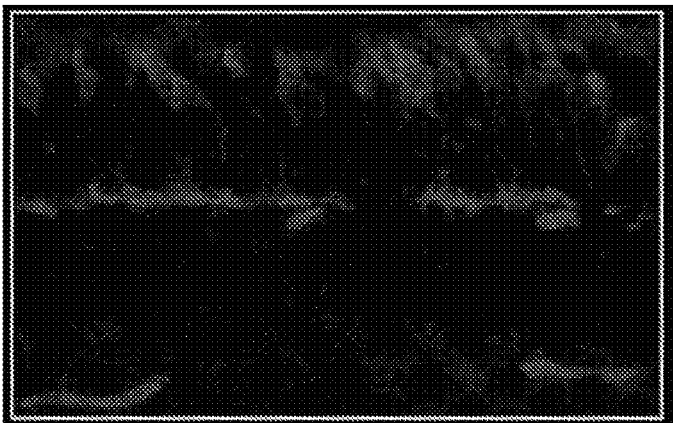
Figure 8C:
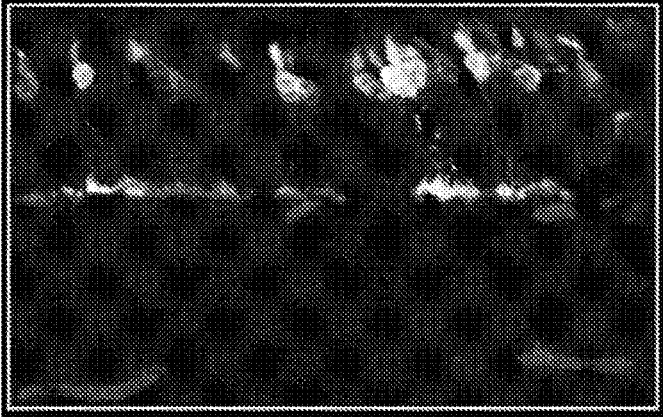

AAV44.9 containing the cone preferential IRBP/GNAT2 promoter and a GFP reporter shows GFP expression in cone cells in FIG. 8A, at 4 weeks after SR injection. FIGS. 8B and 8C also show that co-staining with cone-arrestin antibody colocalizes with GFP fluorescence.

The above-discussed results show that transduction of rods by AAV44.9 was greater than that of benchmark vectors, unmodified AAV5 and AAV8 (Y733F). The addition of Y733F mutation to AAV44.9 did not improve transduction of photoreceptors in vivo. The results also show that the E531D mutation greatly increased photoreceptor transduction, with AAV44.9(E531D) displaying 82% rod transduction compared to 61% transduction for unmodified AAV44.9. AAV44.9 effectively transduces cone cells as shown by subretinal delivery of AAV44.9-IRBPe/GNAT2-GFP. Similar to AAV5 and AAV8 (Y733F), AAV44.9 and its derivatives do not efficiently transduce retina following Ivt delivery.

AAV44.9(E531D) Outperforms Unmodified AAV44.9 and AAVrh.8 in Mouse Retina Following Subretinal Injection

Figure 9A:
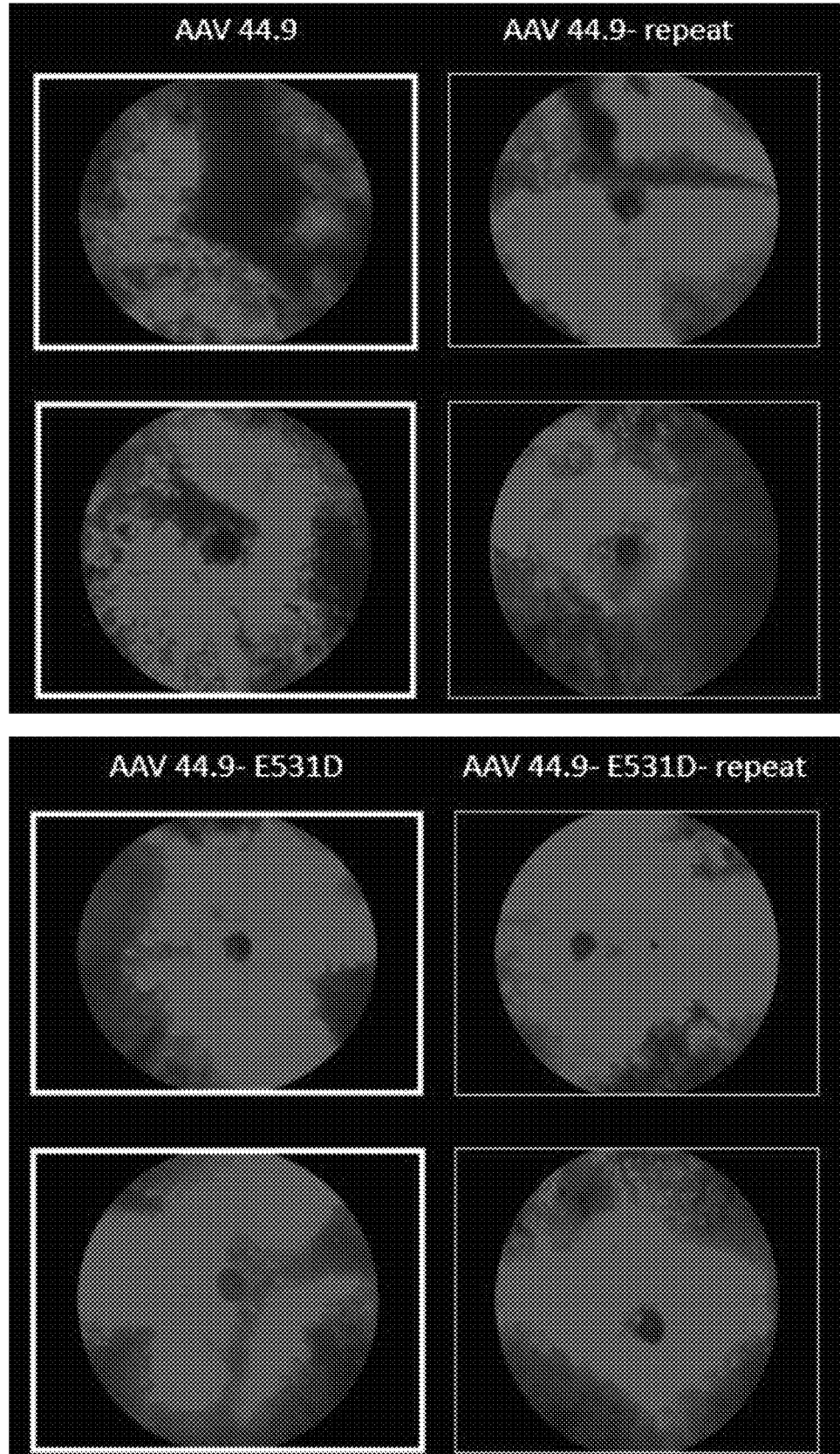
FIG. 9A shows representative fundus images (red fluorescent filter) of Nrl-GFP mice taken 4 weeks post subretinal injection with AAV44.9 or AAV44.9(E531D). Vectors were delivered at $2 \times 10^9$ vg in 1 uL. Exposure and gain settings were consistent over the course of the experiment.

Representative fundus images (red fluorescent filter) of Nrl-GFP mice was taken 4 weeks post subretinal injection with AAV44.9 or AAV44.9(E531D) (see FIG. 9A). Vectors were delivered at $2\times10^9$ vg in 1 uL. Exposure and gain settings were consistent over the course of the experiment. The experiment was repeated twice to confirm results. Note that 'repeat' experiments were performed with different lots of virus.

Figure 9B:
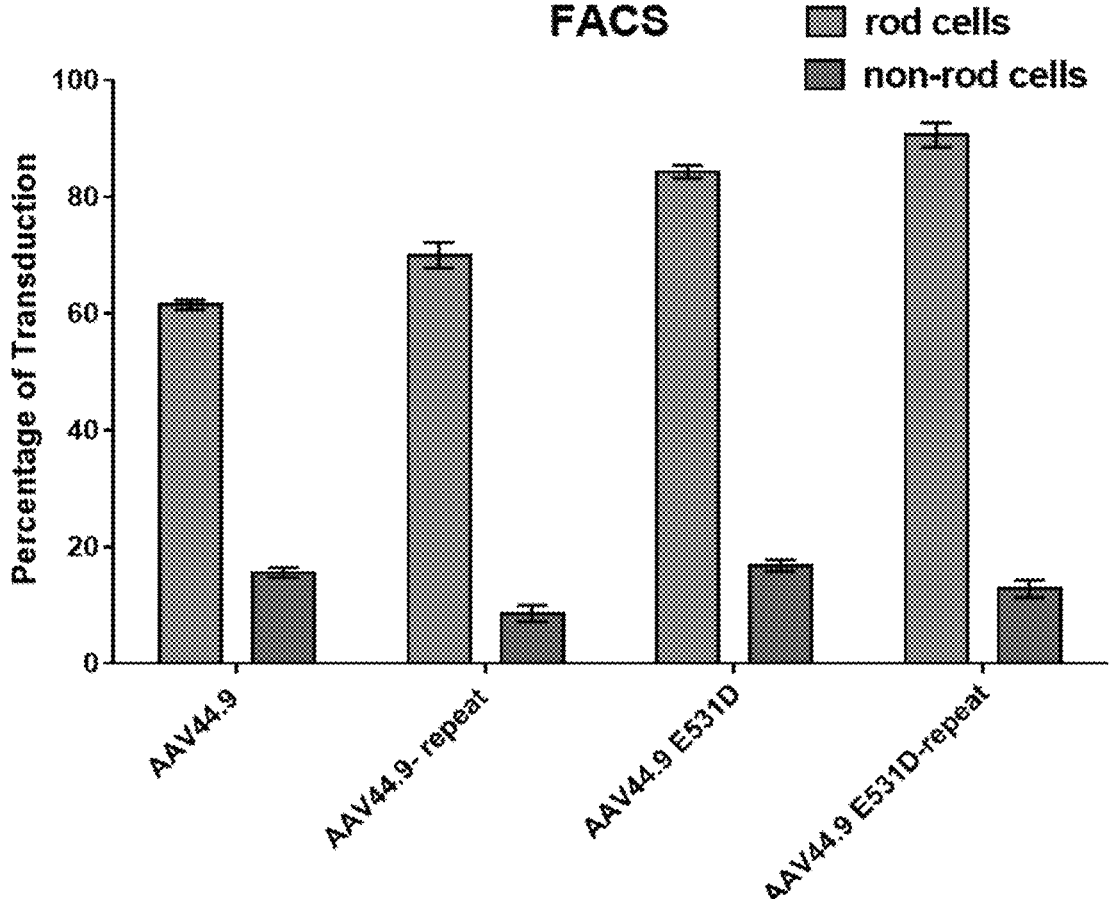
FIGS. 9B-9C show percent transduction of each cell population and corresponding values taken at 4 weeks post-injection. Retinas of Nrl-GFP mice (from FIG. 9A) were dissociated with papain and flow cytometry performed to quantify the percentage transduced rods (GFP+mCherry positive) or non rod cells (mCherry positive) as previously described in Boye et al., Impact of Heparan Sulfate Binding on Transduction of Retina by Recombinant Adeno-Associated Virus Vectors, *J. Virol.* 2016, 90(8):4215-4231, the entire contents of which is herein incorporated by reference.
Figure 9C:
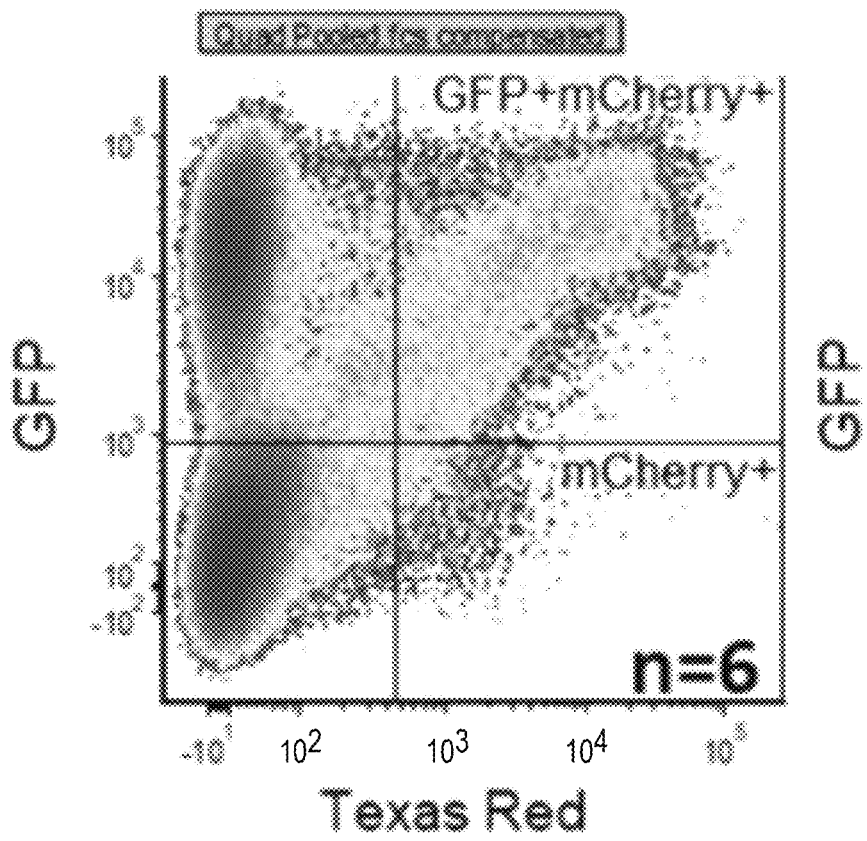

At 4 weeks post-injection, retinas of Nrl-GFP mice (same mice from experiment in FIG. 9A) were dissociated with papain and flow cytometry performed to quantify the percentage transduced rods (GFP+mCherry positive) or non rod cells (mCherry positive) as described in Boye et al., Impact of Heparan Sulfate Binding on Transduction of Retina by Recombinant Adeno-Associated Virus Vectors, *J. Virol.* 2016, 90(8):4215-4231. Percent transduction of each cell population and corresponding values are shown in FIG. 9B. AAV44.9(E531D) transduced a higher percentage of rod photoreceptors relative to unmodified AAV44.9. Note that 'repeat' experiments were performed with different lots of virus.

Figure 10A:
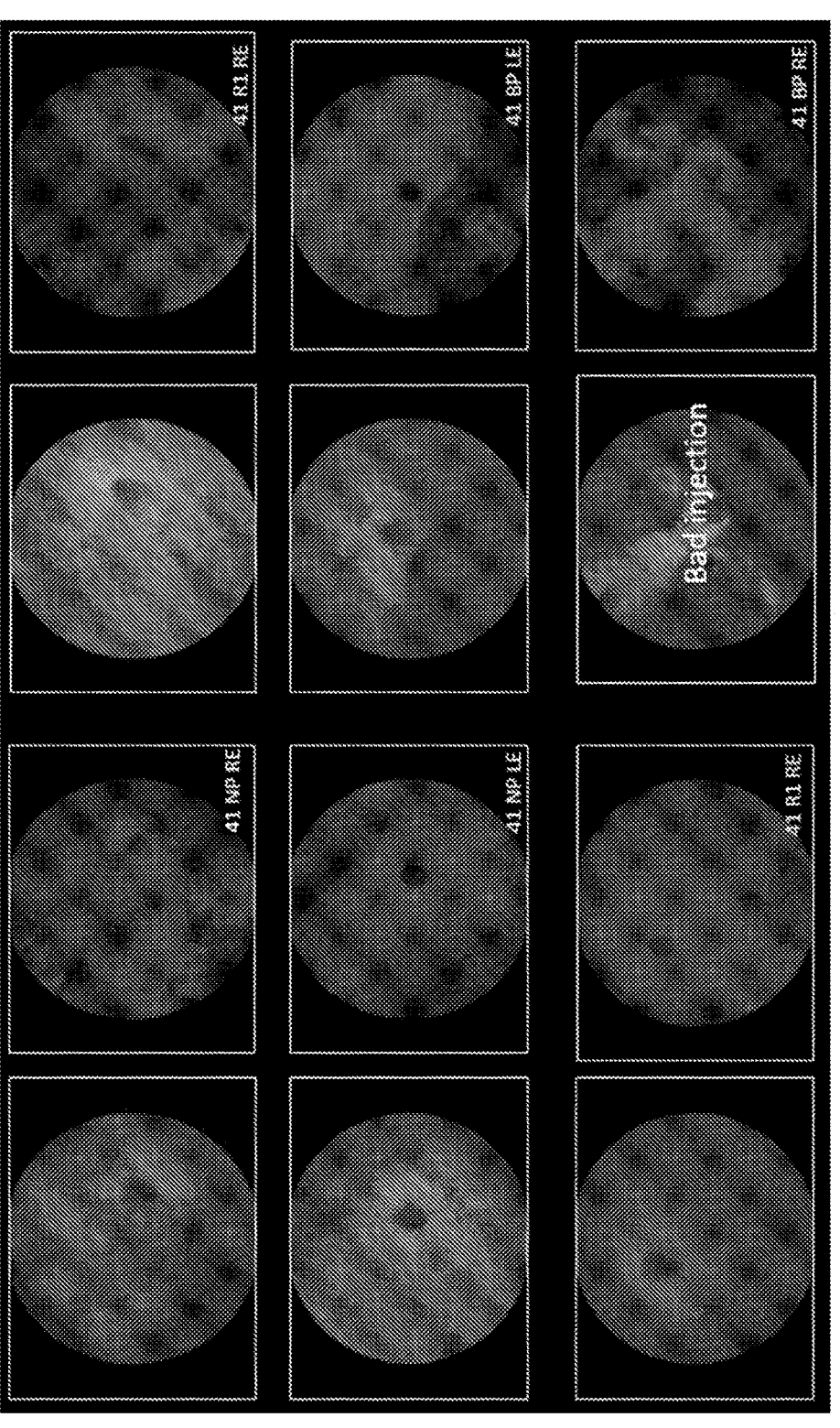
FIG. 10A shows representative fundus images of Nrl-GFP mice taken 4 weeks post subretinal injection with AAVrh.8-mCherry. Vector was delivered at $2\times10^9$ vg in 1 uL. Exposure and gain settings were consistent over the course of the experiment.

Representative fundus images of Nrl-GFP mice were taken 4 weeks post subretinal injection with AAVrh.8-mCherry (see FIG. 10A). Vector was delivered at $2\times10^9$ vg in 1 uL. Both GFP and mCherry filtered images are included. AAVrh.8 was evaluated due to its structural similarity to both AAV44.9 and AAV44.9(E531D).

Figure 10B:
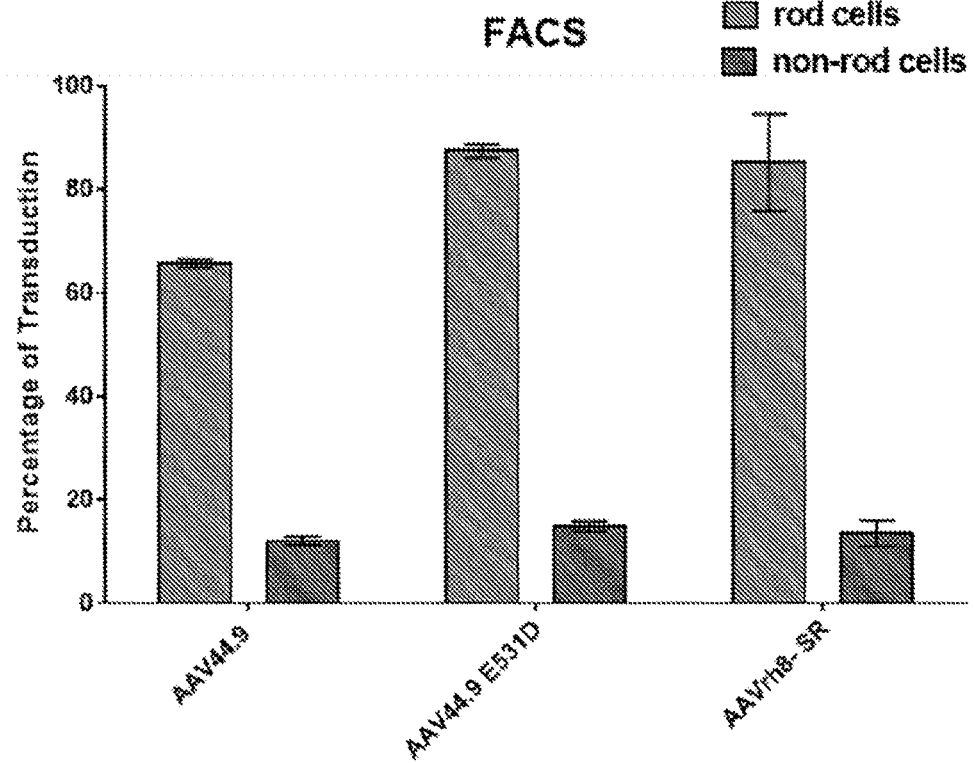
FIG. 10B shows percent transduction of each cell population and corresponding values taken at 4 weeks post-injection. Retinas of Nrl-GFP mice (from FIGS. 9A and 10A) were dissociated with papain and flow cytometry performed to quantify the percentage of transduced rods (GFP+mCherry positive) or non-rod cells (mCherry positive).

At 4 weeks post-injection, retinas of Nrl-GFP mice (same mice from experiment in FIGS. 9A and 10A) were dissociated with papain and flow cytometry was performed to quantify the percentage of transduced rods (GFP+mCherry positive) or non rod cells (mCherry positive). Percent transduction of each cell population and corresponding values are shown in FIG. 10B. AAV44.9(E531D) transduced a higher percentage of rod photoreceptors relative to unmodified AAV44.9 or AAVrh.8.

Figure 11A:
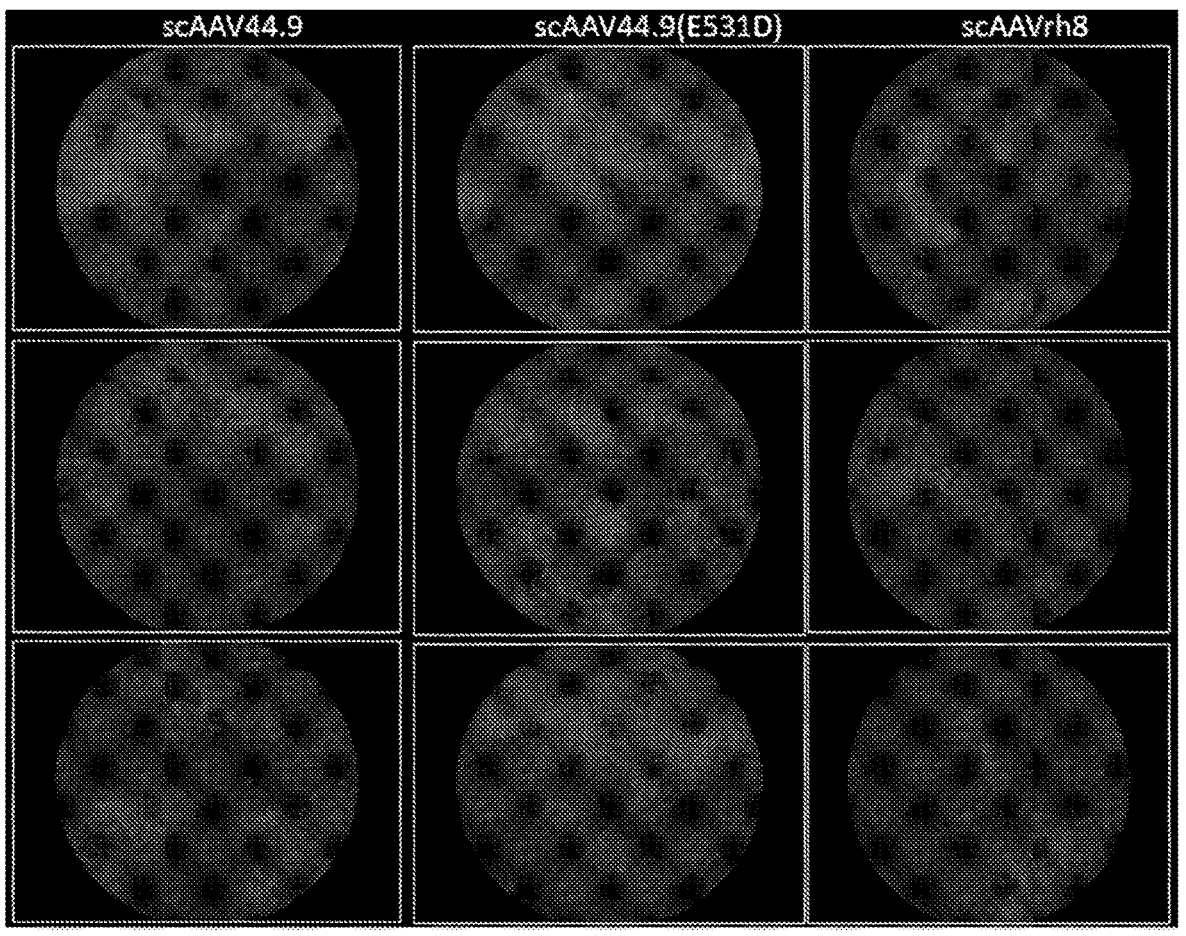
FIG. 11A shows representative fundus images of Nrl-GFP mice taken 4 weeks post subretinal injection with lower titer self-complementary AAV44.9 ("scAAV44.9"), scAAV44.9 (E531D), or scAAVrh.8. Vectors were delivered at $2\times10^8$ vg in 1 uL. Exposure and gain settings were consistent over the course of the experiment.

Representative fundus images of Nrl-GFP mice were taken 4 weeks post subretinal injection with lower titer scAAV44.9, scAAV44.9(E531D), or scAAVrh.8 (see FIG. 11A). Vectors were delivered at $2\times10^8$ vg in 1 uL. Exposure and gain settings were consistent over the course of the experiment.

Figure 11B:
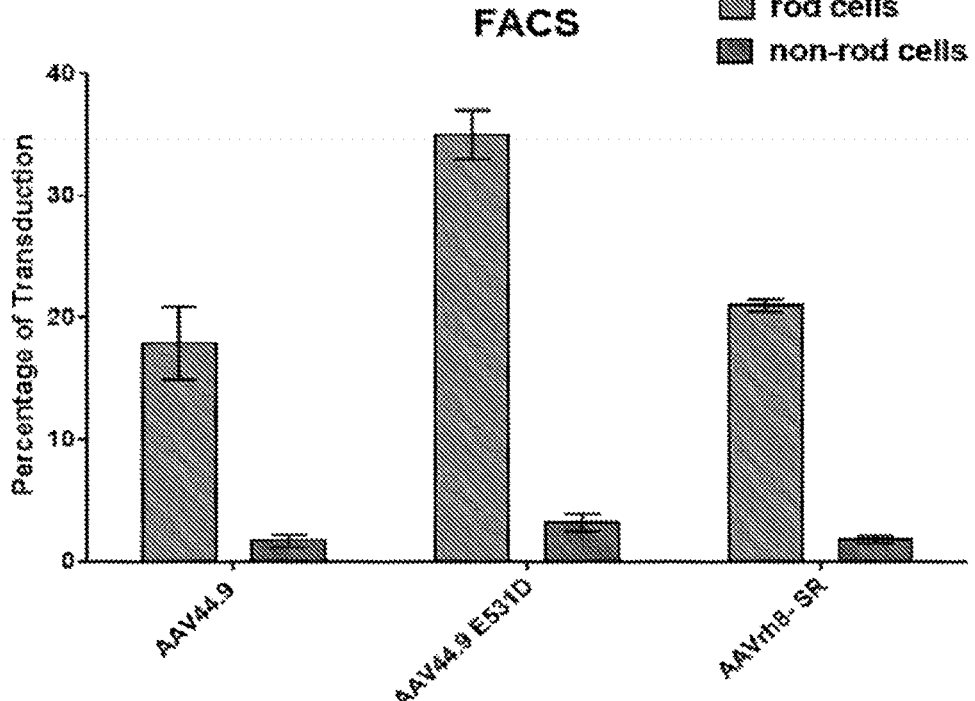
FIG. 11B shows percent transduction of each cell population and corresponding values taken at 4 weeks post-injection. Retinas of Nrl-GFP mice (from FIG. 11A) were dissociated with papain and flow cytometry performed to quantify the percentage of transduced rods (GFP+mCherry positive) or non-rod cells (mCherry positive).

At 4 weeks post-injection, retinas of Nrl-GFP mice (same mice from experiment in FIG. 11A) were dissociated with papain and flow cytometry was performed to quantify the percentage of transduced rods (GFP+mCherry positive) or non rod cells (mCherry positive). Percent transduction of each cell population and corresponding values are shown in FIG. 11B. AAV44.9(E531D) transduced a higher percentage of rod photoreceptors relative to unmodified AAV44.9 or AAVrh.8.

Qualitative and quantitative analysis of AAVrh.8, AAV44.9 and AAV44.9(E531D) at 4 weeks after subretinal injection is shown in FIGS. 9A and 9B. FIG. 9B depicts FACS plots showing that AAV44.9(E531D) transduced rod cells more efficiently than AAV44.9 following subretinal injection with $2\times10^{12}$ vg.

Figure 12:
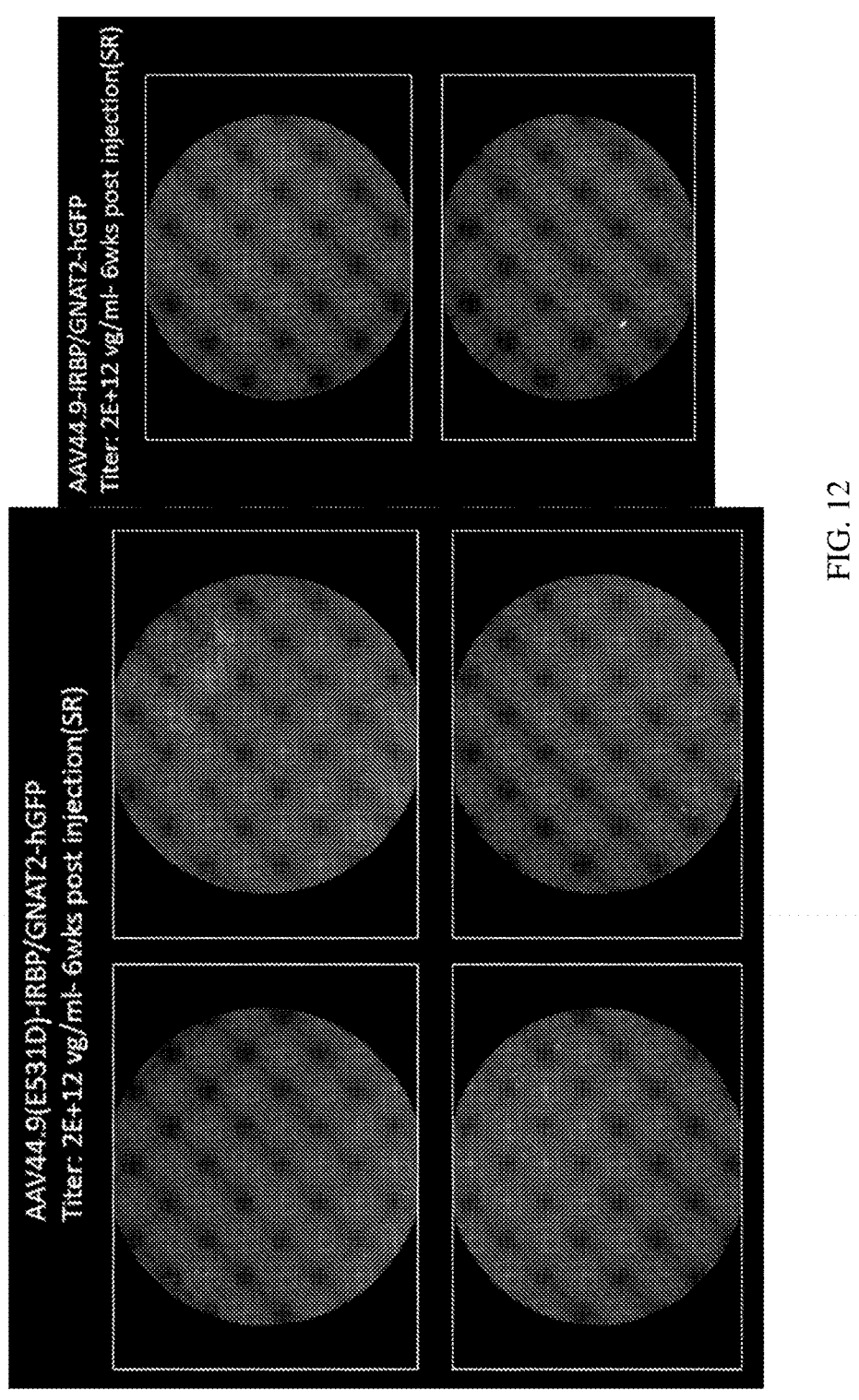
FIG. 12 shows qualitative analysis of AAV44.9(E531D) and unmodified AAV44.9 in context of a cone-specific, IRBPe-GNAT2 chimeric promoter, at 6 weeks after subretinal injection. Fundus images for AAV44.9(E531D)-IRBP/ GNAT2-hGFP and AAV44.9-IRBP/GNAT2-hGFP are shown following subretinal injection with $2\times10^{12}$ vg.

Qualitative and quantitative analysis of AAV44.9, AAV44.9(E531D), and AAVrh.8 at lower titer, at 4 weeks after subretinal injection is shown in FIGS. 11A and 11B. FIG. 11B depicts FACS plots showing that AAV44.9 (E531D) transduced rod cells more efficiently than AAV44.9 (E531D) and AAVrh.8 following subretinal injection with $2\times10^{11}$ vg. Qualitative analysis of AAV44.9(E531D) and AAV44.9 in context of a cone-specific, IRBPe-GNAT2 chimeric promoter, at 6 weeks after subretinal injection is shown in FIG. 12.

Figure 13:
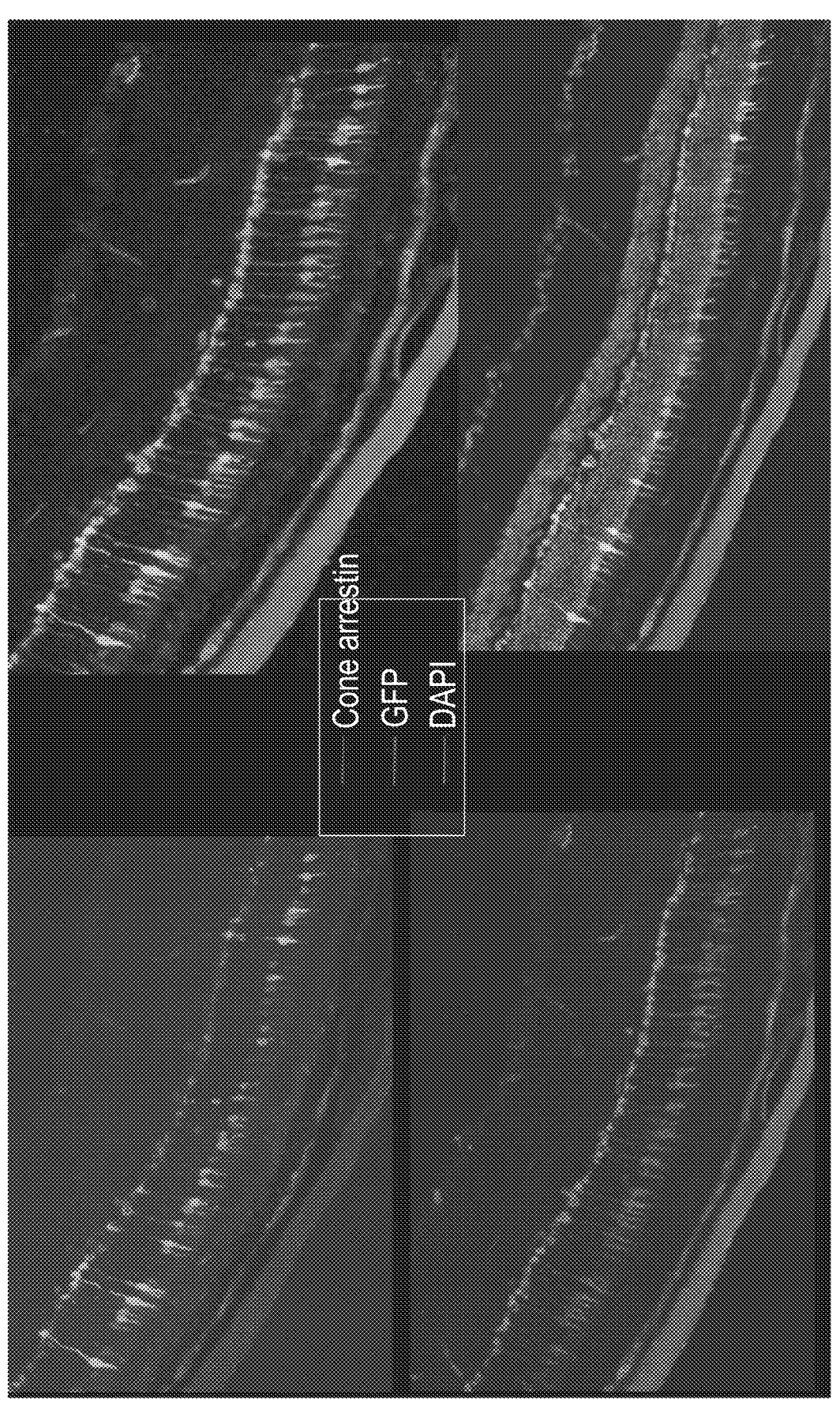
FIG. 13 shows representative retinal cross sections of WT mice taken 6 weeks post subretinal injection with AAV44.9 (E531D)-IRBP/GNAT2-hGFP. Vector was delivered at $2\times10^{12}$ vg in 1 uL. Sections were immunostained with antibodies raised against GFP (green) and cone arrestin (red).

Representative retinal cross sections of WT mice taken 6 weeks post subretinal injection with AAV44.9(E531D)-IRBP/GNAT2-hGFP are shown in FIG. 13. The IRBP/GNAT2 promoter is a cone specific promoter. Vector was delivered at $2\times10^{12}$ vg in 1 uL. Sections were immunostained with antibodies raised against GFP (green) and cone arrestin (red). AAV-mediated GFP expression colocalized with cone arrestin (a cone specific marker) confirming that this vector efficiently transduced cones. Representative retinal cross section images in FIG. 13 show cone arrestin expression in photoreceptors and RPE in Nrl-GFP mouse retina injected with AAV44.9(E531D) and indicate that AAV44.9(E531D) transduces cones very effectively.

Figure 14:
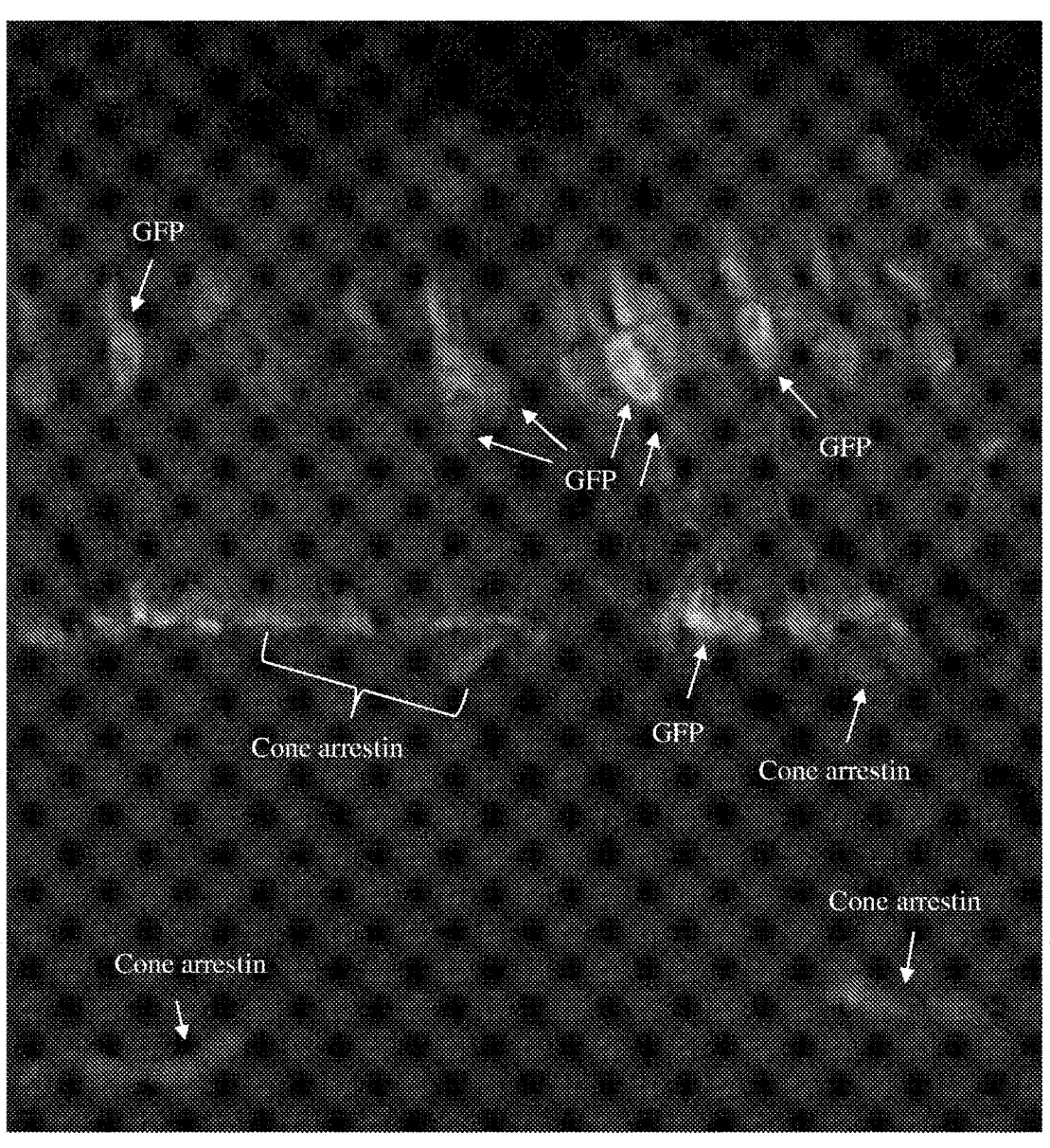
FIG. 14 shows representative retinal cross sections of WT mouse taken 6 weeks post subretinal injection with AAV44.9-IRBP/GNAT2-hGFP. Vector was delivered at $2\times10^{12}$ vg in 1 uL. Sections were immunostained with antibodies raised against GFP and cone arrestin, as indicated by arrows.

Representative retinal cross sections of WT mouse were taken 6 weeks post subretinal injection with AAV44.9-IRBP/GNAT2-hGFP (see FIG. 14). The IRBP/GNAT2 promoter is a cone specific promoter. Vector was delivered at $2\times10^{12}$ vg in 1 uL. Sections were immunostained with antibodies raised against GFP (green) and cone arrestin (red). AAV-mediated GFP expression colocalizes with cone arrestin (a cone specific marker) confirming that this vector efficiently transduces cones.

Example 2-Enhanced Lateral Spread and Foveal Transduction Following Subretinal Administration of AAV44.9(E531D)-hGRK1-GFP in Macaque It was previously determined that the human rhodopsin kinase (hGRK1) promoter has exclusive activity in non-human primate rods and cones. As such, the hGRK1 promoter was evaluated for its ability to drive GFP reporter expression in macaque eyes in the improved AAV44.9 (E531D) vector. The degree of lateral spread from the initial bleb boundaries was also evaluated.

Two rAAV vectors—AAV44.9-hGRK1-GFP and AAV44.9(E531D)-hGRK1-GFP—were subretinally administered to macaque eyes. Vectors were delivered at concentrations of $1\times10^{12}$ vg/mL. A control vector, AAV5-hGRK1-GFP, was also administered to the eyes.

Figure 15:
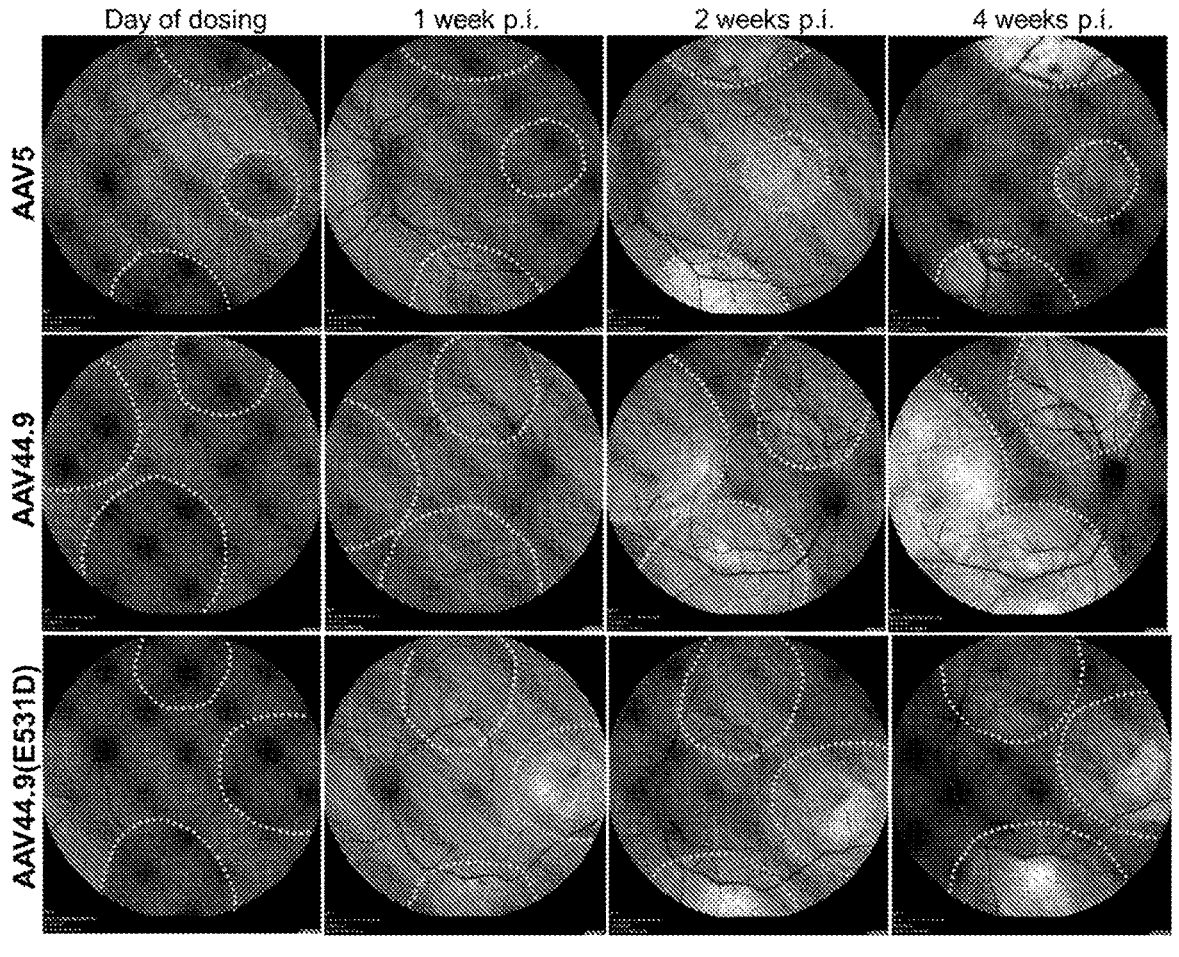
FIG. 15 shows AAV44.9-hGRK1-GFP and AAV44.9 (E531D)-hGRK1-GFP exhibit enhanced lateral spread and potency in subretinally injected macaques. Vector delivered at $1\times10^{12}$ vg vg/mL. Initial boundaries of blebs on day of dosing and borders of resulting GFP expression are outlined in white line. Identical vasculature is highlighted in thickened dark lines for reference.

Particles incorporating both modified and unmodified AAV44.9 vectors exhibited enhanced lateral spread and potency in subretinally injected macaque subjects (see FIG. 15). Initial boundaries of the bleb and boundaries of resulting GFP expression are outlined in white dotted line in FIG. 15. Identical vasculature is highlighted in thickened dark line for reference. GFP expression mediated by AAV44.9 (E531D) was visible at 1 week post injection. Both AAV44.9 and AAV44.9(E531D) were well tolerated in the primate retina at the $1\times10^{12}$ vg/mL dose. The control vector, AAV5, mediated GFP restriction that remained sequestered within the original injection bleb.

Figure 16:
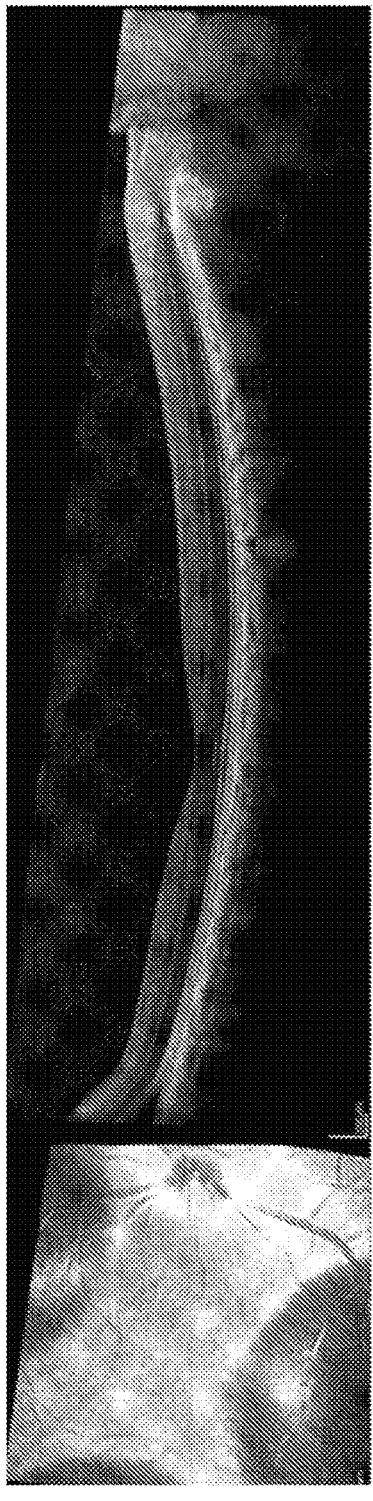
FIG. 16 shows optical coherence tomography (OCT) scans of three subretinal injection blebs created (see negative contrast fundus image on the left), following extrafoveal subretinal injection of AAV44.9-hGRK1-GFP ($1\times10^{12}$ vg/mL) in macaque.
Figure 17:
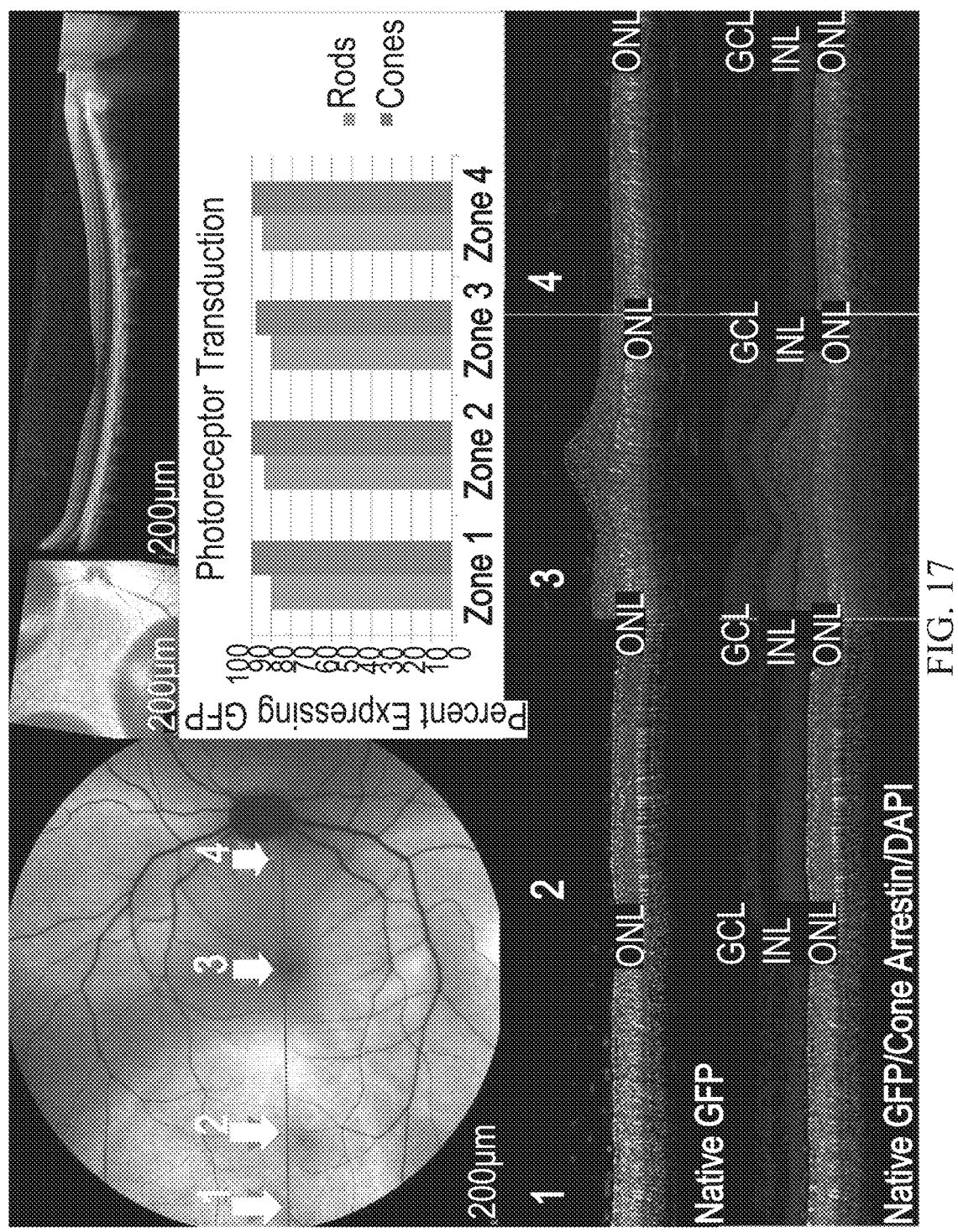
FIG. 17 shows OCT images of macaque retinas following extrafoveal subretinal injection of AAV44.9-hGRK1-GFP. Arrows in SLO image (top left) indicate the locations of retinal sections shown in the scans in the lower part of the figure. Sections were stained for cone arrestin and DAPI. The percentage of rods/cones expressing GFP is plotted in each zone. ONL, outer nuclear layer; INL, inner nuclear layer; GCL, ganglion cell layer.

An extrafoveal subretinal injection of AAV44.9-hGRK1-GFP (concentration of $1\times10^{12}$ vg/mL) were performed in macaque subjects. OCT scans revealed that the fovea was not detached during the injection (FIG. 16). This extrafoveal subretinal injection transduced 98% of foveal cones even and 100% of central rods, even though the fovea did not detach (see top right of FIG. 17). The capsid exhibited enhanced lateral spread, as bleb boundaries were expanded relative to the initial boundaries.

Images were also captured from macaque eyes injected with AAV44.9(E531D)-hGRK1-GFP. A qualitative analysis in a single eye revealed ~50% of foveal cone transduction mediated by AAV44.9(E531D).

Figure 19:
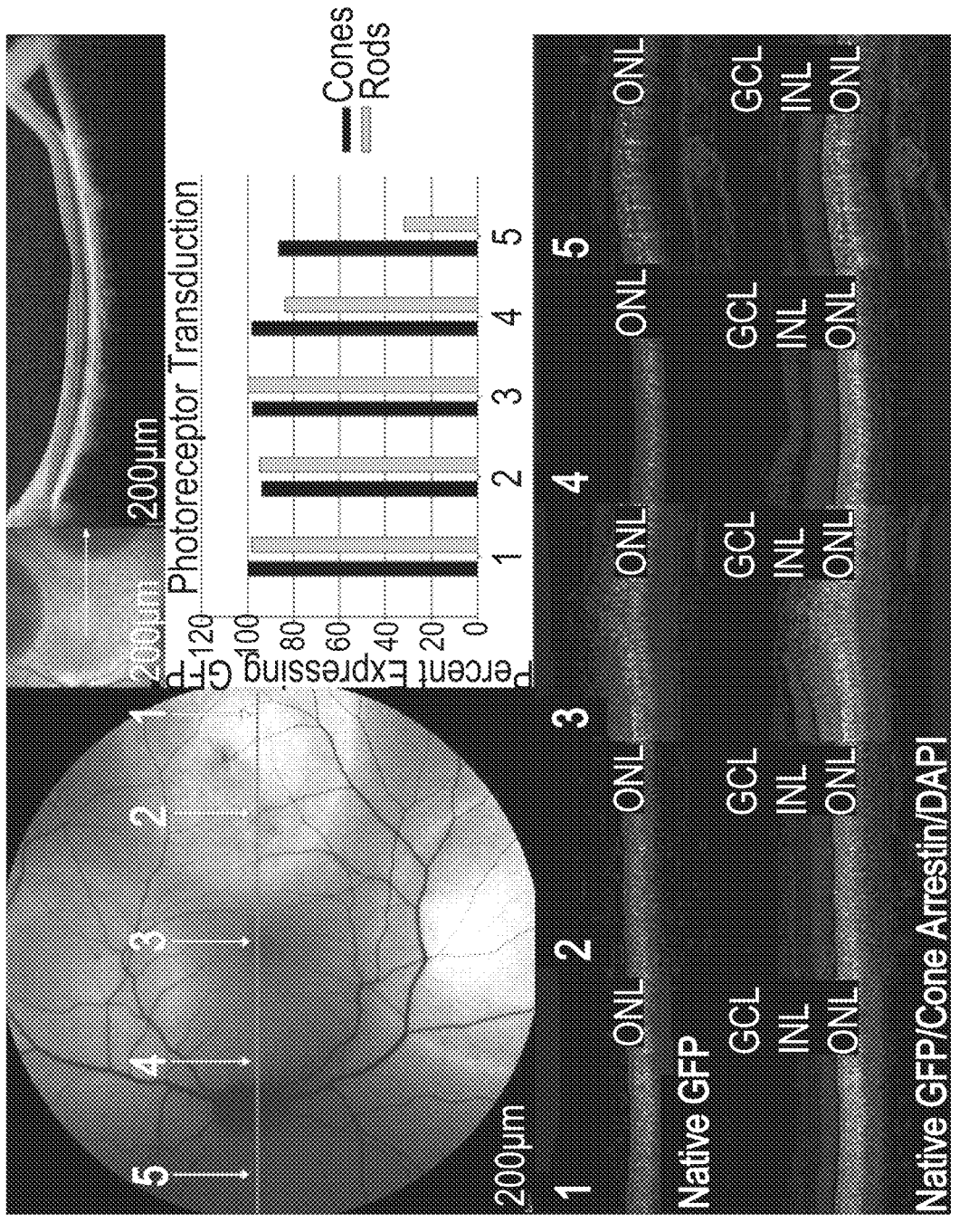
FIG. 19 shows OCT images of macaque retinas following extrafoveal subretinal injection of AAV44.9(E531D)-hGRK1-GFP. Arrows in SLO image (top left) indicate the locations of retinal sections shown in the scans in the lower part of the figure. Sections were stained for cone arrestin and DAPI. The percentage of rods/cones expressing GFP is plotted in each zone.

Three subretinal injections (30 μL each) of AAV44.9 (E531D)-hGRK1-GFP were performed in the superior, temporal, and inferior retina outside the fovea of macaque eyes. Retinal sections were stained with an antibody directed against cone arrestin and three blinded observers counted the number of GFP positive cones and rods in 5 retinal regions across a single plane traversing the foveal pit. Results of this administration are shown in FIG. 19. OCT scans revealed that the fovea was not detached during the injection (see right panel of FIG. 19).

These results indicate that extrafoveal subretinal injection in macaque of AAV44.9(E531D)-hGRK1-GFP exhibited remarkable transduction of central cone and rod cells in the absence of foveal detachment. Peripheral rods and cones were also transduced very efficiently. Accordingly, extrafoveal subretinal injection resulted in highly efficient transduction across the foveal region.

As shown in FIGS. 20A-20D, an examination of the parafovea following this injection revealed that the AAV44.9(E531D) particles transduced parafoveal cones located both nasal and temporal to the foveal pit. Notably, however, parafoveal cone transduction was not achieved with unmodified AAV44.9. This finding is of interest at least because i) parafoveal cones are refractory to transduction by a variety of AAV capsid variants, and ii) the earliest loss of structure and function due to aging and inherited retinal disease often occurs in the parafoveal region. Despite the dissimilarity in their ability to transduce cones in this region, the modified and unmodified AAV44.9 vectors efficiently transduced parafoveal rods to a substantially equal degree.

Figure 20A:
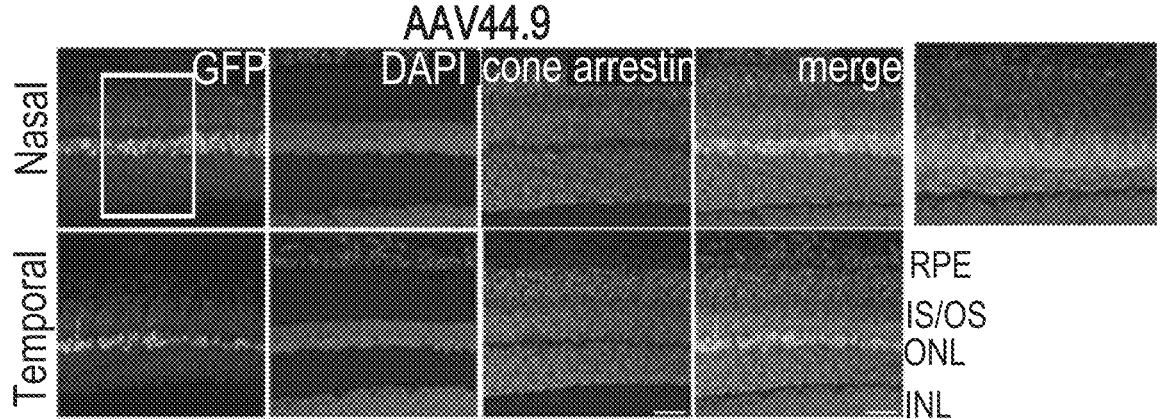
FIGS. 20A, 20B, 20C, and 20D show representative OCT images of parafoveal regions of macaque retinas following extrafoveal subretinal injection of AAV44.9(E531D)-hGRK1-GFP and AAV44.9-hGRK1-GFP. Scale bars are in A=40 microns, B=20 microns.
Figure 20B:
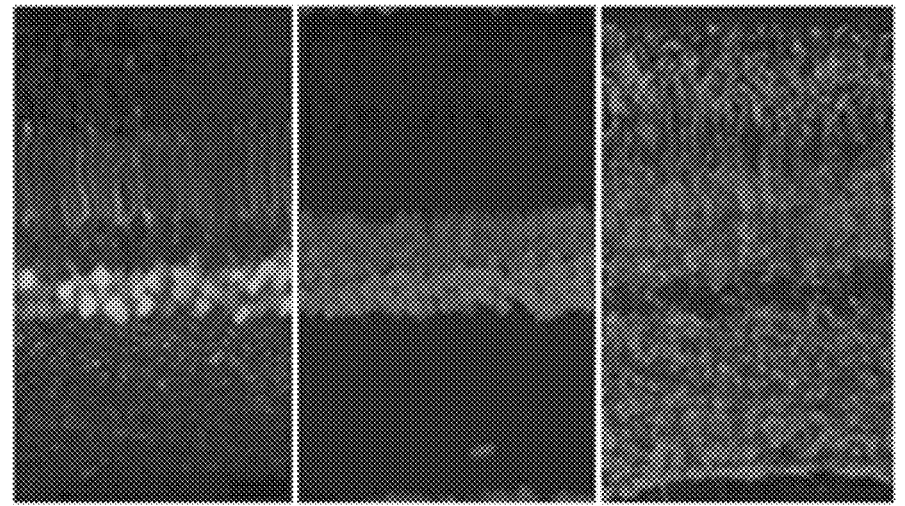
Figure 20C:
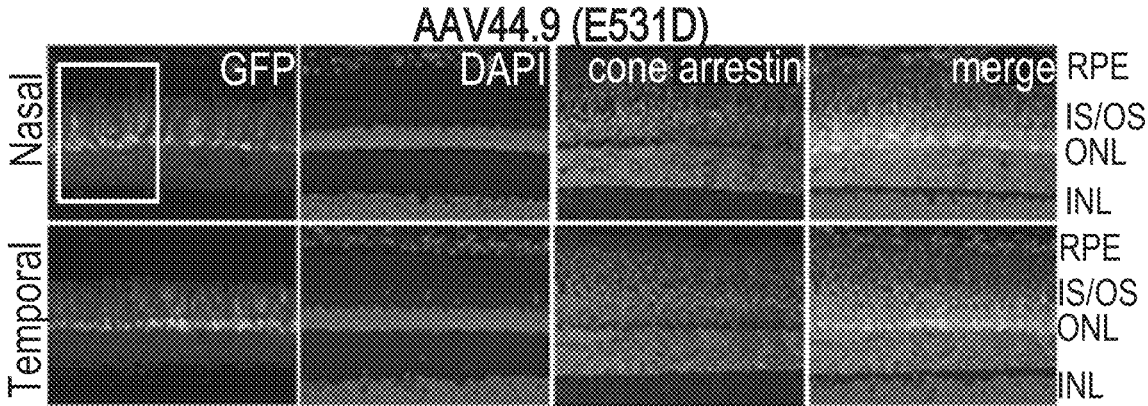
Figures 20D, 21A:
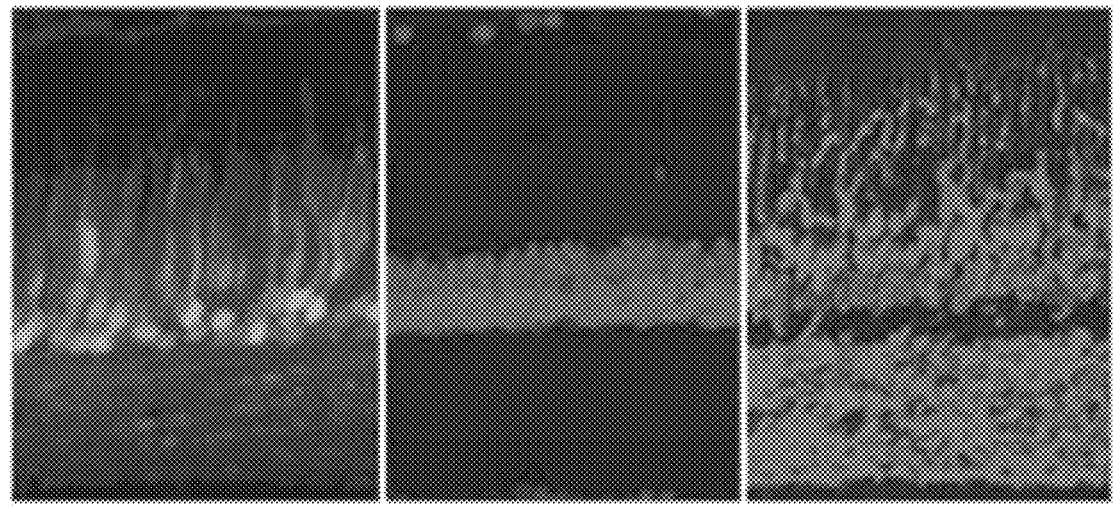
FIGS. 21A and 21B show representative OCT images of perifoveal regions of macaque retinas following these injections.
Figure 21B:
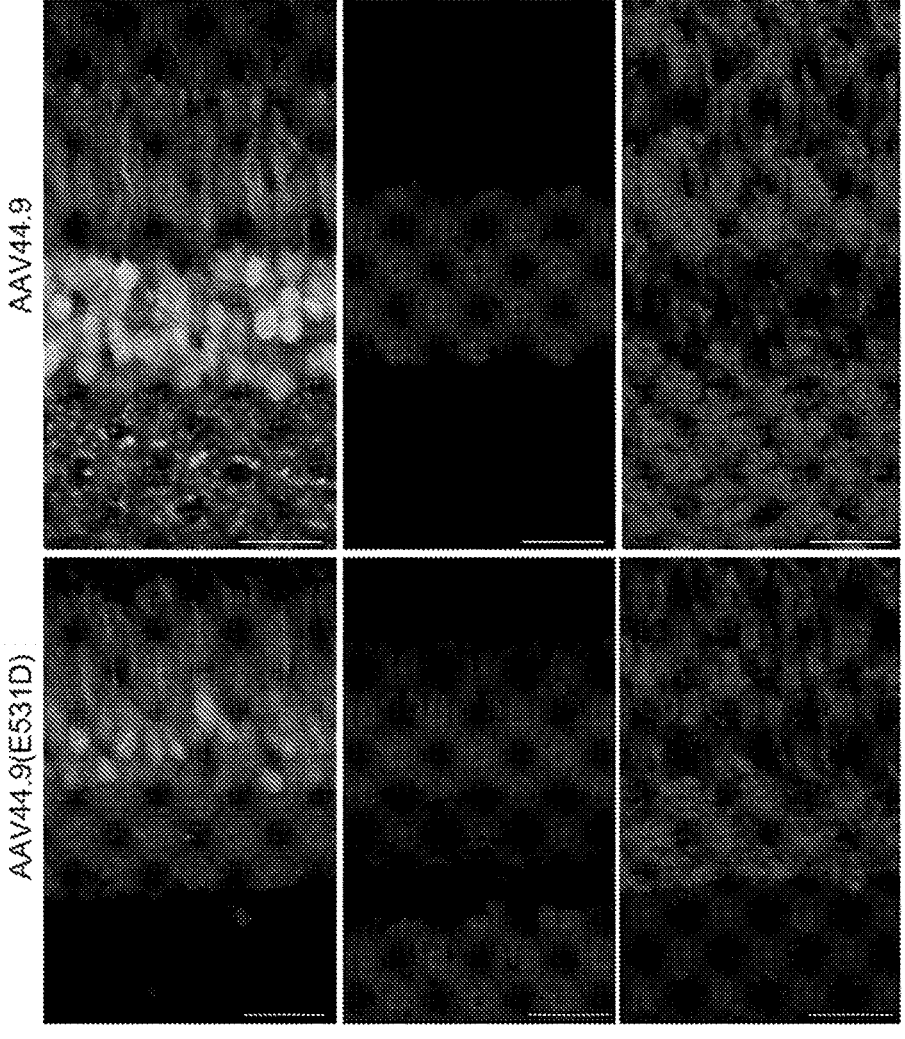

As shown in FIGS. 21A-21B, an examination of the perifovea revealed a similar pattern: particles that incorporated the AAV44.9(E531D) capsid transduced perifoveal cones, but unmodified AAV44.9 did not. Perifoveal rods were efficiently transduced by both capsids in this region. The perifovea circumscribes the parafovea.

These results further demonstrate that the enhanced lateral spread of transduction provided by the improved AAV44.9 (E531D) capsid variant vectors may allow subretinal injection in the parafoveal region to produce transduction of the foveal cells while circumventing the deleterious effects of inducing a foveal detachment in human subjects.

Example 3-Enhanced Lateral Spread Following Subretinal Administration of AAV44.9-Gucy2e-GFP in Mouse The previous example demonstrated foveal transduction of a reporter gene delivered by the improved AAV44.9 (E531D) vector. The degree of lateral spread following administration of the improved AAV44.9(E531D) vector encoding a therapeutic peptide of interest was next determined. The selected therapeutic peptide of interest was Gucy2e, the murine homolog of human guanylate cyclase 2D, GUCY2D.

Two vectors—AAV44.9(E531D)-hGRK1-Gucy2e and AAV8 (Y733F)-hGRK1-Gucy2e—were administered subretinally to the eyes of retinal guanylate cyclase ½ double knockout (GCdko) mice. The GCdko mouse has a complete lack of retinal function. Due to the absence of any functioning retinal guanylate cyclase in these photoreceptors, neither rods nor cones are capable of responding to light. Gene replacement therapy performed in the GCdko mouse therefore can evaluate whether gene replacement/supplementation is successful in rod and cone cells simultaneously. Vectors were delivered at concentrations of $1\times10^{13}$ vg/mL. The response functions of treated and untreated eyes were evaluated by electroretinogram (ERG) measurements. The ERG response from photoreceptor cells of the retina is termed the "a-wave," and the electrical response from the bipolar cells of the retina is termed the "b-wave."

Figures 18A, 18B:
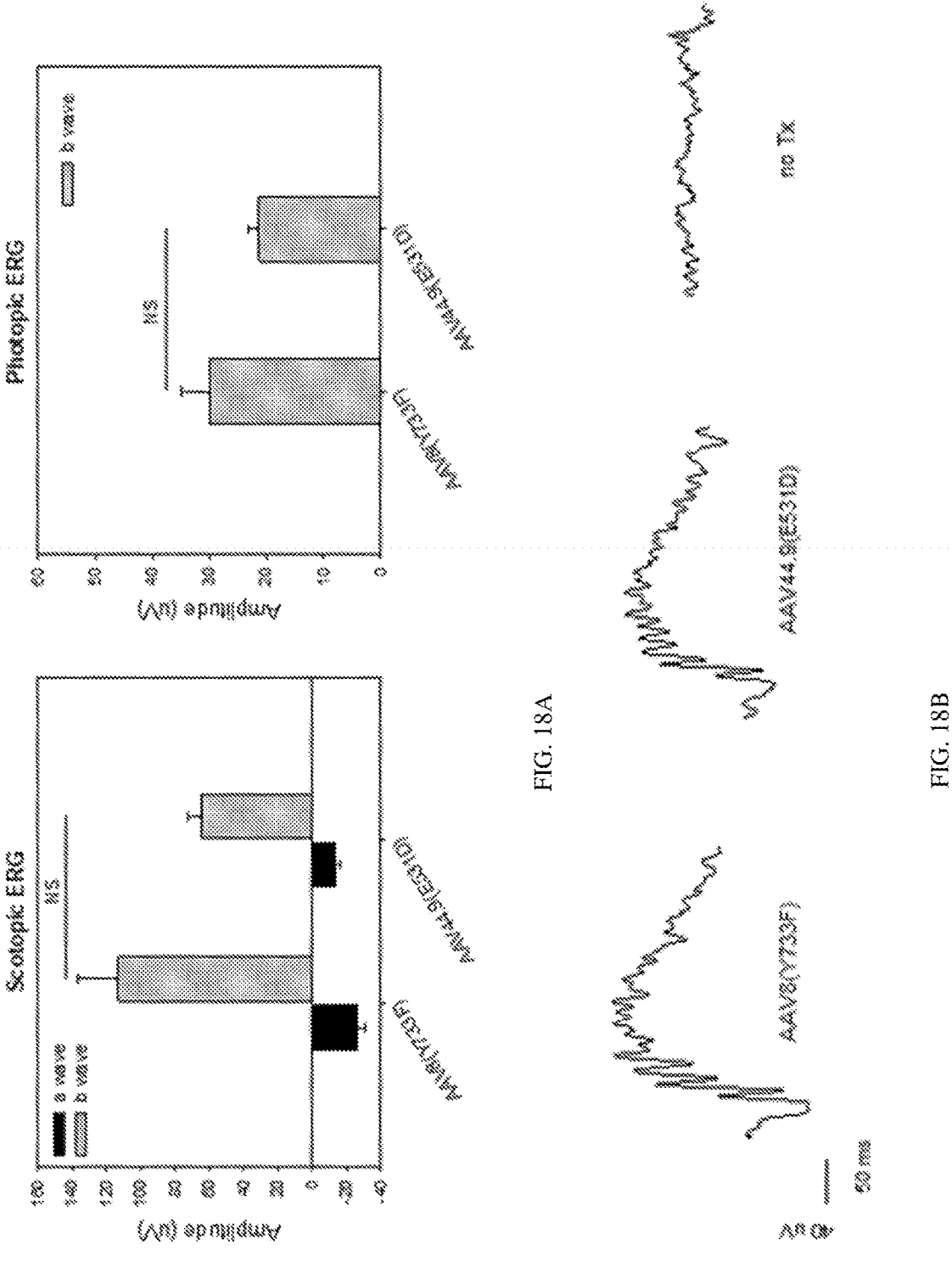
FIGS. 18A and 18B show ERG recordings in retinal guanylate cyclase ½ double knockout (GCdko) mice following subretinal injection with AAV44.9(E531D)-hGRK1-

As shown in FIG. 18B, the light response functions of cone cells from eyes treated with AAV vectors were improved relative to those of untreated eyes. These results indicate that both classes of photoreceptors were efficiently targeted by rAAV particles that incorporate the AAV44.9 (E531D) capsid and the AAV44.9(Y733F) capsid. As shown in FIG. 18A, maximum a- and b-wave amplitudes were greater after administration of the AAV (Y733F) vector than the AAV44.9(E531D) vector.

Another major implication of this experiment is that clinical candidate rAAV vectors expressing therapeutic peptides designed to treat inherited retinal diseases (e.g., vectors for delivery of the human GUCY2D) transgene) that incorporate AAV44.9(E531D) are likely to work in the respective murine models of the disease (e.g., vectors for delivery of murine Gucy2e). This is advantageous in the context of pre-clinical development and evaluation of various lots of candidate drug during the various stages or phases of manufacturing.

Other Embodiments

It should be understood that the examples and embodiments described herein are for illustrative purposes only and that various modifications or changes in light thereof may be suggested to persons skilled in the art and are to be included within the spirit and purview of this application and the scope of the appended claims. All references, including publications, patent applications and patents, cited herein are hereby incorporated by reference to the same extent as if each reference was individually and specifically indicated to be incorporated by reference and was set forth in its entirety herein. Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

All of the compositions and methods disclosed and claimed herein may be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically and/or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A recombinant adeno-associated viral (rAAV) particle comprising a capsid protein comprising the amino acid sequence of SEQ ID NO: 3.

2. The rAAV particle of claim 1, further comprising a VP1 capsid protein and a VP2 capsid protein, wherein the VP1 capsid protein comprises the amino acid sequence of SEQ ID NO: 1 and the VP2 capsid protein comprises the amino acid sequence of SEQ ID NO: 2.

3. The rAAV particle of claim 1, further comprising a heterologous nucleic acid sequence operably linked to one or more regulatory sequences that direct expression of the heterologous nucleic acid sequence in a photoreceptor (PR) cell or a retinal pigment epithelium (RPE) cell, wherein the heterologous nucleic acid sequence comprises GUCY2D, AIPL1, LCA5, RPGRIP1, CRX, CRB1, NMNAT1, CEP290, IMPDH1, RD3, RDH12, TULP1, KCNJ13, GDF6, IQCB1, SPATA7 or PRPH2.

4. The rAAV particle of claim 3, wherein the one or more regulatory sequences comprises a human rhodopsin kinase (hGRK1) promoter.

5. The rAAV particle of claim 3, wherein the heterologous nucleic acid sequence encodes a peptide.

6. A composition comprising the rAAV particle of claim 1, further comprising one or more pharmaceutically acceptable carriers, buffers, diluents or excipients.

7. The rAAV particle of claim 6, wherein the one or more pharmaceutically acceptable carriers, buffers, diluents or excipients comprises balanced salt solution.

8. The rAAV particle of claim 6, wherein the one or more pharmaceutically acceptable carriers, buffers, diluents or excipients comprises polysorbate 20.

9. The rAAV particle of claim 6, wherein the one or more pharmaceutically acceptable carriers, buffers, diluents or excipients comprises balanced salt solution supplemented with 0.014% w/v polysorbate 20.

10. An isolated cell comprising the rAAV particle of claim 1.

11. The rAAV particle of claim 1, further comprising a heterologous nucleic acid sequence comprising a sequence selected from ABCA4, CRX, GUCA1A (GCAP1) and GUCA1B (GCAP2).

12. The rAAV particle of claim 1, further comprising a heterologous nucleic acid sequence, wherein the heterologous nucleic acid sequence comprises RS1.

13. The rAAV particle of claim 1, further comprising a heterologous nucleic acid sequence comprising a sequence selected from BBS1, BBS2, ARL6/BBS3, BBS4, BBS5, BBS7, TTC8/BBS8, BBS10, TRIM32/BBS11, BBS12, CCDCC28B, CEP290, TMEM67, MKS1 and MKKS.

14. The rAAV particle of claim 1, further comprising a heterologous nucleic acid sequence comprising a sequence selected from RHO, PRPF31, RP1, NRL, NR2E3, RPGR, RP2, PDE6A, PDE6B, PDE6G, RP25, CNGA1, CNGB1 and MAK.

15. The rAAV particle of claim 1, further comprising a heterologous nucleic acid sequence comprising a sequence selected from OPN1LW, OPN1MW, CNGB3, CNGA3, and GNAT2.

16. The rAAV particle of claim 1, further comprising a heterologous nucleic acid sequence comprising a sequence selected from MYO7A, USH1C, CDH23, PCDH15 and USH1G, USH2A, DFNB31, and CLRN1.

17. The rAAV particle of claim 1, further comprising a heterologous nucleic acid sequence comprising a sequence selected from GUCY2D, AIPL1, LCA5, RPGRIP1, CRX, CRB1, NMNAT1, CEP290, IMPDH1, RD3, RDH12, TULP1, KCNJ13, GDF6, IQCB1, SPATA7 and PRPH2.

18. A capsid protein comprising the amino acid sequence of any one of SEQ ID NOs: 1, 2, and 3.

19. A nucleic acid molecule comprising the nucleic acid sequence of any one of SEQ ID NOs: 4, 5, and 6.

* * * * *